(12) United States Patent
Yen et al.

(10) Patent No.: US 10,400,002 B2
(45) Date of Patent: Sep. 3, 2019

(54) IRIDIUM COMPLEX AND ORGANIC ELECTROLUMINESCENCE DEVICE USING THE SAME

(71) Applicants: Feng-Wen Yen, Taipei (TW); Tsun-Yuan Huang, Chiayi (TW)

(72) Inventors: Feng-Wen Yen, Taipei (TW); Tsun-Yuan Huang, Chiayi (TW)

( * ) Notice: Subject to any disclaimer, the term of this patent is extended or adjusted under 35 U.S.C. 154(b) by 129 days.

(21) Appl. No.: 15/721,965

(22) Filed: Oct. 2, 2017

(65) Prior Publication Data

US 2019/0100543 A1    Apr. 4, 2019

(51) Int. Cl.
| | | |
|---|---|---|
| *H01L 51/54* | (2006.01) | |
| *C09K 11/06* | (2006.01) | |
| *C07F 15/00* | (2006.01) | |
| *H01L 51/00* | (2006.01) | |
| *H01L 51/50* | (2006.01) | |

(52) U.S. Cl.
CPC .......... *C07F 15/0033* (2013.01); *C09K 11/06* (2013.01); *H01L 51/0072* (2013.01); *H01L 51/0085* (2013.01); *C09K 2211/1029* (2013.01); *C09K 2211/1059* (2013.01); *C09K 2211/1096* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 2002/0034656 A1* | 3/2002 | Thompson et al. | C07D 209/86 428/690 |
| 2016/0111660 A1 | 4/2016 | Yang et al. | |
| 2016/0233442 A1 | 8/2016 | Yen et al. | |
| 2018/0277765 A1* | 9/2018 | Yen | H01L 51/0071 |

* cited by examiner

*Primary Examiner* — Marie R. Yamnitzky

(57) ABSTRACT

An iridium complex of formula (1) and an organic electroluminescence device employing the iridium complex as the phosphorescent dopant material are described. The organic EL device can display good performance, such as lower driving voltage, reduced power consumption, increased efficiency, and longer half-life time.

Formula (1)

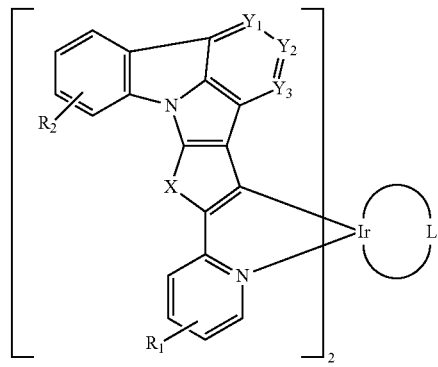

9 Claims, 1 Drawing Sheet

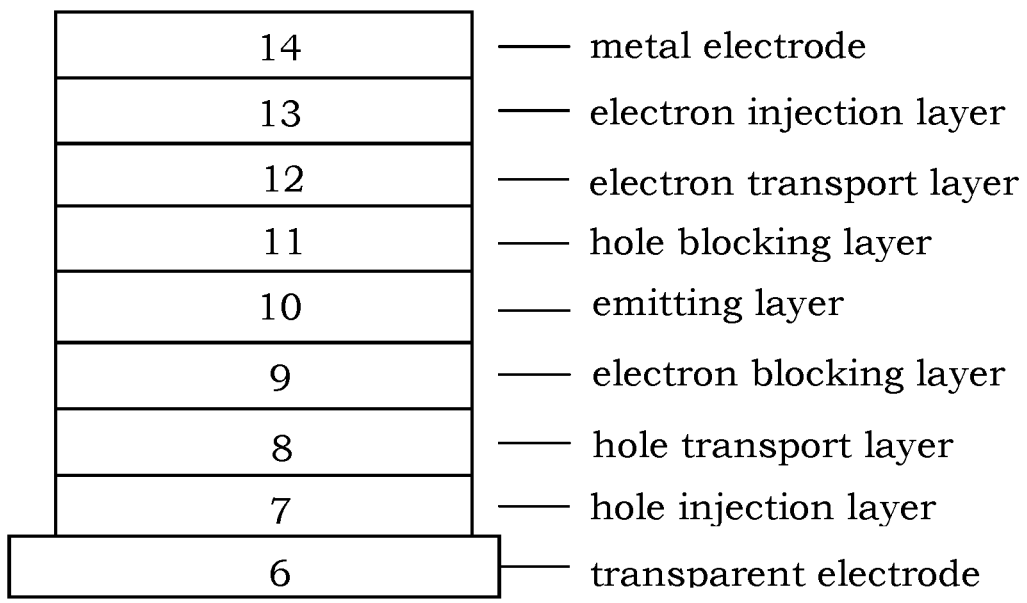

IRIDIUM COMPLEX AND ORGANIC ELECTROLUMINESCENCE DEVICE USING THE SAME

FIELD OF INVENTION

The present invention relates generally to an iridium complex, and, more specifically, to an organic electroluminescence (hereafter referred to as organic EL) device using the iridium complex.

BACKGROUND OF THE INVENTION

An organic EL device is a light-emitting diode (LED) in which the light emitting layer is a film made from organic compounds, which emits light in response to an electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

The first observation of electroluminescence in organic materials was in the early 1950s by Andre Bernanose and his co-workers at the Nancy-University in France. Martin Pope and his co-workers at New York University first observed direct current (DC) electroluminescence on a single pure crystal of anthracene and on anthracene crystals doped with tetracene under vacuum in 1963. The first diode device was created by Ching W. Tang and Steven Van Slyke at Eastman Kodak in 1987. The diode device used a two-layer structure with separate hole transporting and electron transporting layers, resulting in reduction of operating voltage and improvement of the efficiency, thereby leading to the current era of organic EL research and device production.

Typically, organic EL device is composed of organic material layers sandwiched between two electrodes. The organic material layers include the hole transporting layer, the light emitting layer, and the electron transporting layer. The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from a cathode into a LUMO (lowest unoccupied molecular orbital) and holes will be injected from an anode into a HOMO (highest occupied molecular orbital). Subsequently, the electrons recombine with holes in the light emitting layer to form excitons and then emit light. When luminescent molecules absorb energy to achieve an excited state, the exciton may either be in a singlet state or a triplet state, depending on how the spins of the electrons and holes have been combined. 75% of the excitons is formed by recombination of electrons and holes to achieve the triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is achieved by certain heavy atoms, such as iridium, rhodium, platinum, and palladium, and the phosphorescent transition may be observed from an excited MLCT (metal to ligand charge transfer) state of organic metallic complexes.

The phosphorescent organic EL device utilizes both triplet and singlet excitons. Cause of longer lifetime and diffusion length of triplet excitions compared to those of singlet excitions, the phosphorescent organic EL device generally need an additional hole blocking layer (HBL) between the emitting layer (EML) and the electron transporting layer (ETL) or an electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or the electron blocking materials must have HOMO (highest occupied molecular orbital) and LUMO (lowest unoccupied molecular orbital) energy levels suitable to block hole or electron transport from the EML to the ETL or the HTL.

For full-colored flat panel displays in AMOLED or OLED lighting field, the conventional materials used for the phosphorescent guest in light emitting layer, such as the metallic complexes, are still unsatisfactory in driving voltage, luminous efficiency and half-life time, and still have disadvantages for industrial practice use.

There are some prior-arts disclosing iridium complexes, such as U.S. Pat. No. 8,795,850B2, U.S. Pat. No. 8,778, 508B2, U.S. Pat. No. 8,722,205B2, U.S. Pat. No. 8,709, 615B2, U.S. Pat. No. 8,779,176B2, but there is no prior art disclosing the iridium complex of the present invention and its use in the organic EL device.

SUMMARY OF THE INVENTION

According to the reasons described above, the present invention has the objective of resolving the problems of prior arts and offering an organic EL device, which has high luminous efficiency and long half-life time. The present invention discloses a novel iridium complex, which is used as a phosphorescent dopant to lower driving voltage and power consumption and increase luminous efficiency and half-life time of organic EL devices. In the present invention, we employ a pyridine-substituted fused thieno[2,3-b] indole derivative skeleton chelated with iridium metal, which is then substituted with one or two bidentate ligands to prepare the iridium complex of the present invention. The iridium complex exhibits good thermal stability in the process for producing the organic EL device.

The present invention has the economic advantages for industrial practice. Accordingly, the present invention discloses a iridium complex which can be used in organic EL devices. The mentioned iridium complex is represented by the following formula (1):

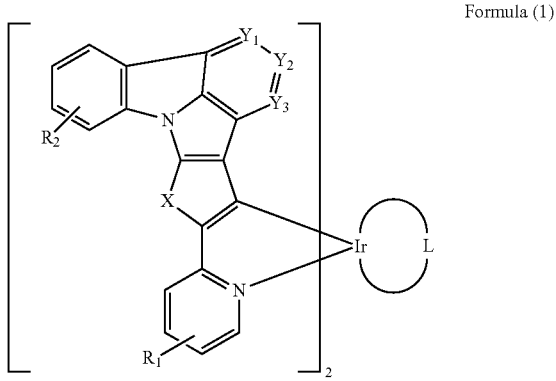

Formula (1)

wherein X is an oxygen atom, a sulfur atom, a selenium atom, $NR_3$, or $CR_4R_5$, $Y_1$ to $Y_3$ are each independently a nitrogen atom or $CR_6$, and L represents formula (2):

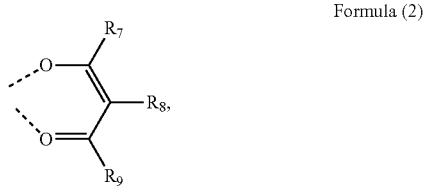

Formula (2)

wherein $R_1$ to $R_9$ are the same or different and each independently selected from the group consisting of a hydrogen atom, a substituted or unsubstituted alkyl group having 1 to 20 carbon atoms, a substituted or unsubstituted carbocyclic ring having 3 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

The present invention further discloses an organic electroluminescence device. The organic electroluminescence device comprises a pair of electrodes composed of a cathode and an anode, and a light emitting layer between the pair of electrodes. The light emitting layer comprises the iridium complex of formula (1).

BRIEF DESCRIPTION OF THE DRAWINGS

The FIGURE is a schematic view showing an embodiment of the organic EL device of the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is phosphorescent emitting layer which is deposited onto 9, 11 is hole blocking layer which is deposited onto 10, 12 is electron transport layer which is deposited onto 11, and 13 is electron injection layer which is deposited onto 12.

DESCRIPTION OF THE PREFERRED EMBODIMENTS

What probed into the invention is the iridium complex and organic EL device using the iridium complex. Detailed descriptions of the production, structure and elements will be provided as follows such that the invention can be fully understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an iridium complex which can be used as phosphorescent dopant material of light emitting layer for organic EL device is disclosed. The iridium complex is represented by the following formula (1):

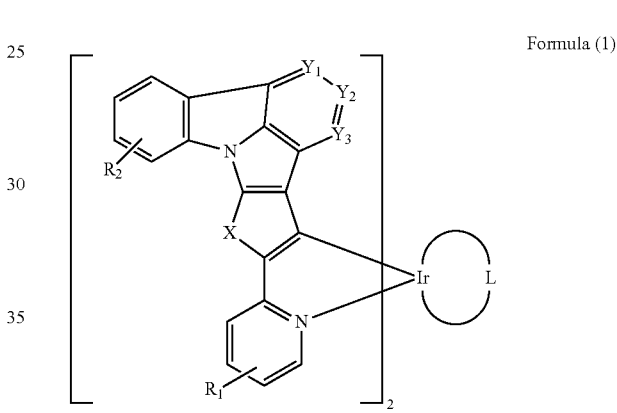

Formula (1)

wherein X is an oxygen atom, a sulfur atom, a selenium atom, $NR_3$, or $CR_4R_5$, $Y_1$ to $Y_3$ are each independently a nitrogen atom or $CR_6$, and L represents formula (2):

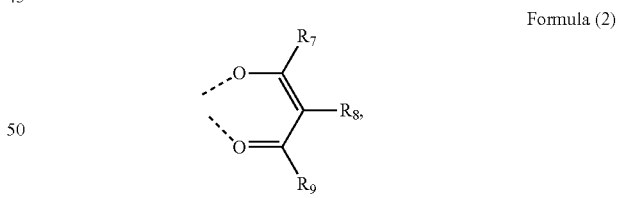

Formula (2)

wherein $R_1$ to $R_9$ are the same or different and each independently selected from the group consisting of a hydrogen atom, a substituted or unsubstituted alkyl group having 1 to 20 carbon atoms, a substituted or unsubstituted carbocyclic ring having 3 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

In some embodiments, L is selected from the following groups:

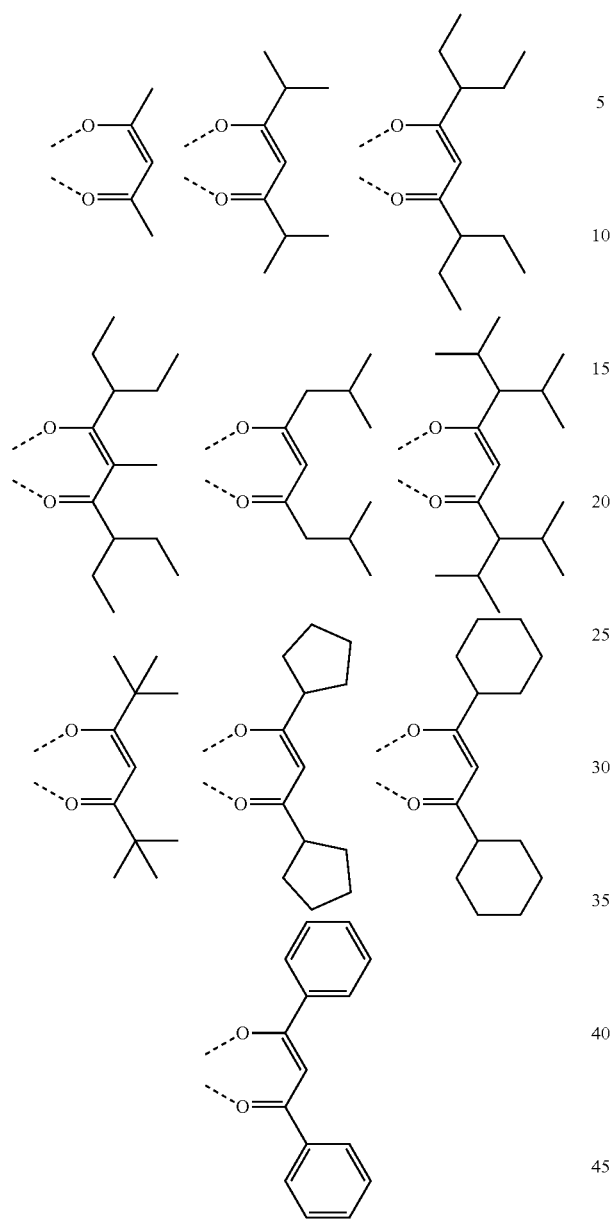
Preferably, the iridium complex is one of the following complexes:
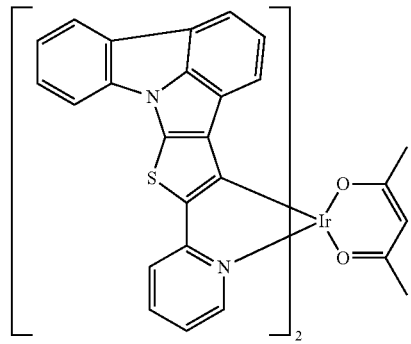
EX1
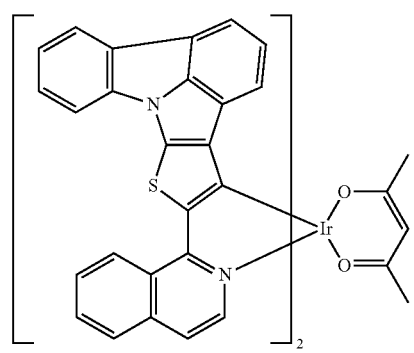
EX2
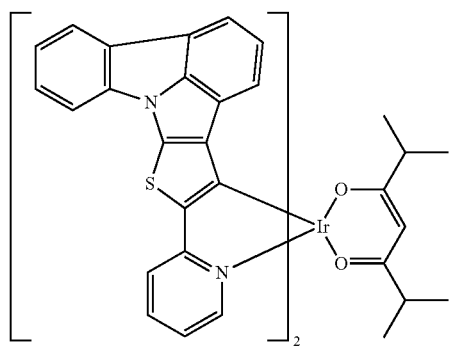
EX3
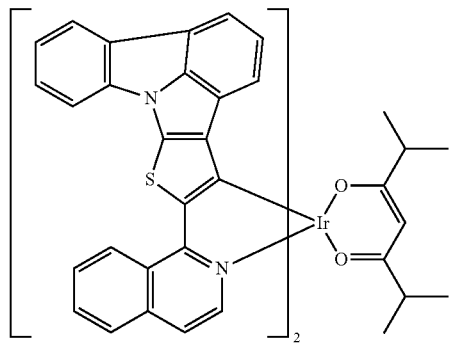
EX4
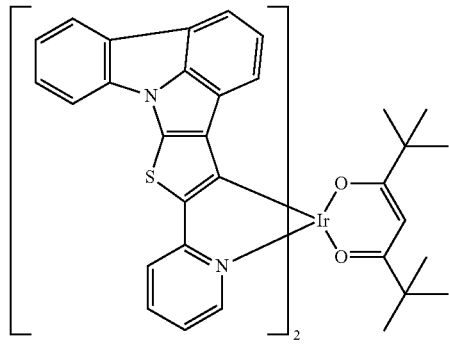
EX5

EX6
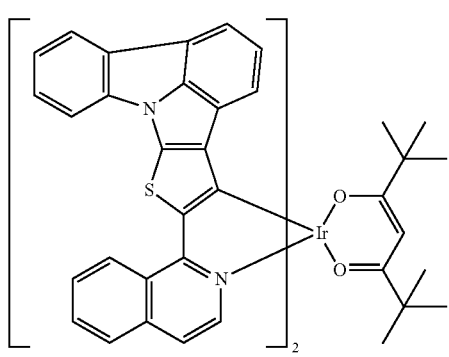
EX7
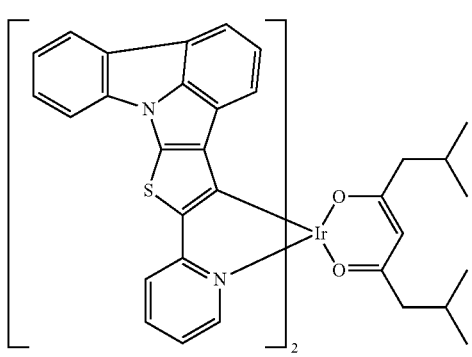
EX8
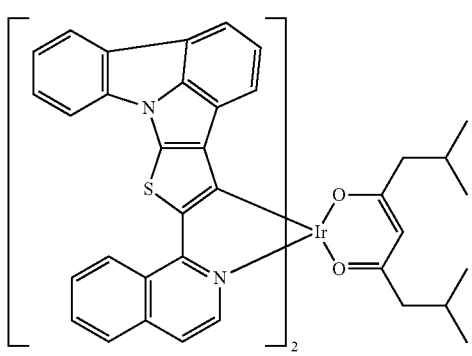
EX9
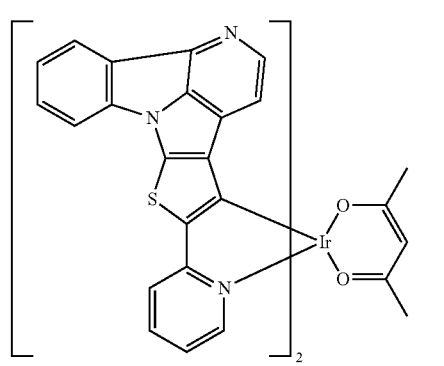
EX10
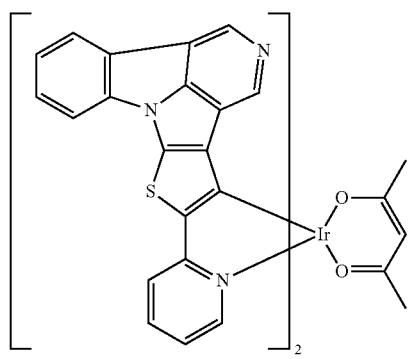
EX11
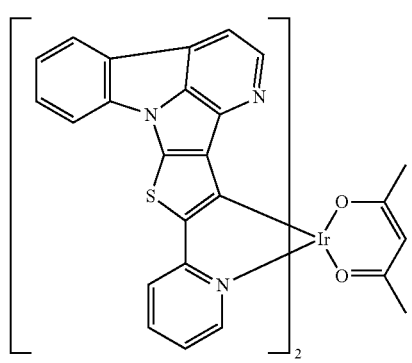
EX12
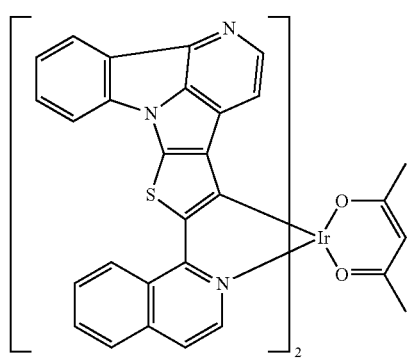
EX13
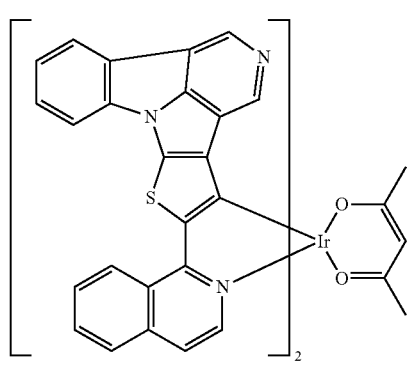

EX14
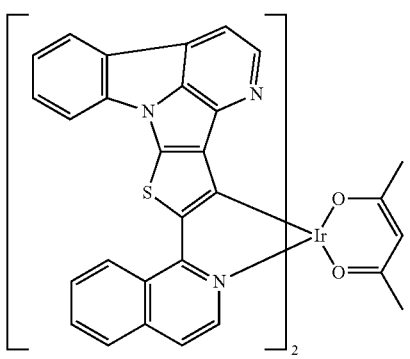
EX15
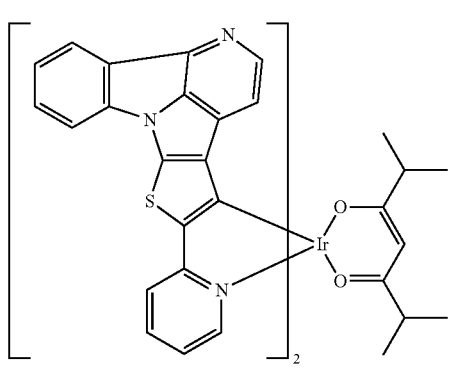
EX16
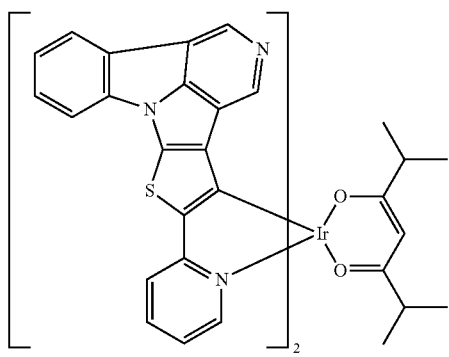
EX17
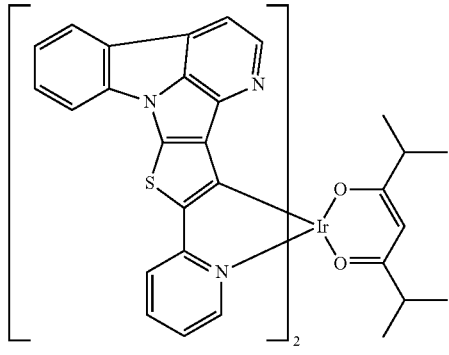
EX18
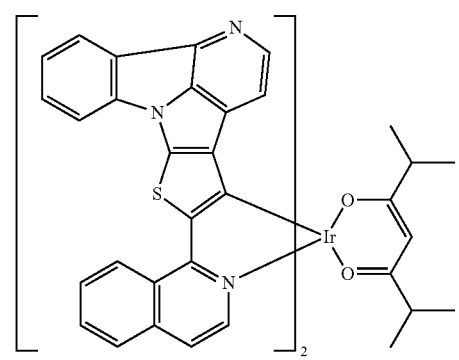
EX19
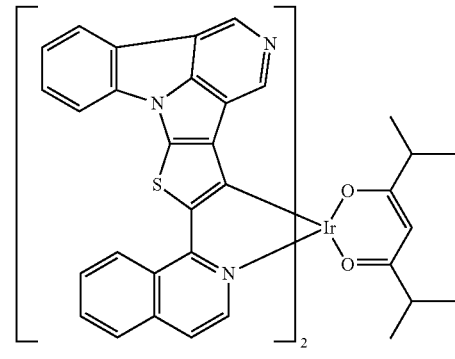
EX20
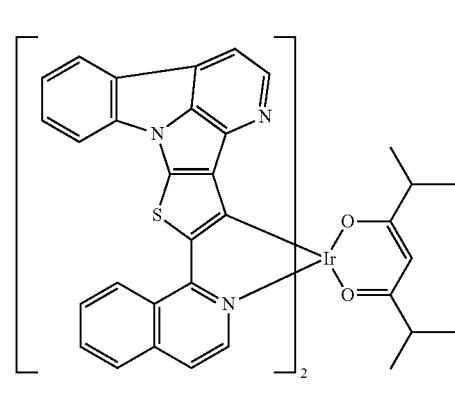
EX21
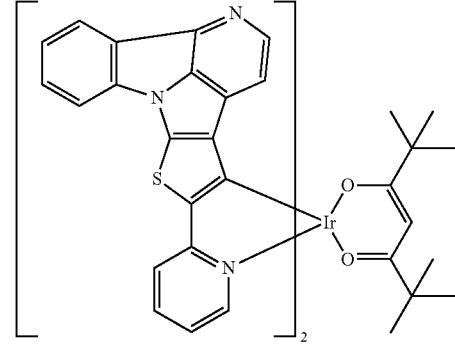

EX22
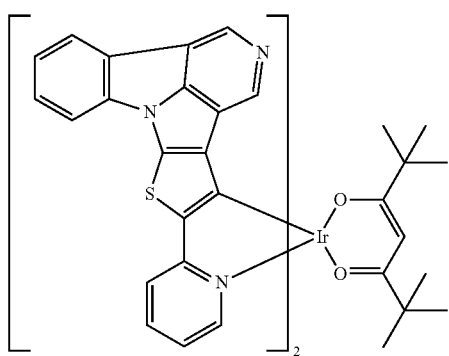
EX26
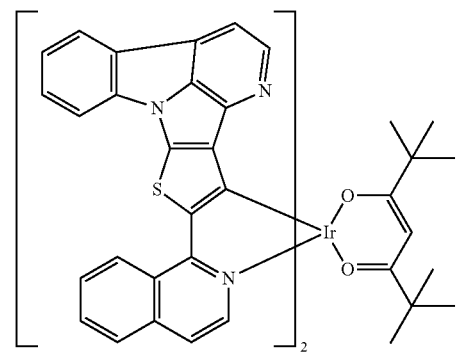
EX23
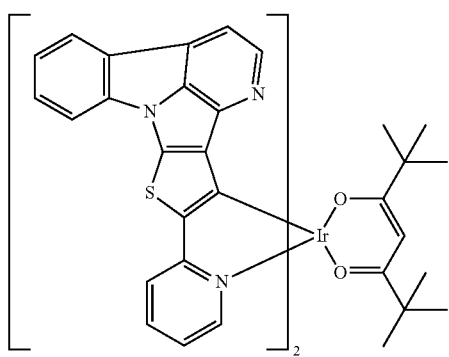
EX27
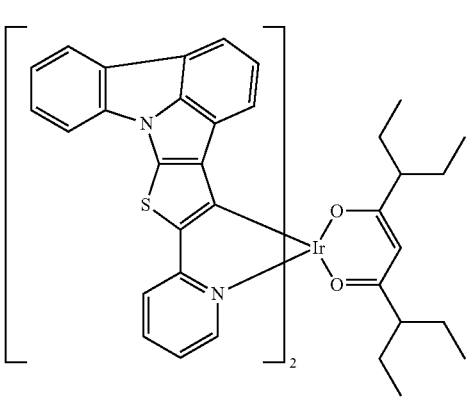
EX24
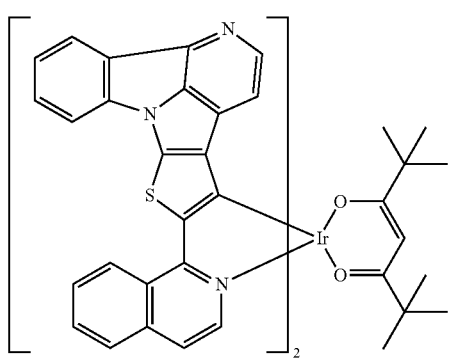
EX28
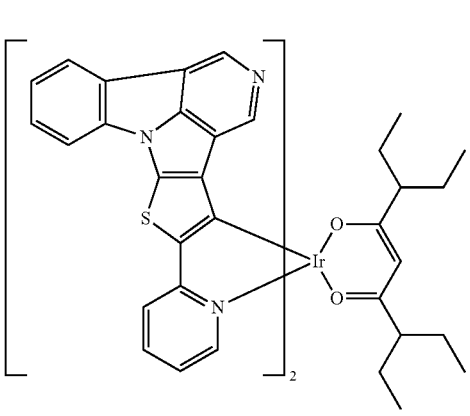
EX25
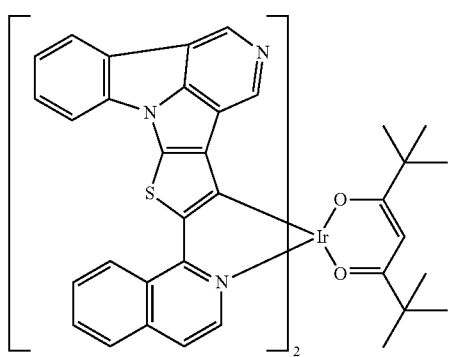
EX29
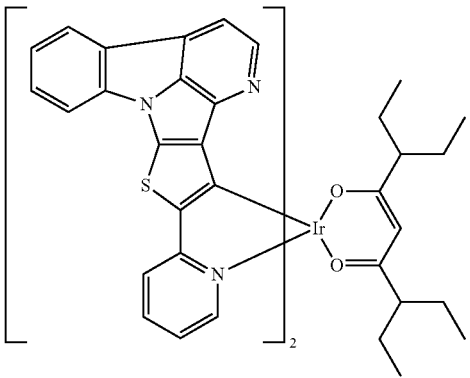

EX30
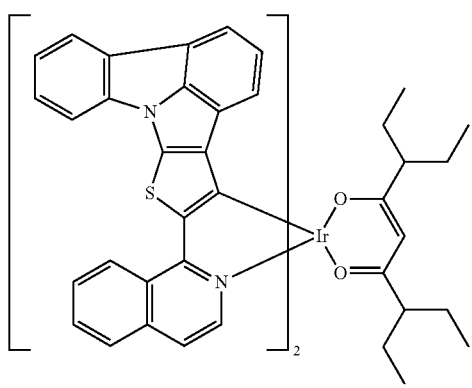
EX31
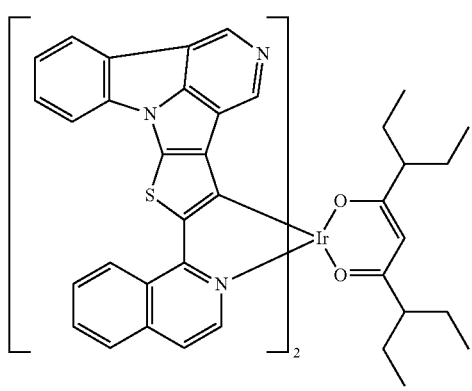
EX32
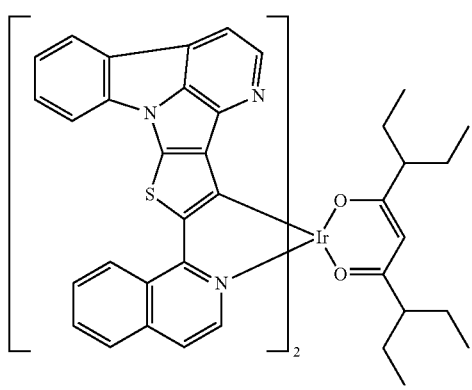
EX33
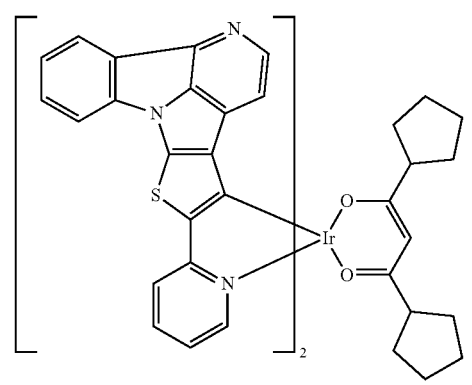
EX34
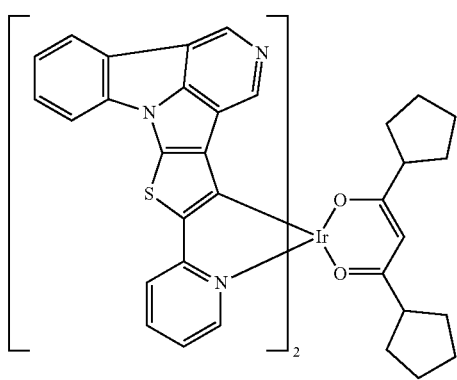
EX35
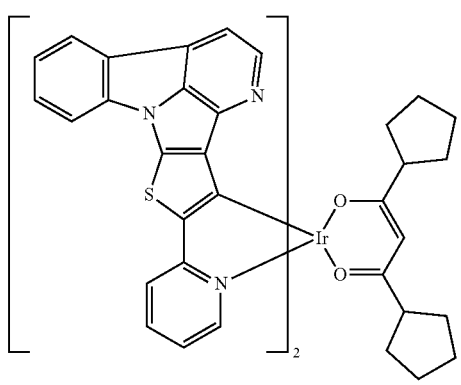
EX36
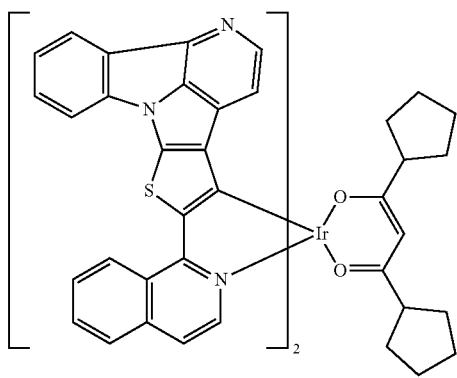
EX37
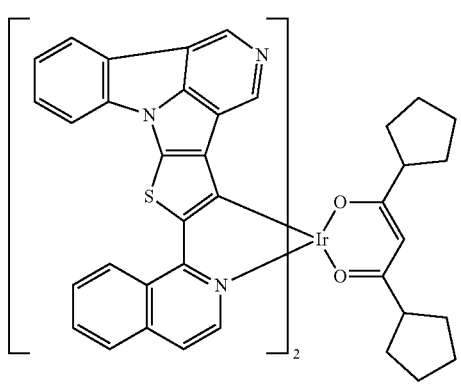

EX38
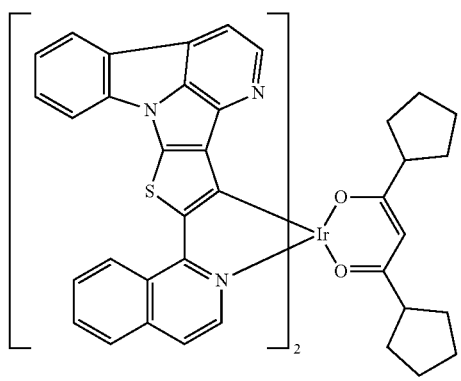
EX39
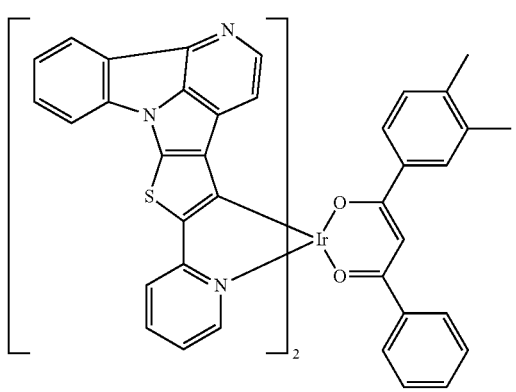
EX40
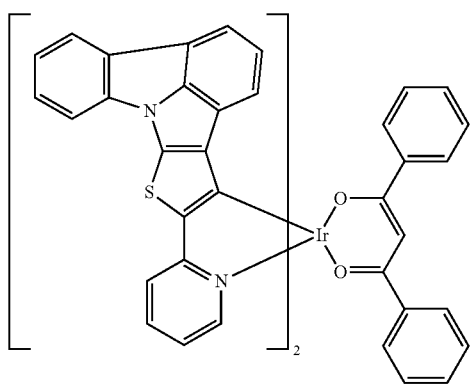
EX41
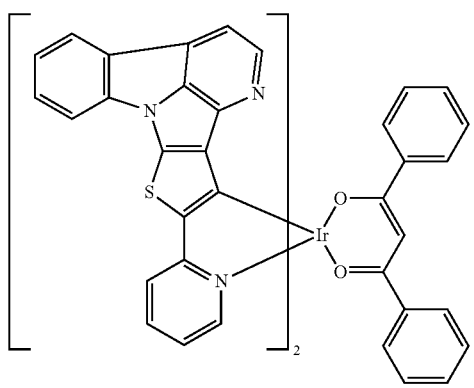
EX42
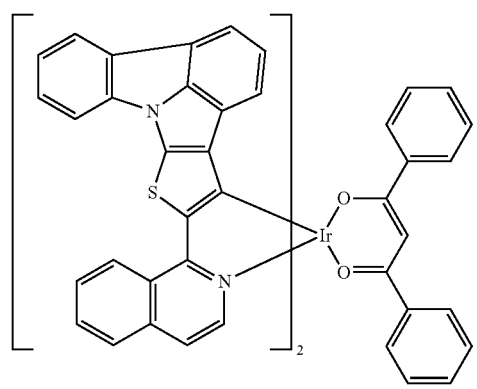
EX43
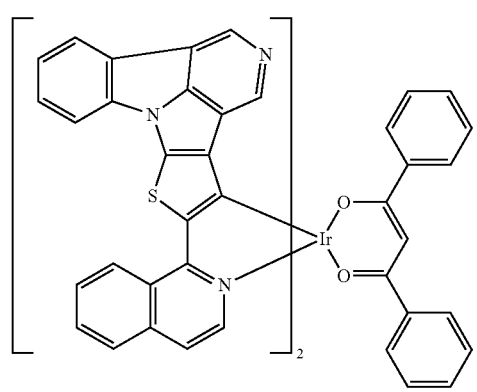
EX44
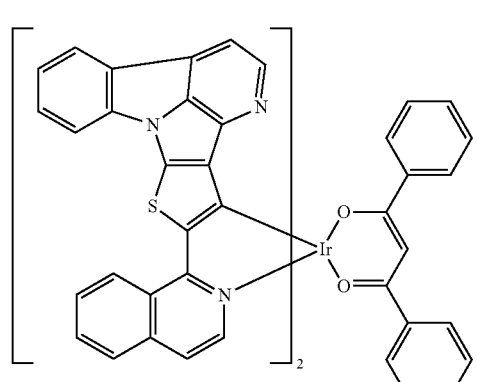
EX45
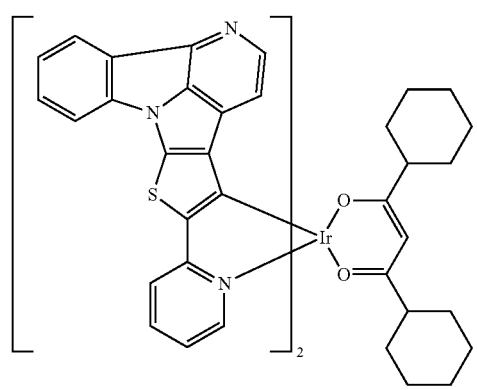

EX46
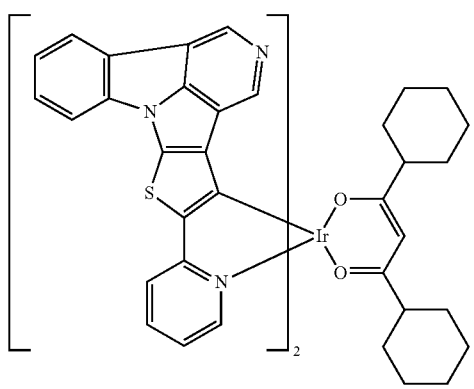
EX47
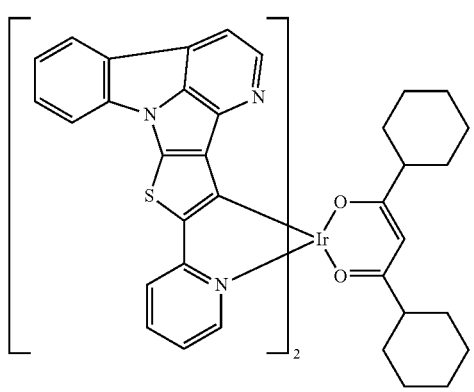
EX48
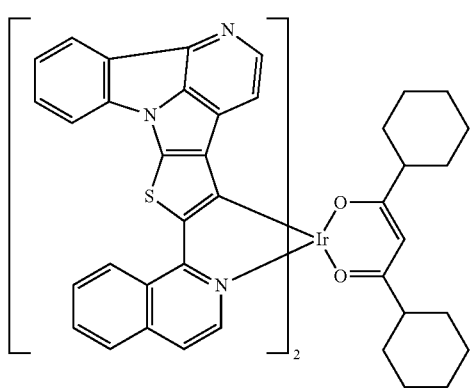
EX49
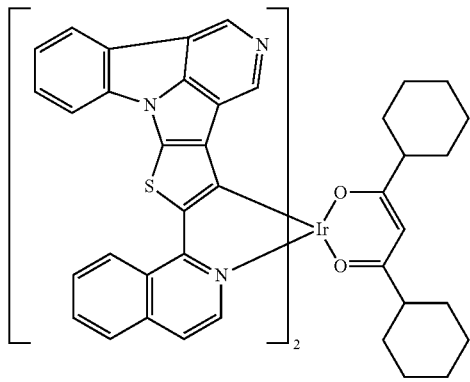
EX50
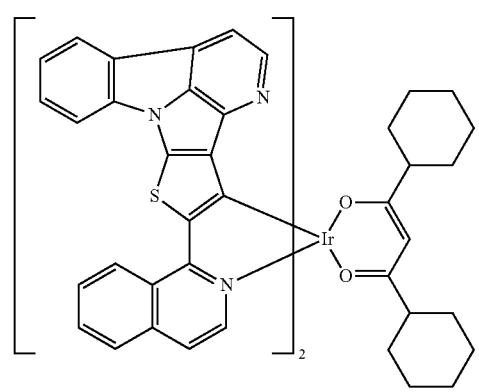
EX51
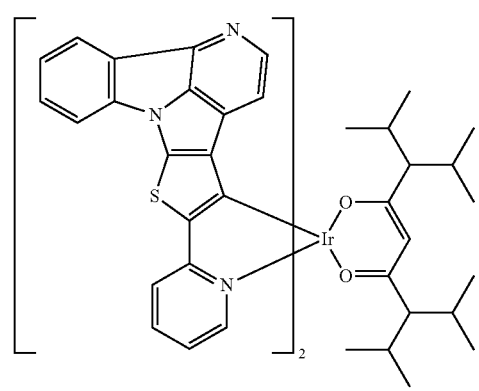
EX52
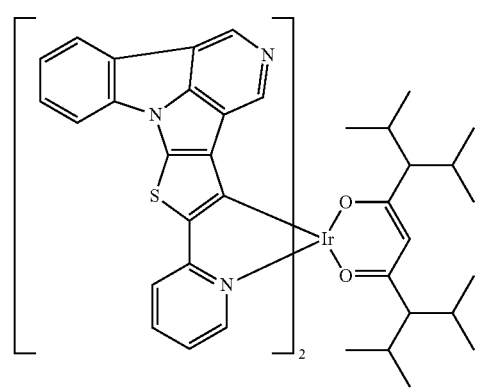
EX53
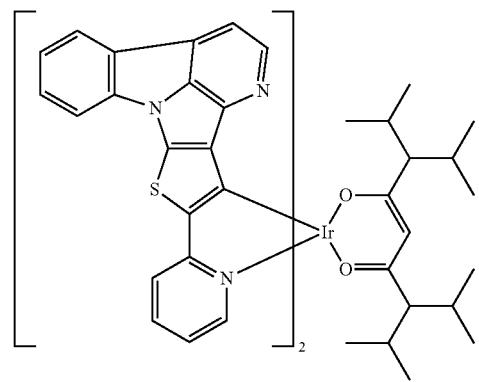

EX54
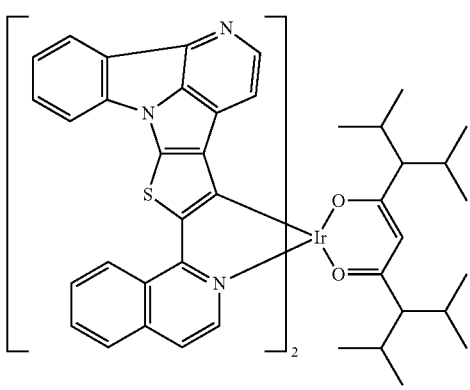
EX55
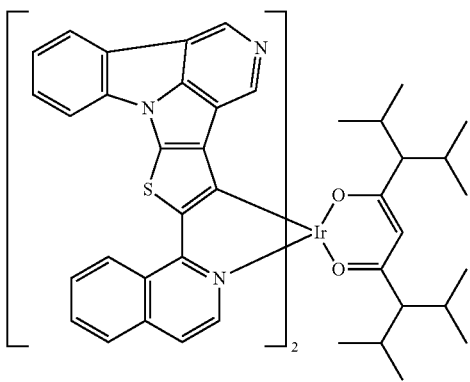
EX56
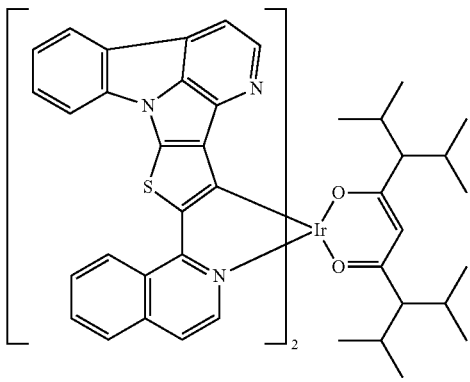
EX57
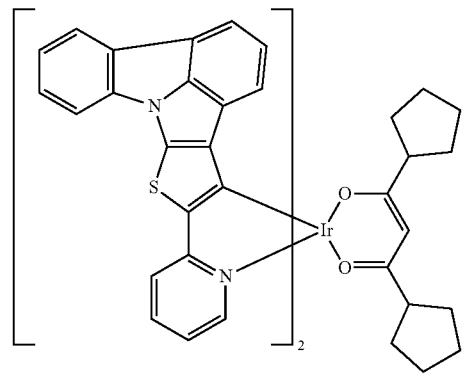
EX58
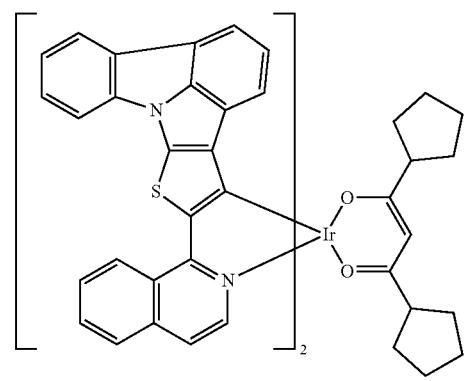
EX59
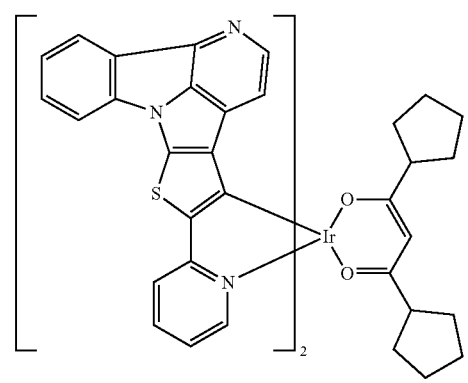
EX60
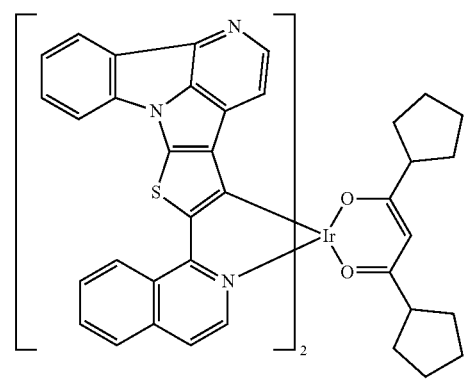
EX61
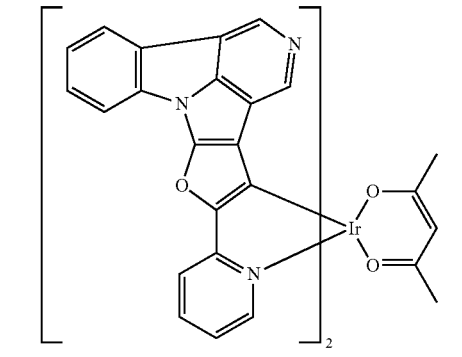

EX62
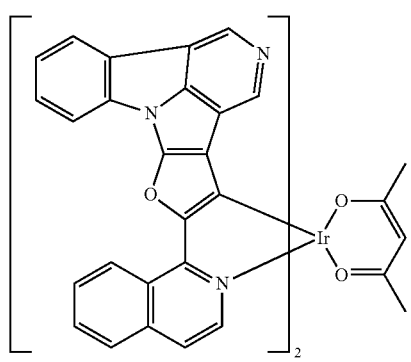
EX63
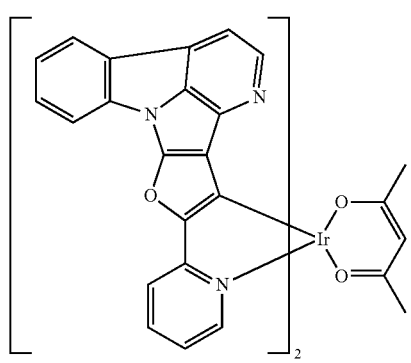
EX64
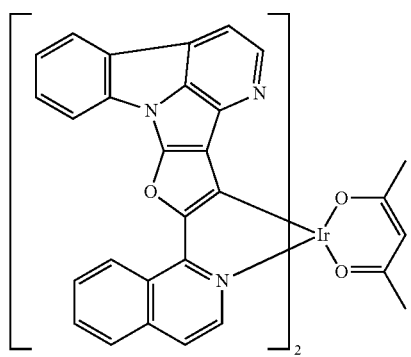
EX65
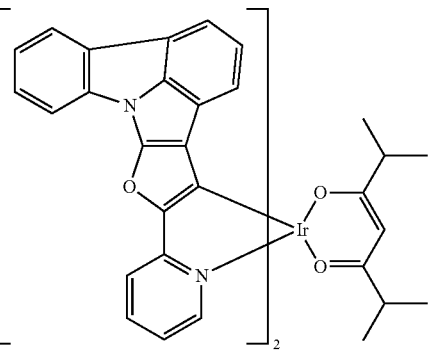
EX66
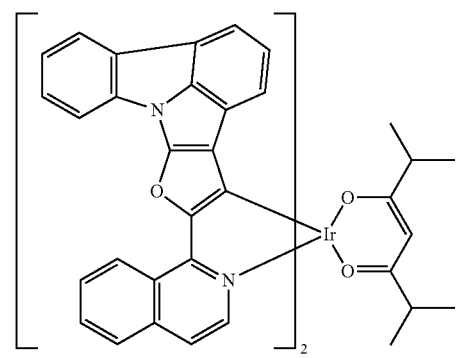
EX67
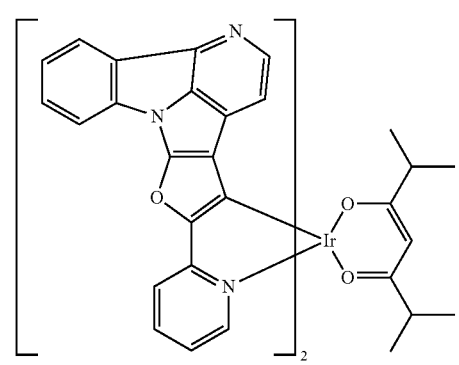
EX68
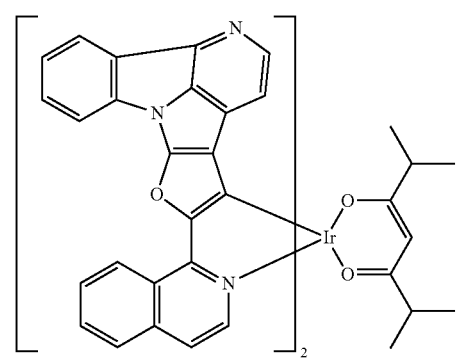
EX69
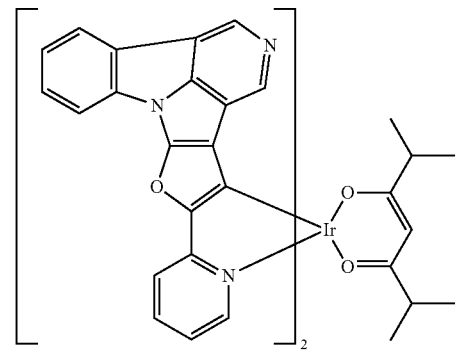

EX70
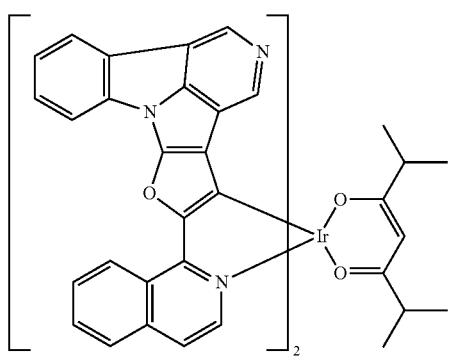
EX74
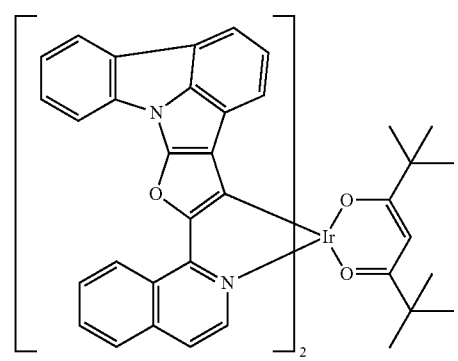
EX71
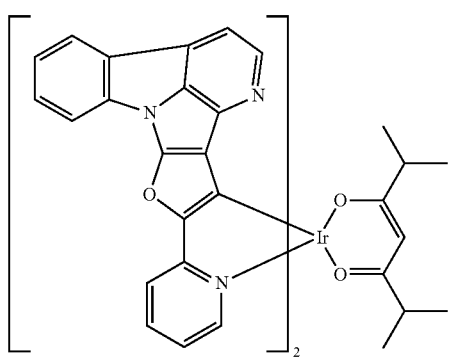
EX75
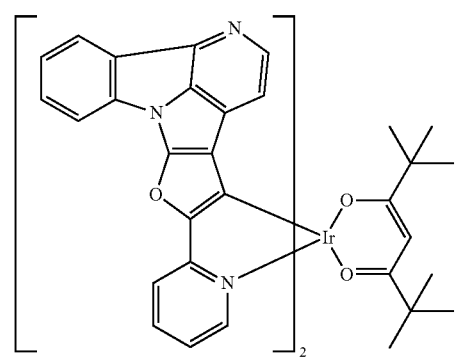
EX72
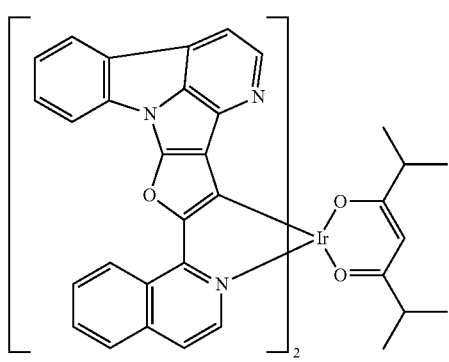
EX76
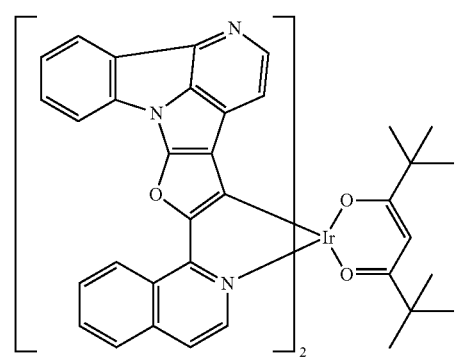
EX73
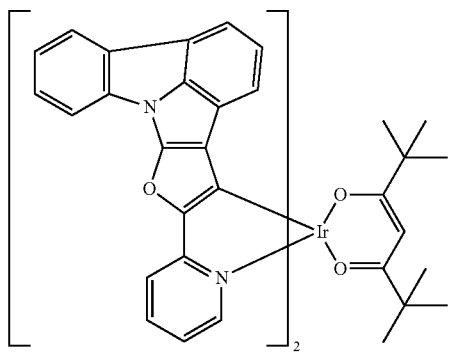
EX77
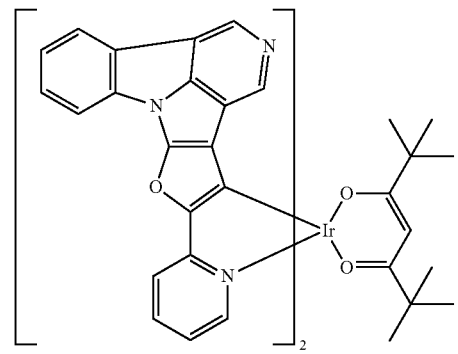

EX78
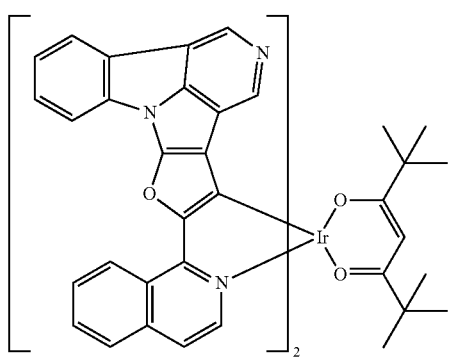
EX79
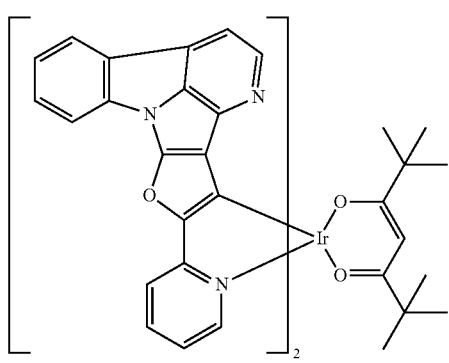
EX80
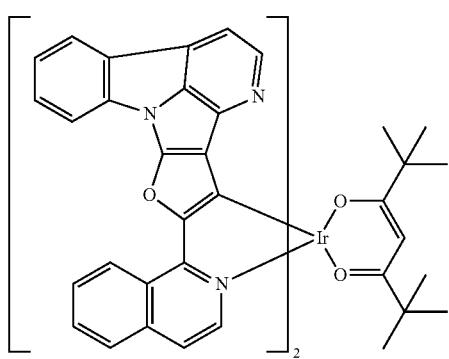
EX81
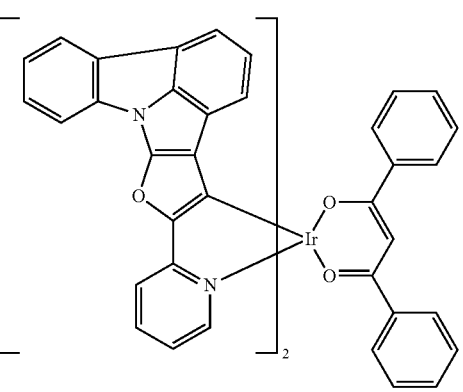
EX82
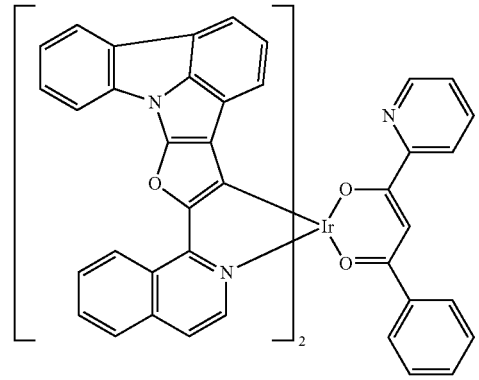
EX83
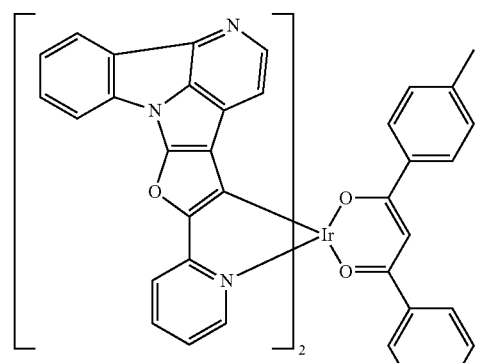
EX84
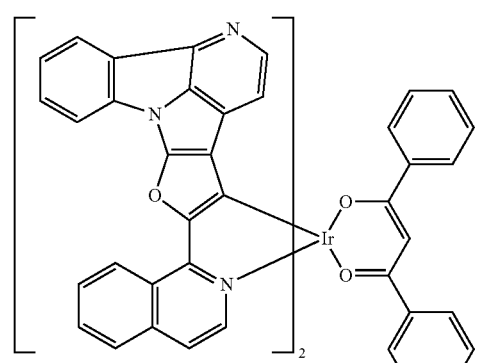
EX85
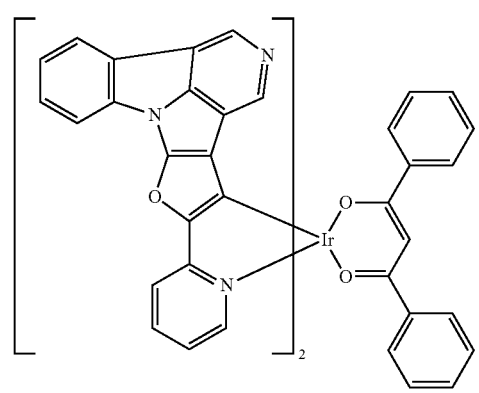

-continued
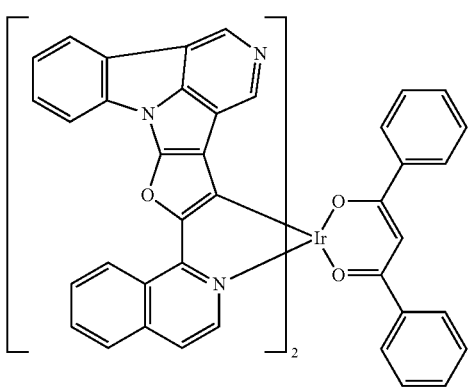
EX86
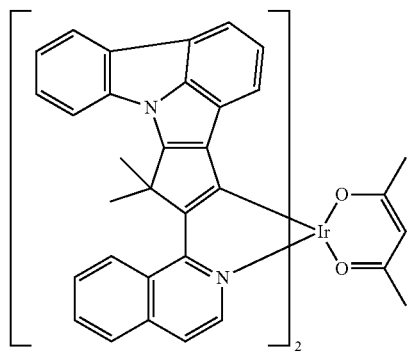
EX90
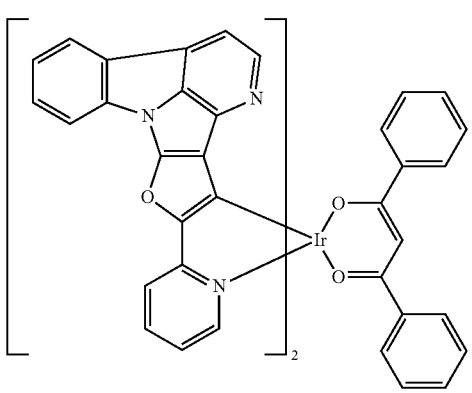
EX87
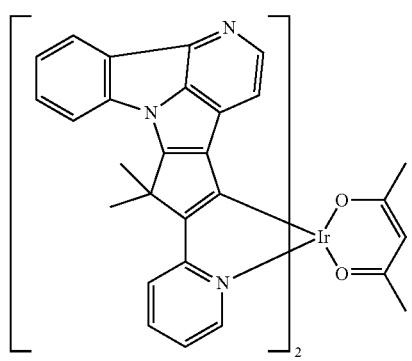
EX91
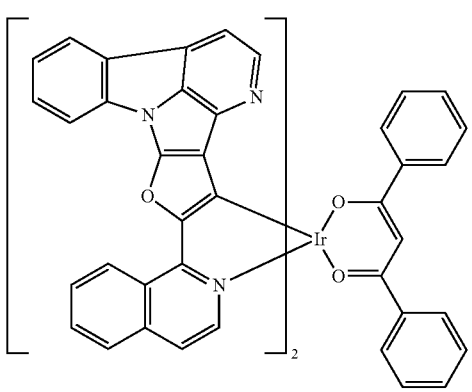
EX88
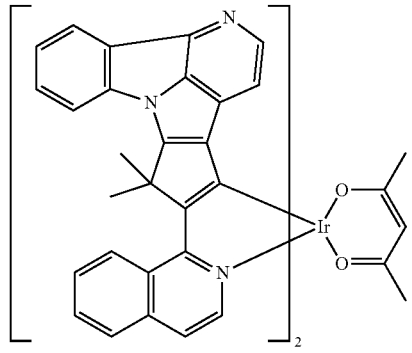
EX92
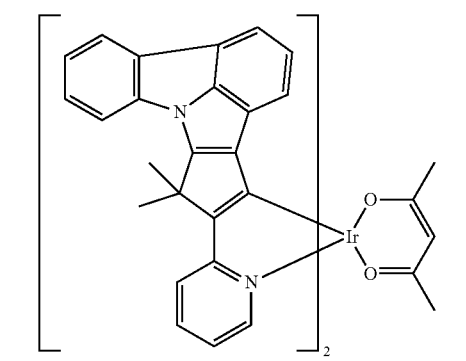
EX89
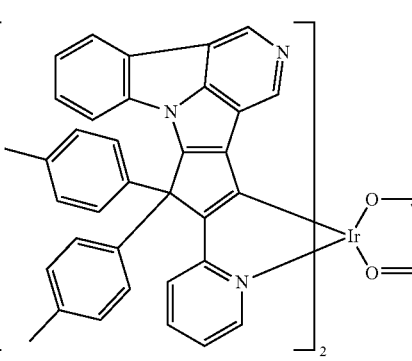
EX93

EX94
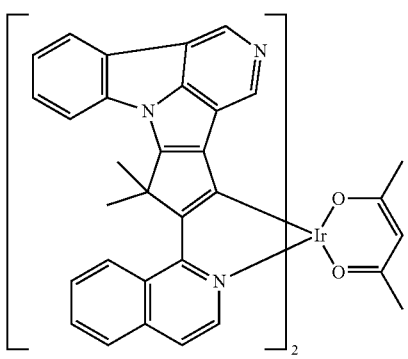
EX98
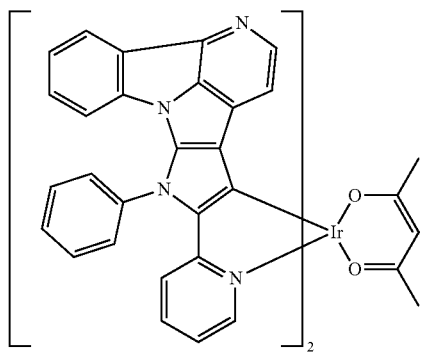
EX95
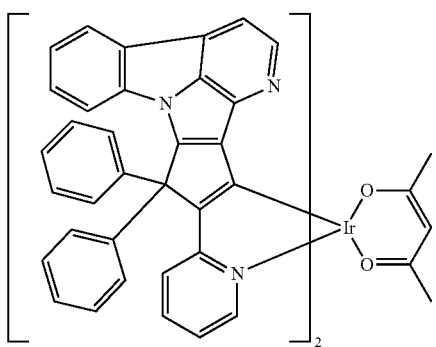
EX99
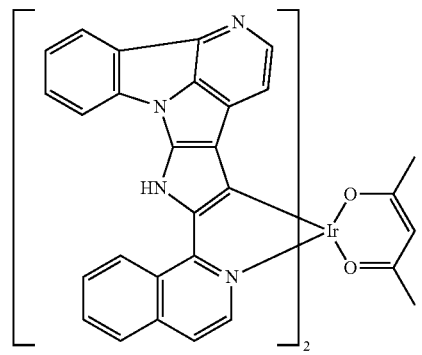
EX96
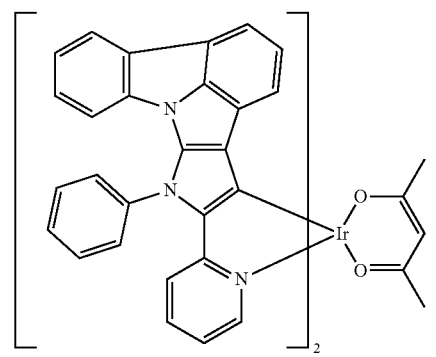
EX100
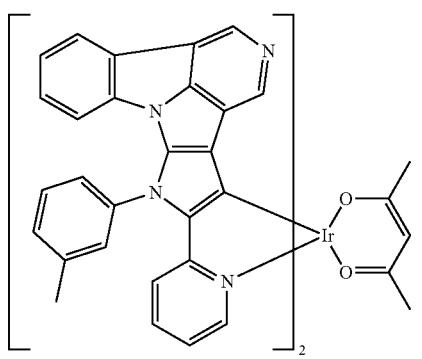
EX97
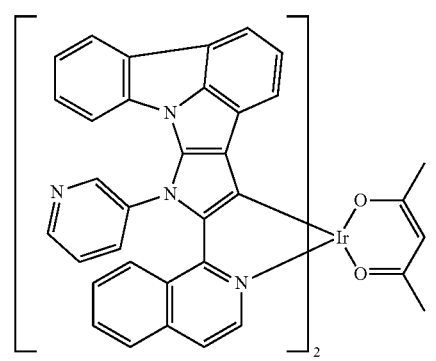
EX101
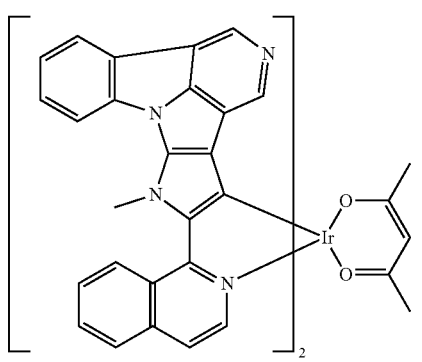

EX102
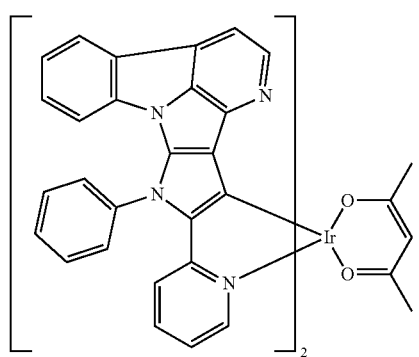
EX103
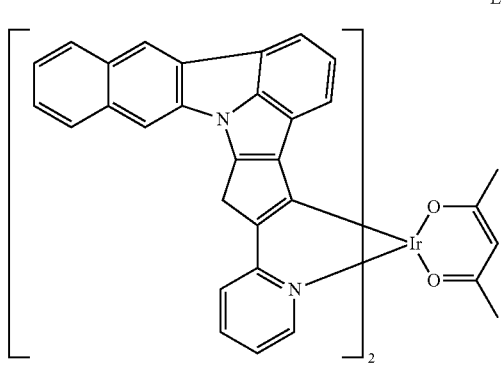
EX104
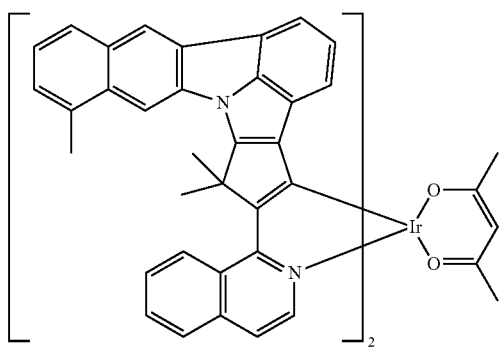
EX105
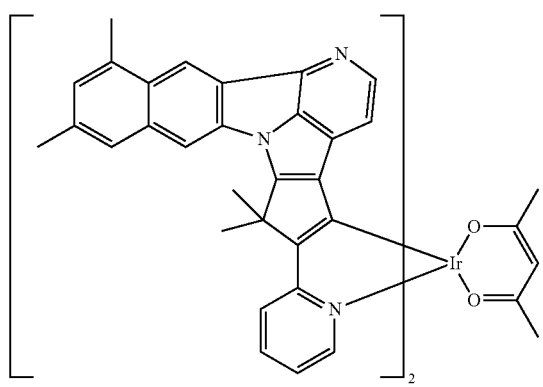
EX106
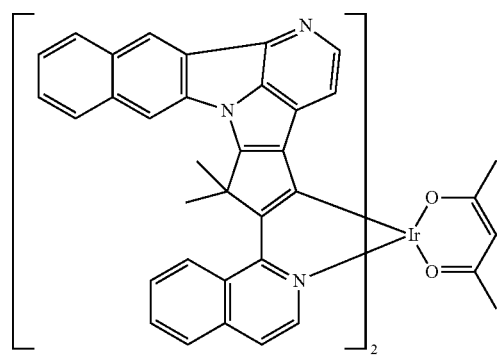
EX107
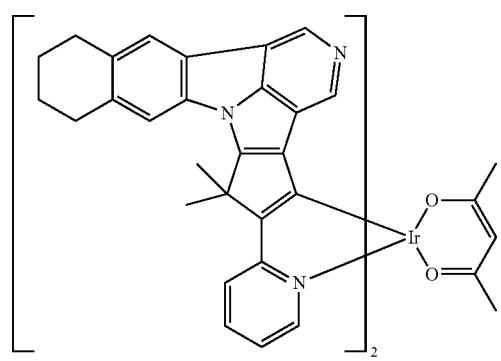
EX108
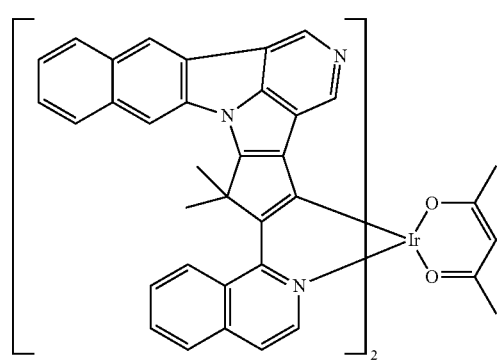
EX109
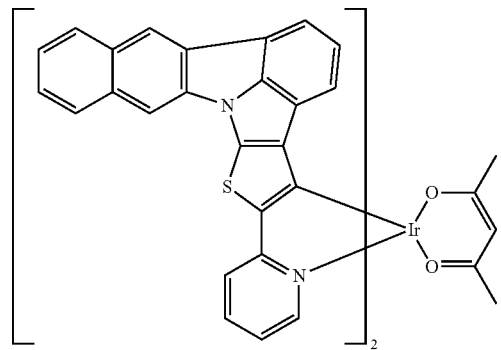

EX110
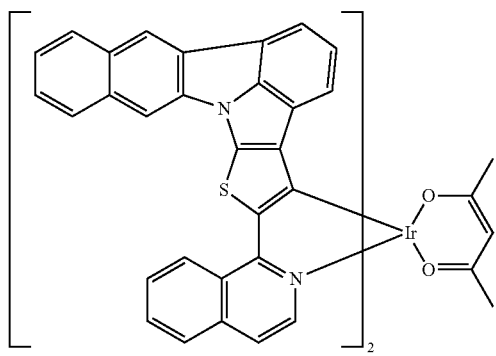
EX114
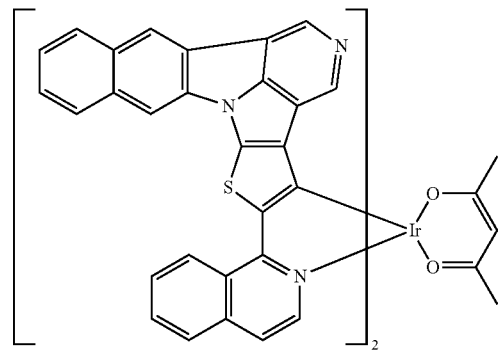
EX111
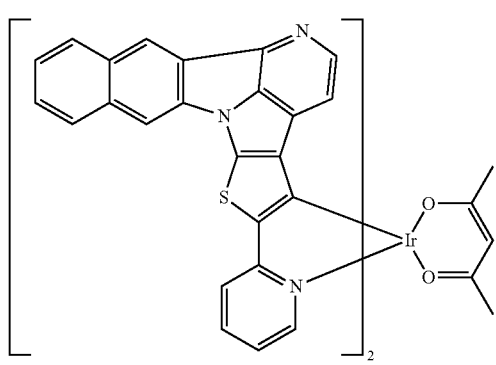
EX115
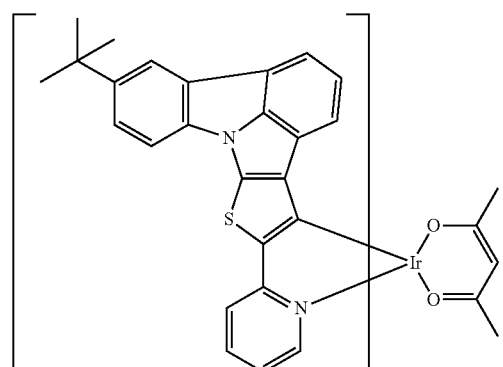
EX112
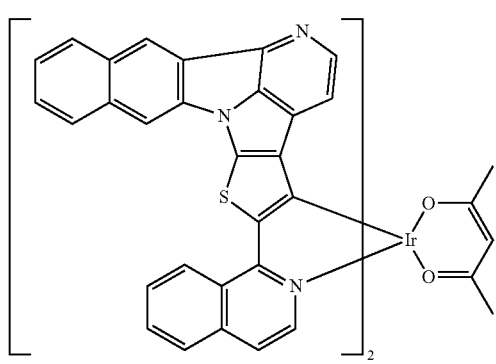
EX116
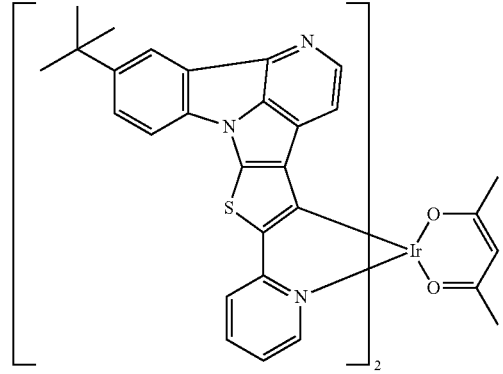
EX113
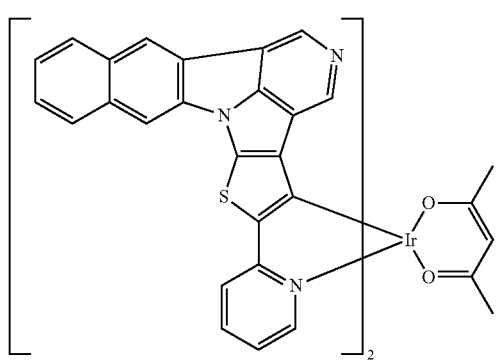
EX117

EX118
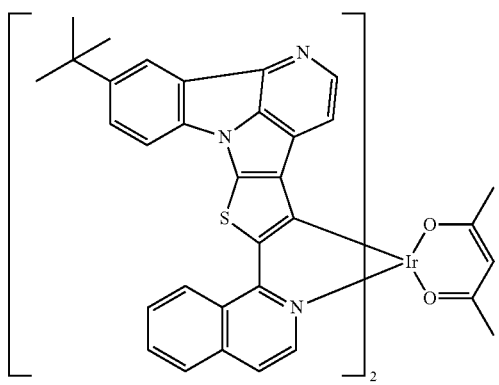
EX119
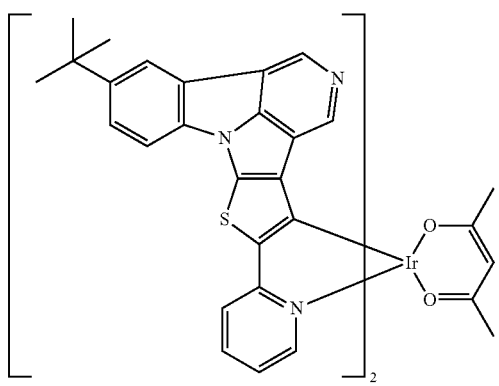
EX120
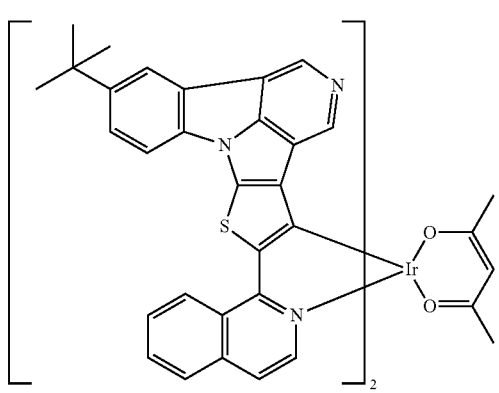
EX121
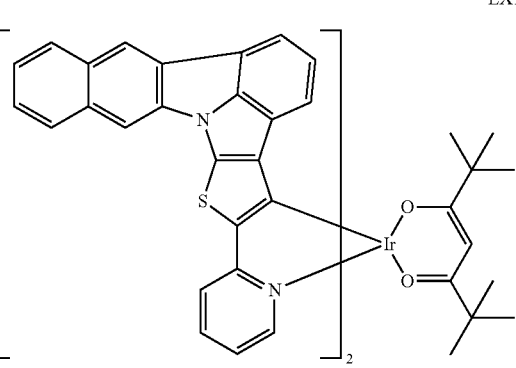
EX122
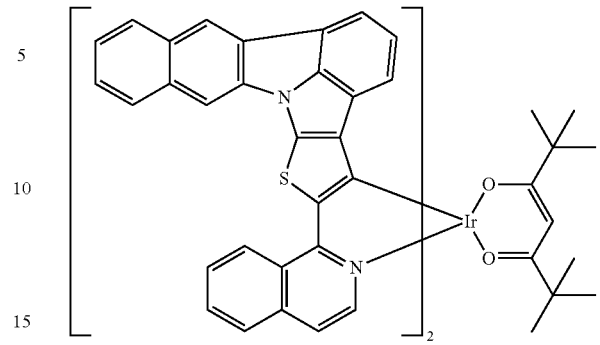
EX123
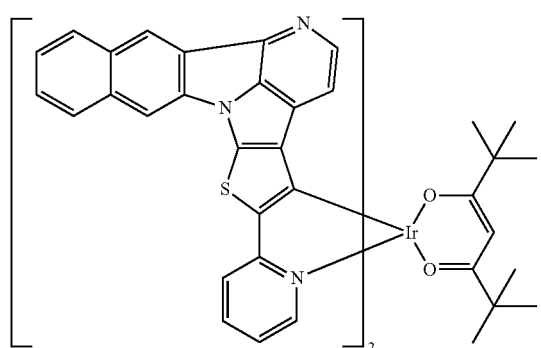
EX124
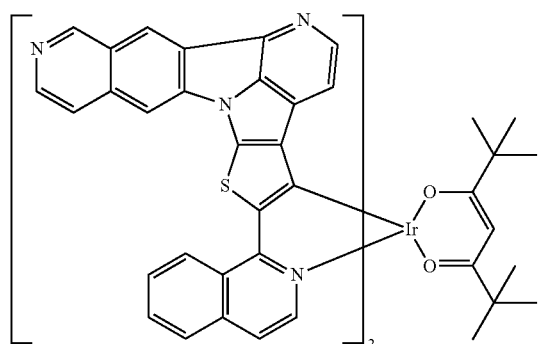
EX125
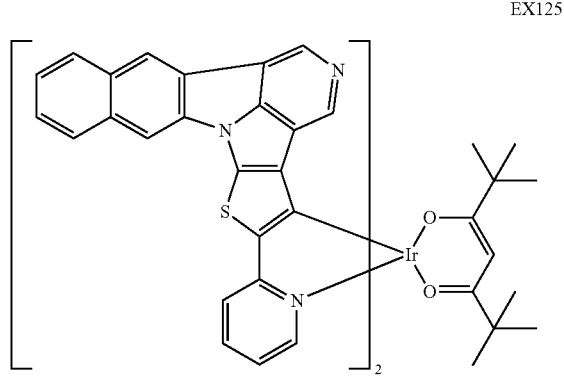

EX126
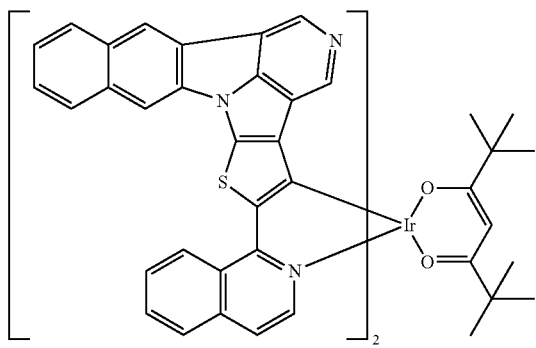
EX127
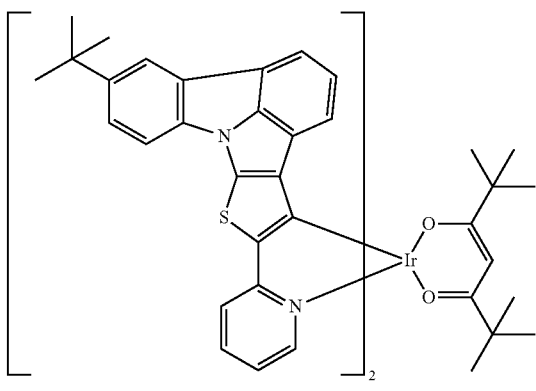
EX128
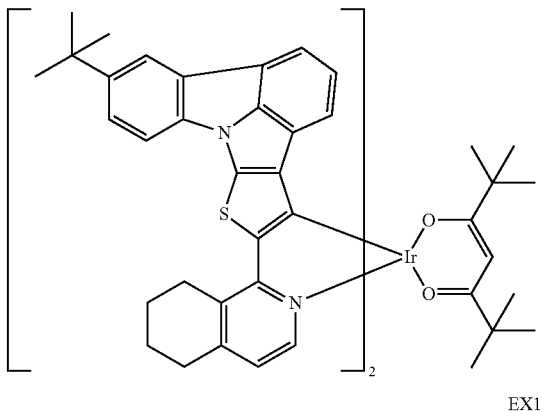
EX129
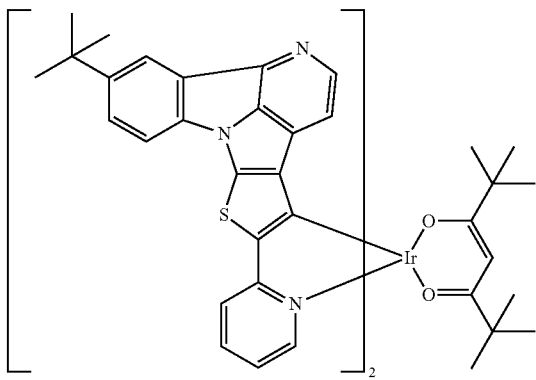
EX130
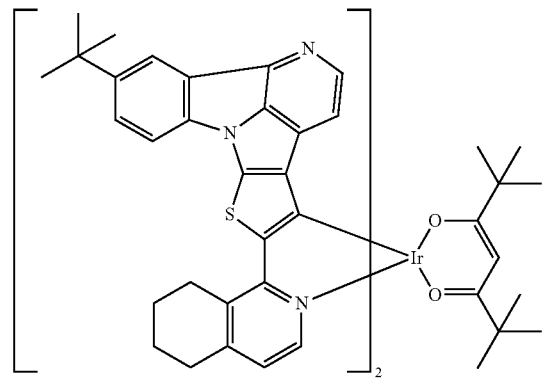
EX131
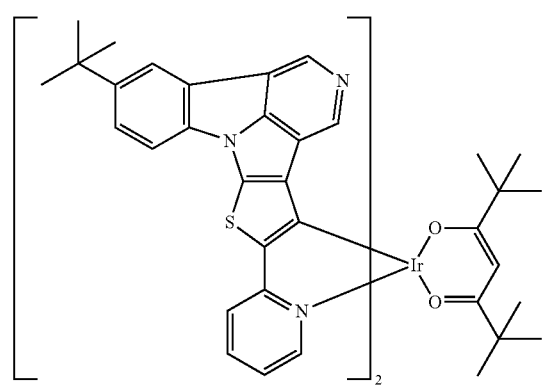
EX132
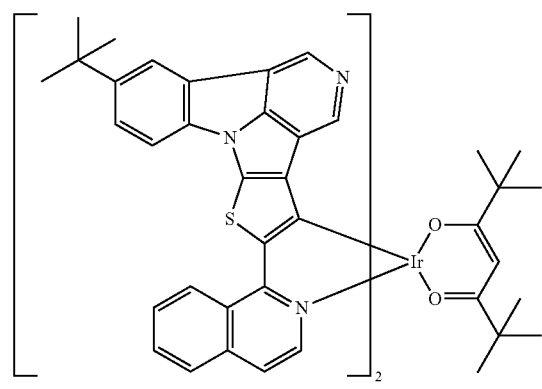
EX133
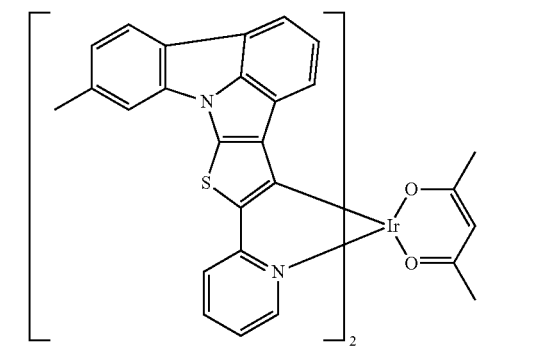

EX134
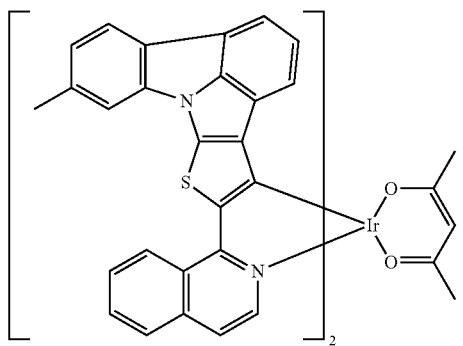
EX135
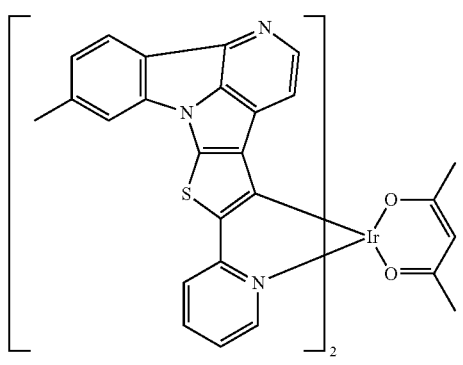
EX136
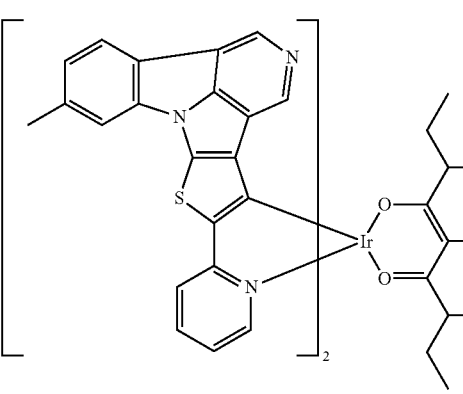
EX137
EX138
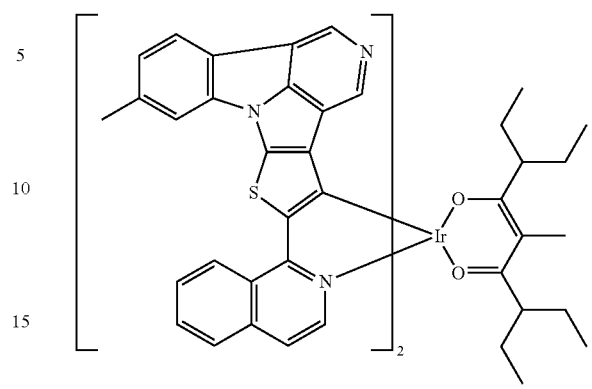
EX139
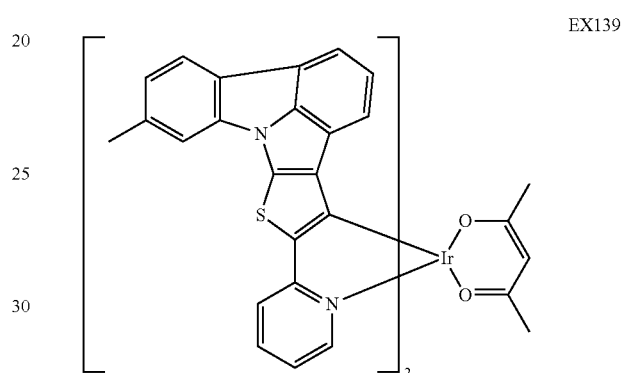
EX140
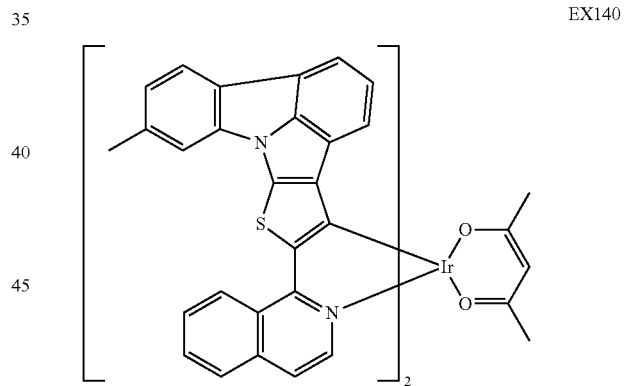
EX141
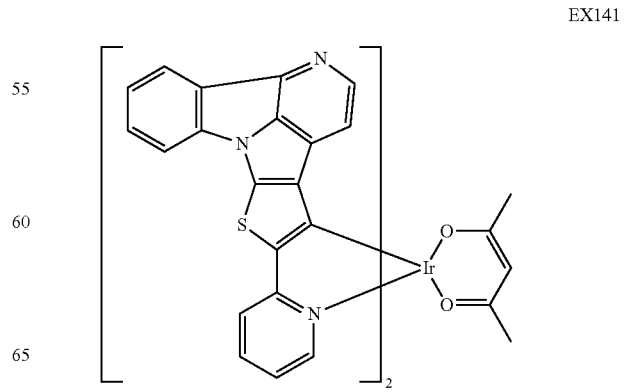

EX142
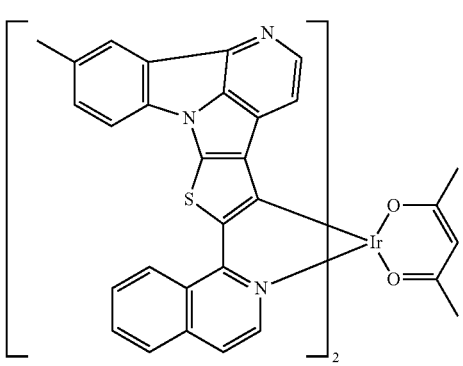
EX143
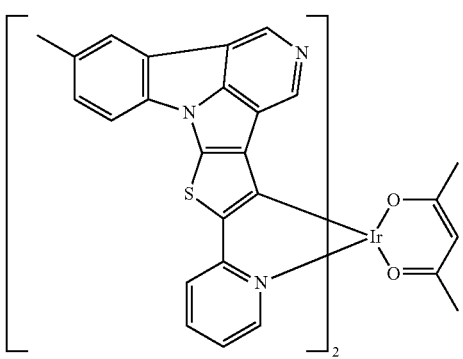
EX144
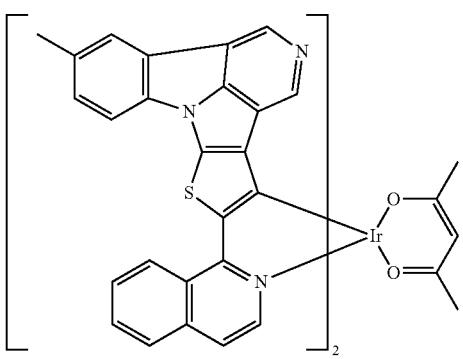
EX145
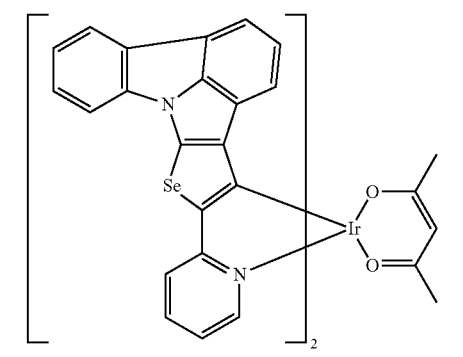
EX146
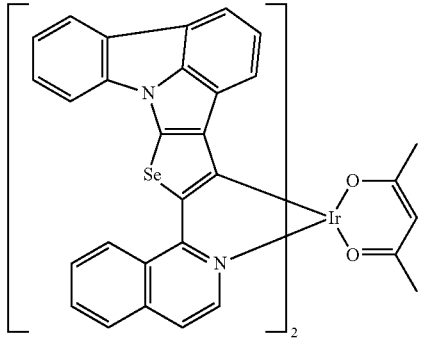
EX147
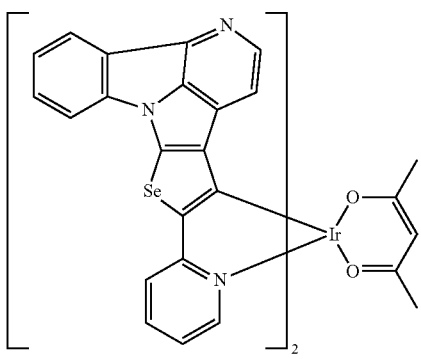
EX148
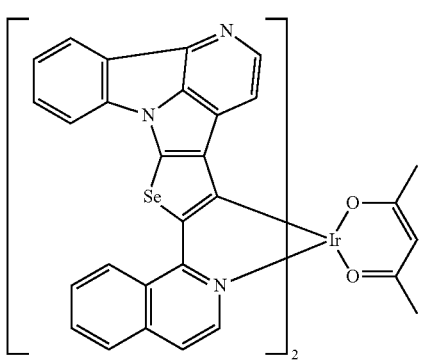
EX149
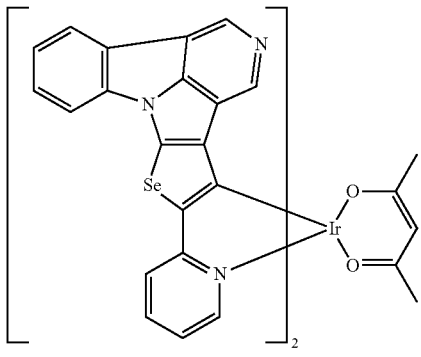

EX150
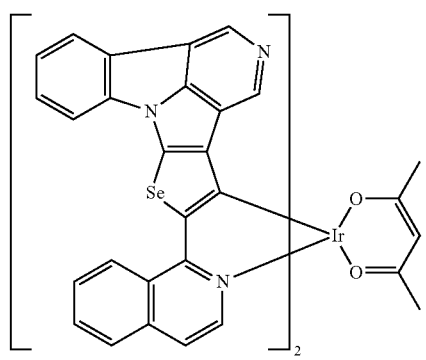
EX154
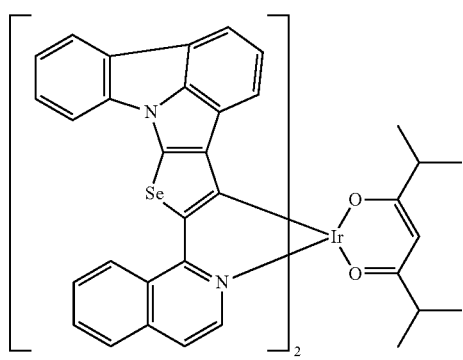
EX151
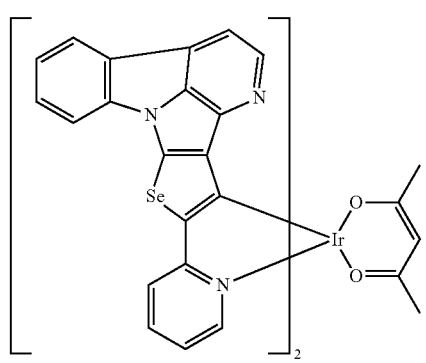
EX155
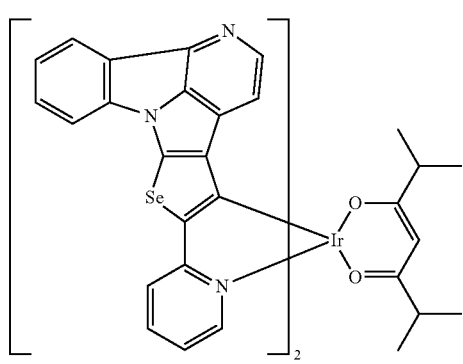
EX152
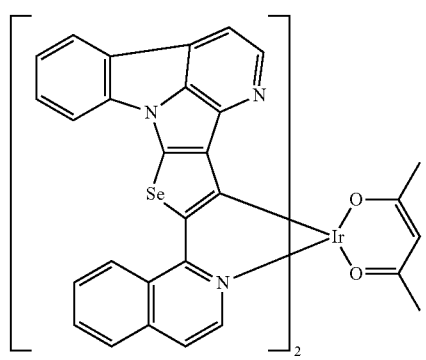
EX156
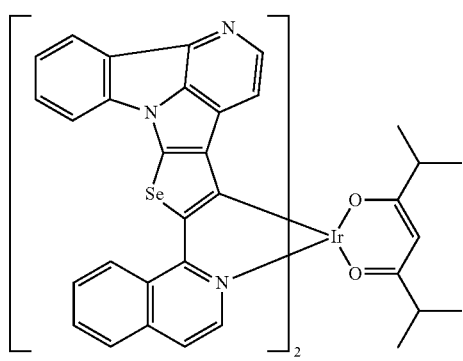
EX153
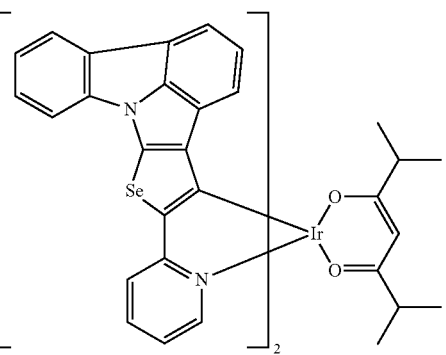
EX157
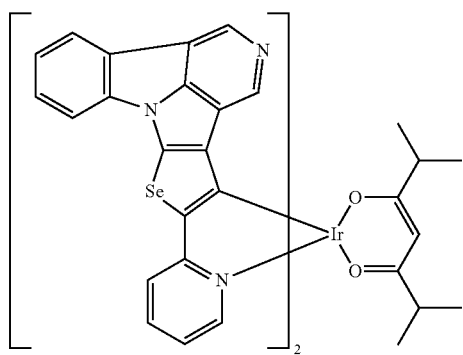

EX158
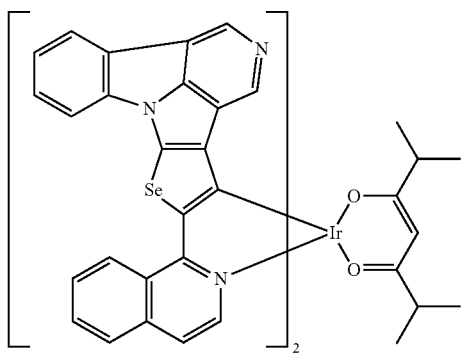
EX162
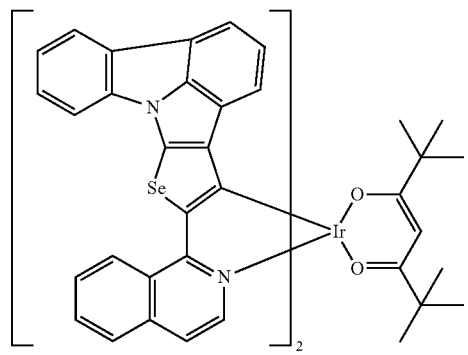
EX159
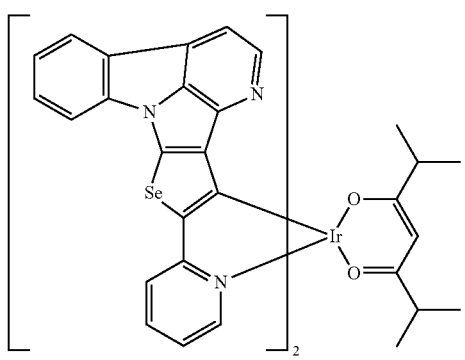
EX163
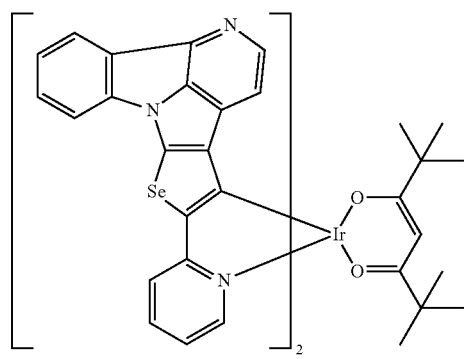
EX160
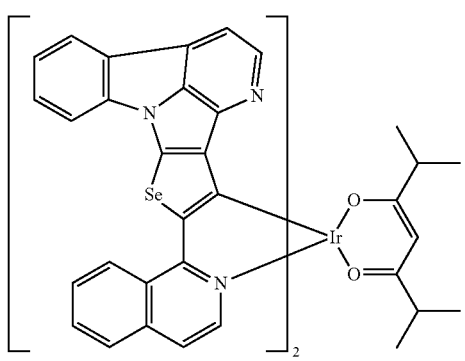
EX164
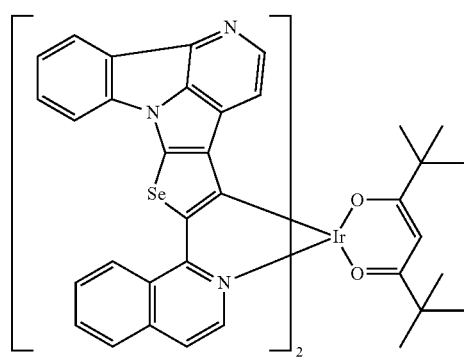
EX161
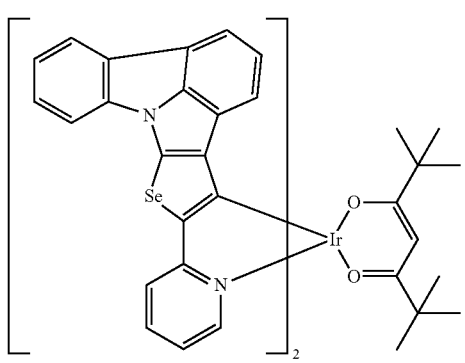
EX165
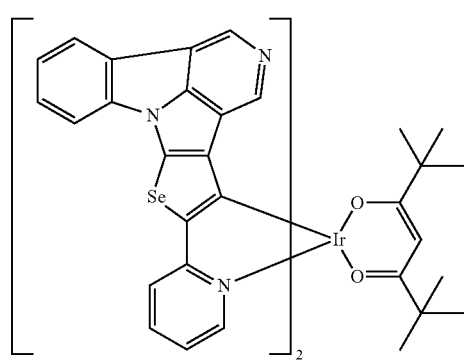

EX166
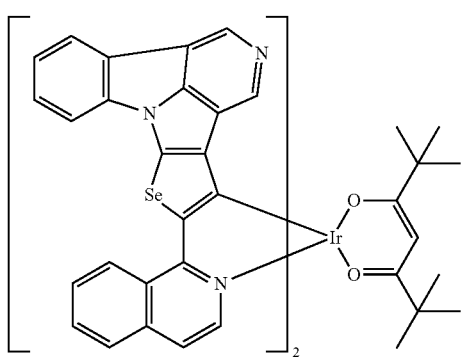
EX167
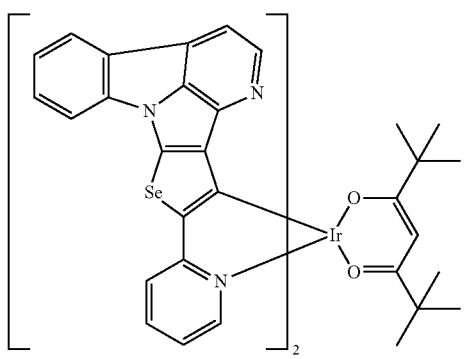
EX168
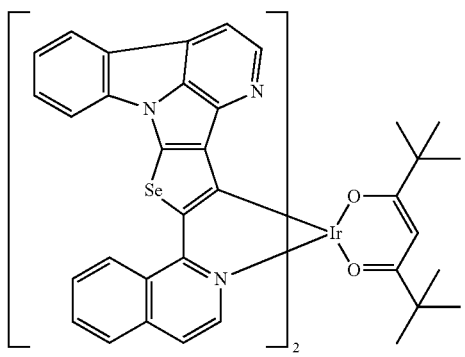
EX169
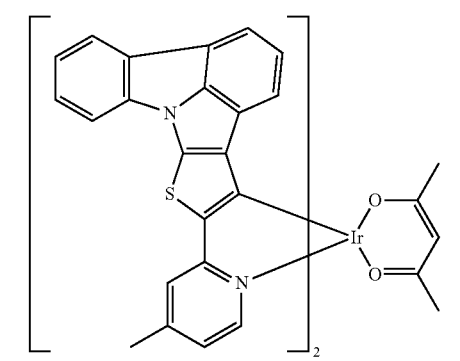
EX170
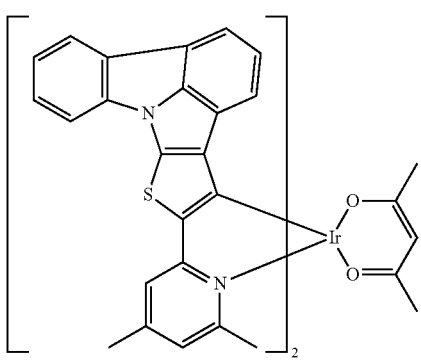
EX171
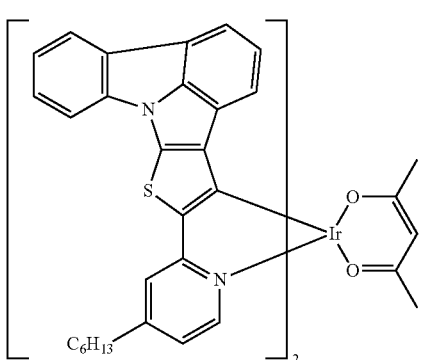
EX172
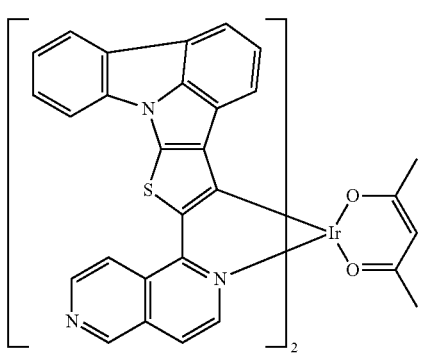
EX173
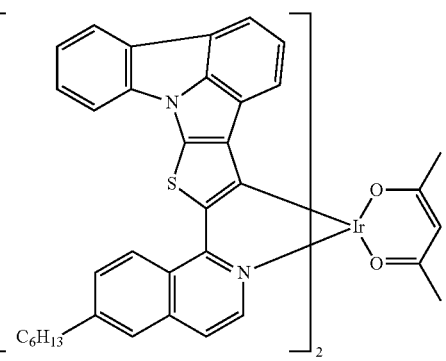

-continued
EX174
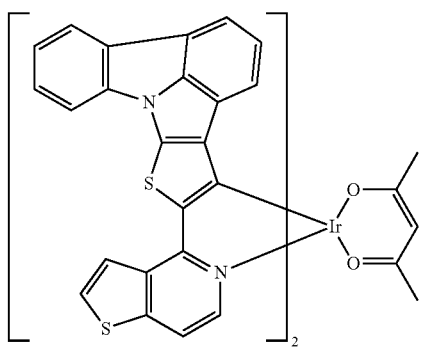
EX175
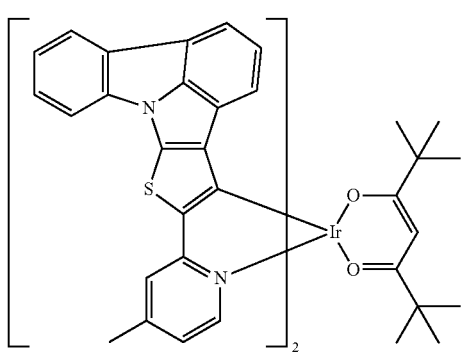
EX176
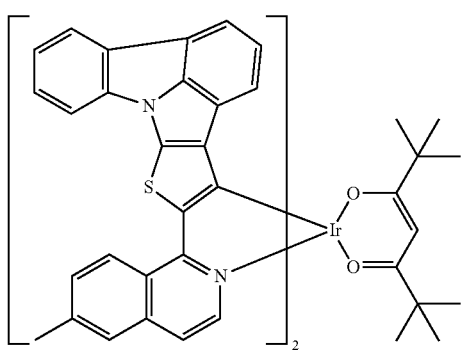
EX177
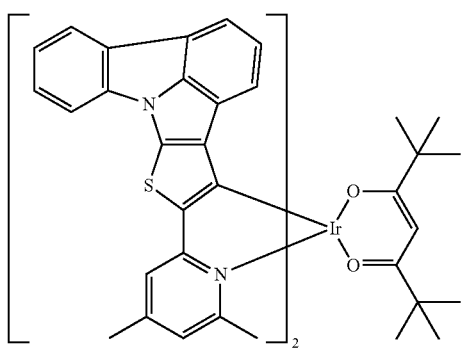
-continued
EX178
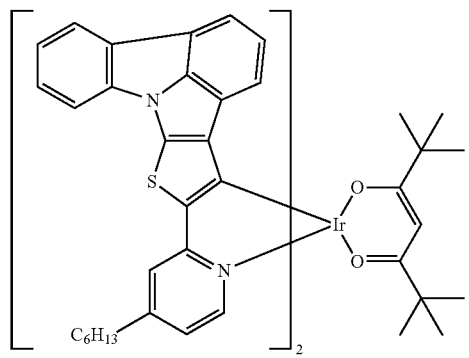
EX179
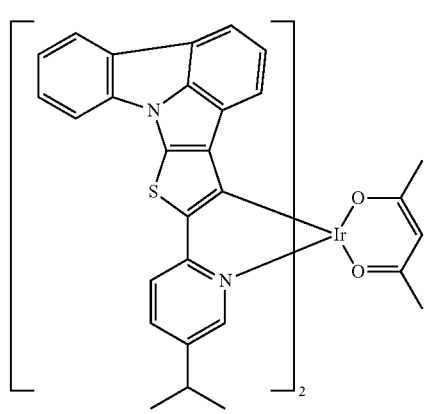
EX180
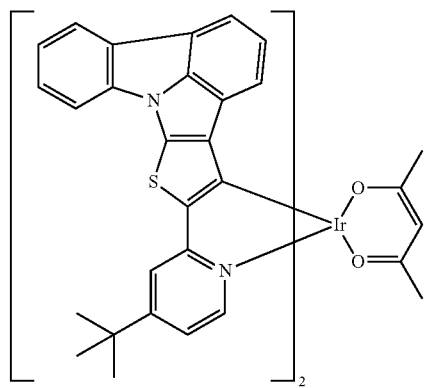
EX181
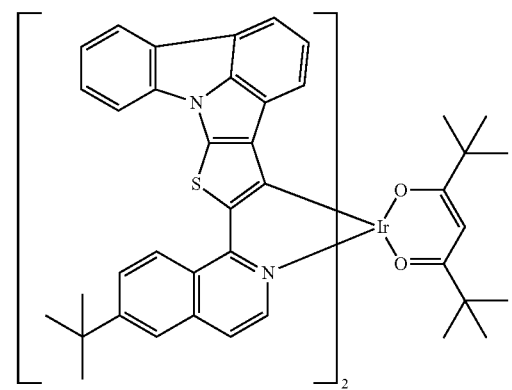

EX182
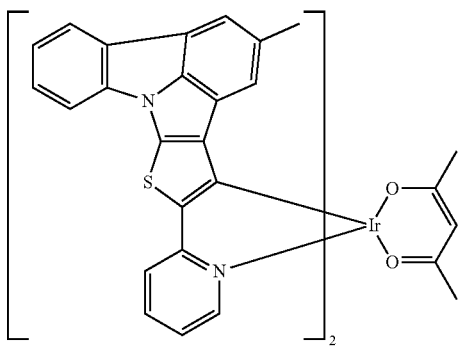
EX186
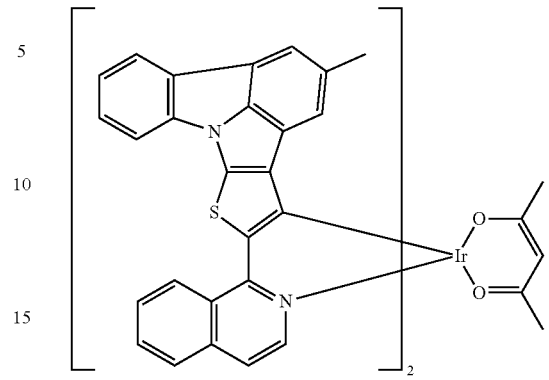
EX183
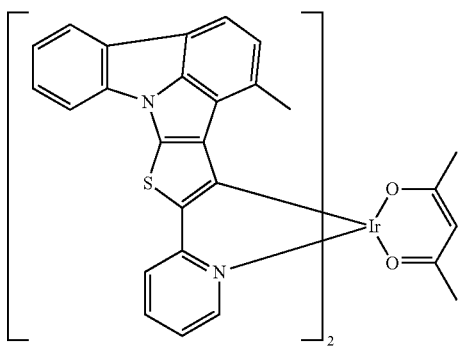
EX187
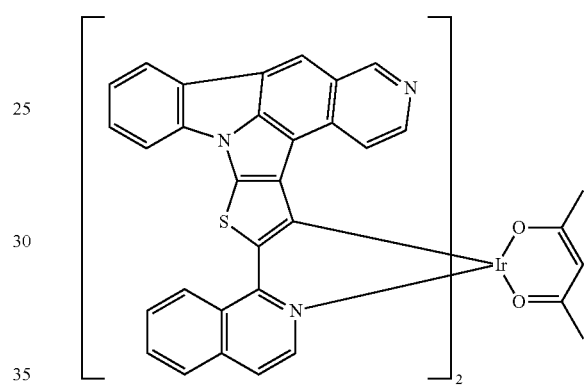
EX184
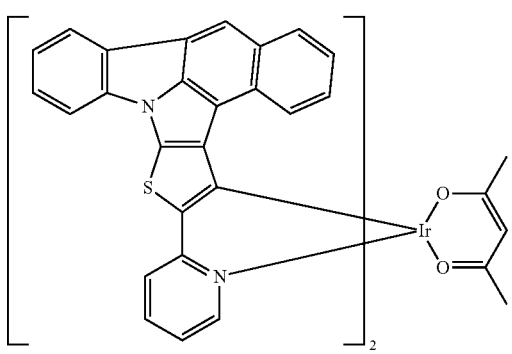
EX188
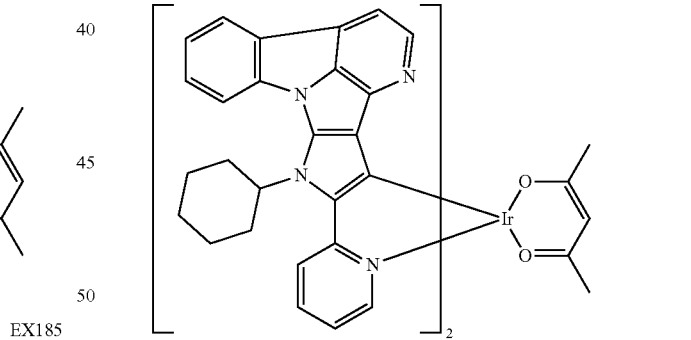
EX185
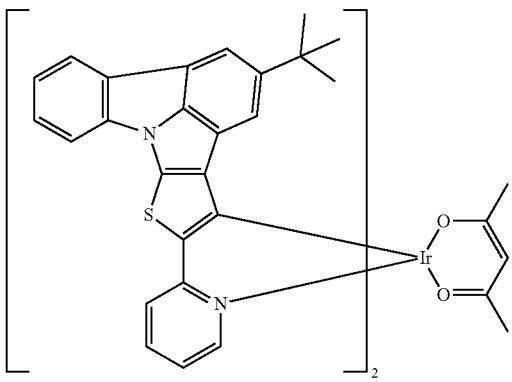
EX189
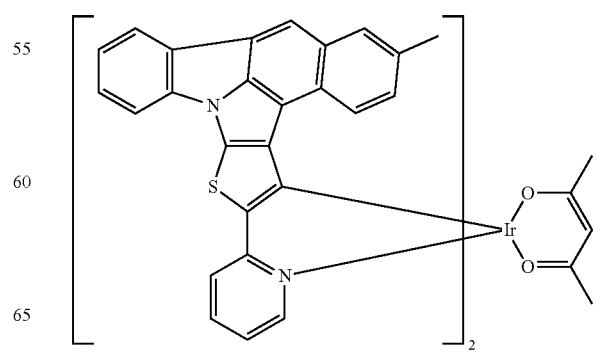

EX190

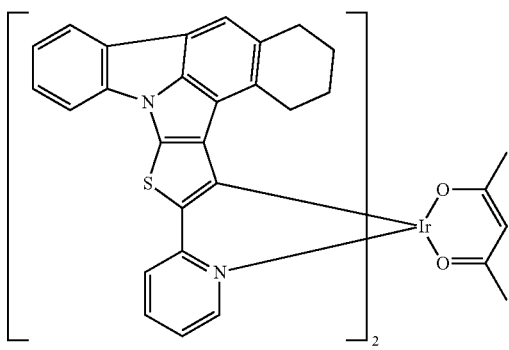

In another embodiment of the present invention, an organic electroluminescence device is disclosed. The organic electroluminescence device comprises a pair of electrodes composed of a cathode and an anode, and a light emitting layer between the pair of electrodes. The light emitting layer comprises the iridium complex of formula (1).

In some embodiments, the light emitting layer further includes a host material, and the iridium complex of formula (1) is used as a phosphorescent dopant material. The host material may be selected from the following compounds:

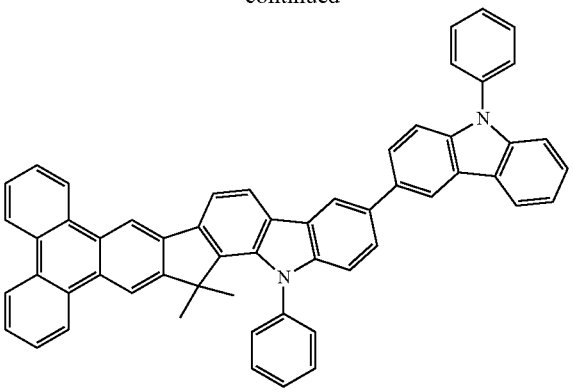

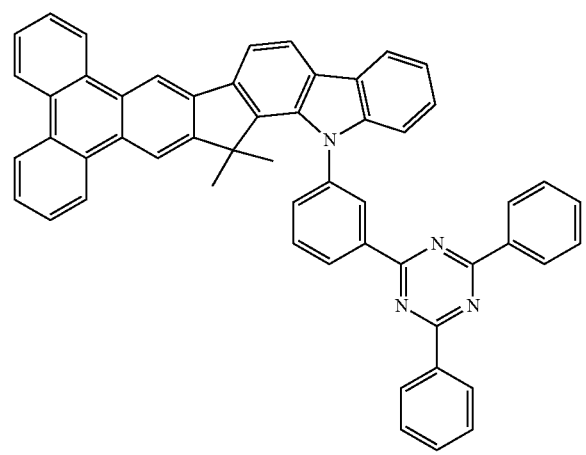

In some embodiments, the light emitting layer emits orange, yellow or red phosphorescence. In yet another embodiment of the present invention, the organic electroluminescent device is a lighting panel. In a further embodiment of the present invention, the organic electroluminescent device is a backlight panel.

Detailed preparation of the iridium complex of the present invention will be clarified by exemplary embodiments below, but the present invention is not limited thereto. EXAMPLE 1 to 8 show the preparation of the iridium complex of the present invention, and EXAMPLE 9 shows the fabrication and the testing report of the organic EL device.

Example 1

Synthesis of EX1

Synthesis of Intermediate A

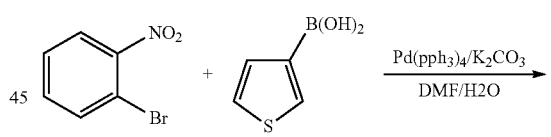

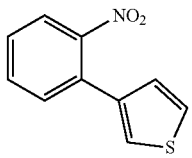

Intermediate A

A mixture of 20 g (99 mmole) of 1-Bromo-2-nitrobenzene, 19 g (148.4 mmole) of 3-thienylboronic acid, 5.7 g (4.93 mmole) of Pd(pph$_3$)$_4$, 27.4 g (198.2 mmole) of K$_2$CO$_3$, 300 ml of DMF, and 80 ml of H$_2$O was placed under nitrogen, and then heated at 80° C. while stirring for 5 h. After the reaction was finished, the mixture was allowed to cool to room temperature. The solution was extracted with 100 ml of ethyl acetate (3 times) and 300 ml of water. The organic layer was dried with anhydrous magnesium sulfate and the solvent was evaporated under reduced pressure. The residue was purified by column chromatography on silica to give product (19 g, 92.5 mmole, 93.5%) as a yellow liquid.

Synthesis of Intermediate B

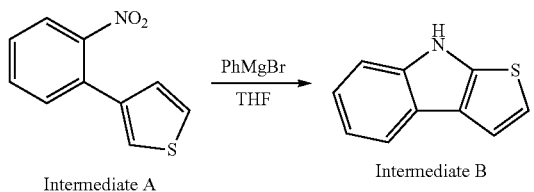 [SMILES: "PhMgBr" ; O=[N+]([O-])c1ccccc1-c1ccsc1 ; c1ccc2c(c1)[nH]c1sccc12 ; "THF"]

Intermediate A → Intermediate B

PhMgBr (1 M in THF solution) (170 mL, 170.5 mmol) was slowly (0.3 mL/min) added to the mixture of Intermediate A (10 g, 48.7 mmol) and dry THF (300 mL) at 0° C. in 10 minutes. During this period, the internal temperature was closely monitored and controlled to remain below 3° C. Then the mixture was stirred at 0° C. for 5 minutes, followed by the slow and careful addition of saturated $NH_4Cl$ aqueous solution (30 mL). The internal temperature was controlled so that it remained below 5° C. Then 50 mL of water was added and the resulting mixture was extracted with ethylacetate (3×100 mL). The combined organic layers were washed with brine (200 mL), dried over anhydrous $Na_2SO_4$, filtered and concentrated in vacuo. The crude product was purified by column chromatography to give product (4 g, 23.2 mmole, 47.6%) as a white solid.

Synthesis of Intermediate C

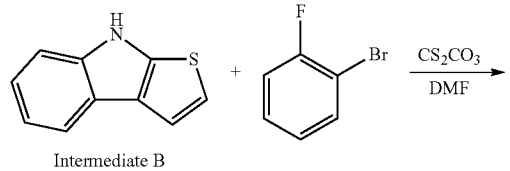

Intermediate B

A mixture of 5 g (28.8 mmole) of Intermediate B, 5.6 g (32 mmole) of 1-bromo-2-fluorobenzene, 14.1 g (43.3 mmole) of caesium carbonate, 80 ml of DMF was placed under nitrogen, and then heated at 150° C. while stirring for 12 h. After the reaction was finished, the mixture was allowed to cool to room temperature. The solution was extracted with 250 ml of ethyl acetate and 300 ml of water. The organic layer was dried with anhydrous magnesium sulfate and the solvent was evaporated under reduced pressure. The residue was purified by column chromatography on silica to give product (9 g, 27.4 mmole, 94.7%) as a purple solid.

Synthesis of Intermediate D

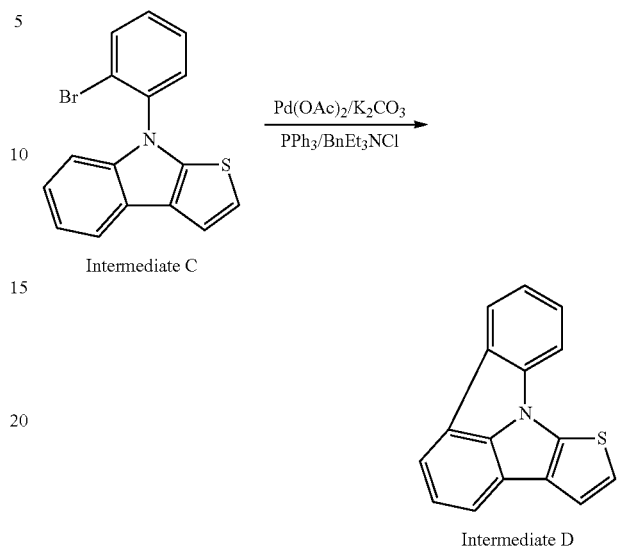

Intermediate C → Intermediate D

A mixture of 7.5 g (22.8 mmole) of Intermediate C, 15.8 g (114.3 mmole) of $K_2CO_3$, 2.4 g (9.15 mmole) of $PPh_3$, 5.2 g (22.8 mmole) of benzyltriethyl ammonium chloride, 0.78 g (3.47 mmole) of $Pd(OAc)_2$, and 150 ml of DMAc was placed under nitrogen, and then heated at 160° C. while stirring for 5 h. After the reaction was finished, the mixture was allowed to cool to room temperature. The solution was extracted with 250 ml of DCM and 300 ml of water. The organic layer was dried with anhydrous magnesium sulfate and the solvent was evaporated under reduced pressure. The residue was purified by column chromatography on silica to give product (2.1 g, 8.49 mmole, 37.5%) as a pink solid. 1H NMR (500 MHz, CDCl3): δ8.08-8.07 (d, 1H), 7.91-7.89 (d, 1H), 7.85-7.84 (d, 1H), 7.69-7.67 (d, 1H), 7.54-7.46 (m, 3H), 7.34-7.31 (m, 1H), 7.06-7.05 (d, 1H), ppm

Synthesis of Intermediate E

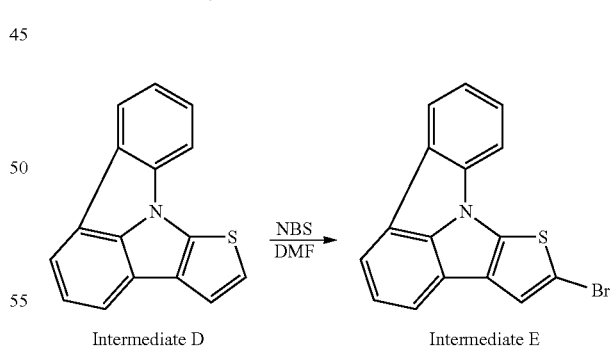

Intermediate D → Intermediate E

In the $N_2$ gas purging system, 2.1 g (8.49 mmole) of Intermediate D and 1.6 g (8.98 mmole) of N-bromosuccinimide were put into 50 ml of DMF, where the light was blocked out, and the mixture was stirred for 12 h. After completion of the reaction, the mixture was extracted with 250 ml of DCM and 300 ml of water. The organic layer was dried with anhydrous magnesium sulfate and the solvent was evaporated under reduced pressure. The residue was purified by column chromatography on silica to give product (2.2 g, 6.74 mmole, 79.1%) as a white solid. 1H NMR (500 MHz, CDCl3): δ8.10-8.08 (d, 1H), 7.93-7.92 (d, 1H), 7.82-7.81 (d, 1H), 7.64-7.63 (d, 1H), 7.56-7.50 (m, 2H), 7.37-7.34 (m, 1H), 7.19-7.17 (d, 1H) ppm Synthesis of Intermediate F

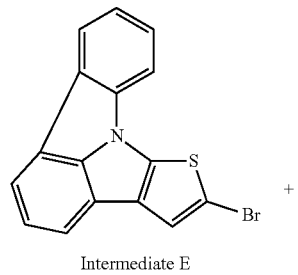

Intermediate E

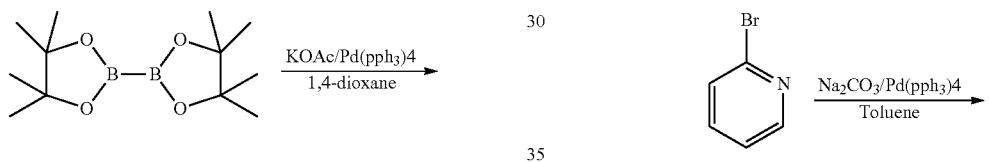

Intermediate F

A mixture of 2 g (6.13 mmole) of Intermediate E, 1.86 g (7.36 mmol) of bis(pinacolato)diboron, 0.13 g (0.12 mmol) of tetrakis(triphenylph osphine)palladium, 1.8 g (18.39 mmol) of potassium acetate, and 60 ml of 1,4-dioxane was degassed and placed under nitrogen, and then heated at 90° C. for 16 h. After the reaction was finished, the mixture was allowed to cool to room temperature. The organic phase was separated and washed with ethyl acetate and water. After being dried with magnesium sulfate, the solvent was removed in vacuo. The residue was purified by column chromatography on silica to give product 1.2 g (53%) as an off-white solid.

Synthesis of Intermediate G

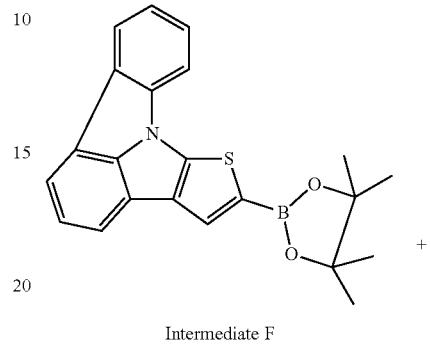

Intermediate F

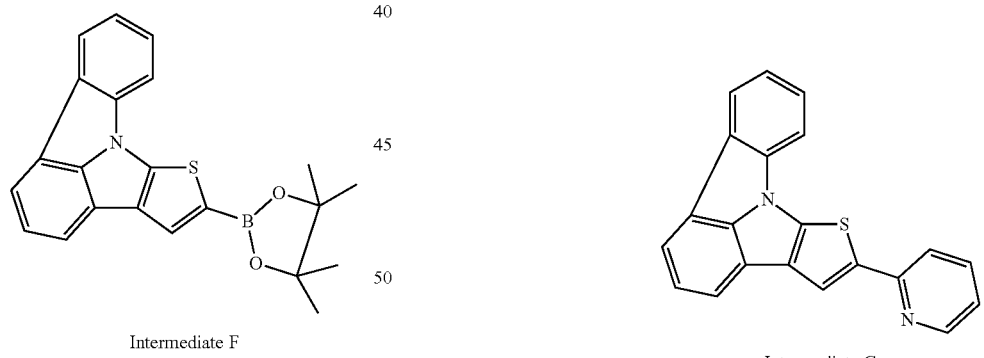

Intermediate G

A mixture of 1.2 g (3.21 mmol) of Intermediate F, 0.8 g (4.8 mmol) of 2-bromopyridine, 70 mg (0.06 mmol) of tetrakis(triphenylphosphine) palladium, 7 ml of 2 M Na2CO3, 10 ml of EtOH, and 30 ml of toluene was degassed and placed under nitrogen, and then heated at 90° C. overnight. After the reaction was finished, the mixture was allowed to cool to room temperature. Then 100 ml of MeOH was added while stirring and the precipitated product was filtered off with suction to give 0.6 g (61%) of off-white product, which was recrystallized from EtOH. 1H NMR (500 MHz, CDCl3): δ8.51-8.49 (d, 1H), 8.10-8.08 (d, 1H), 7.93-7.92 (d, 1H), 7.88-7.81 (m, 3H), 7.64-7.61 (d, 1H), 7.56-7.50 (m, 2H), 7.40-7.34 (m, 2H), 7.19-7.17 (d, 1H) ppm Synthesis of Intermediate H

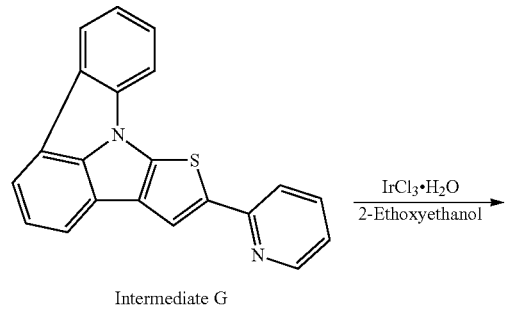

Intermediate G

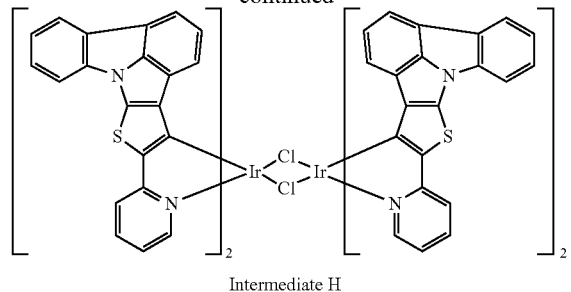

Intermediate H

A mixture of 1 g (3.08 mmol) of Intermediate G, 0.4 g (1.3 mmol) of Iridium(III) chloride hydrate, 20 ml of 2-ethoxyethanol and 9 ml water was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.9 g (63%) of red product.

Synthesis of EX1

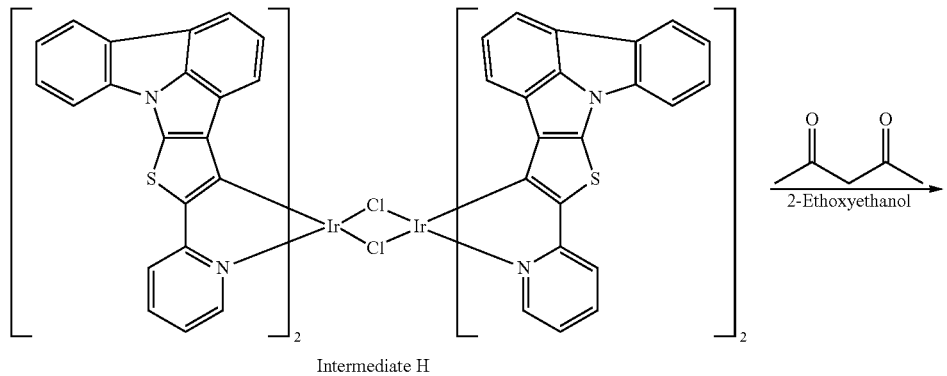

Intermediate H

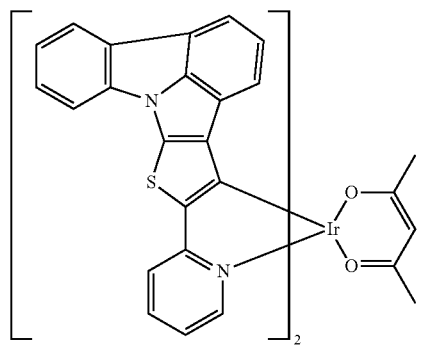

A mixture of 0.9 g (0.82 mmol) of Intermediate H, 0.8 g (8.2 mmol) of acetylacetone, 1.7 g (16.07 mmol) of sodium carbonate, and 18 ml of 2-ethoxyethanol was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.4 g (52%) of brown product. 1H NMR (500 MHz, CDCl3): δ8.33-8.28 (m, 2H), 8.12-8.07 (m, 2H), 8.01-7.93 (m, 2H), 7.85-7.79 (m, 6H), 7.69-7.61 (m, 2H), 7.56-7.50 (m, 4H), 7.43-7.36 (m, 4H), 5.25 (s, 1H), 1.83 (s, 6H) ppm Example 2

Synthesis of EX2

Synthesis of Intermediate I

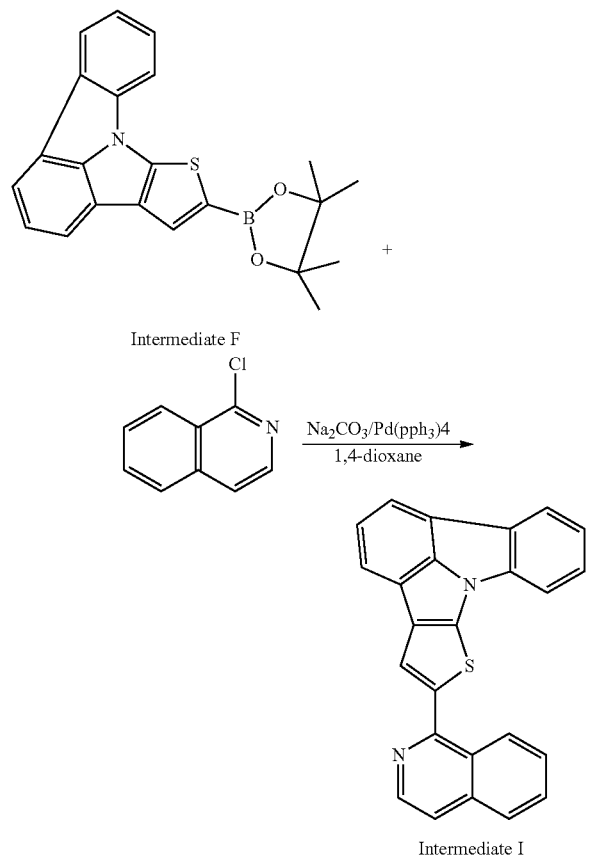

Intermediate I

A mixture of 2.4 g (6.42 mmol) of Intermediate F, 1.26 g (7.7 mmol) of 1-chloroisoquinoline, 140 mg (0.12 mmol) of tetrakis(triphenylphosphine)-palladium, 14 ml of 2 M Na₂CO₃, 15 ml of EtOH and 50 ml of toluene was degassed and placed under nitrogen, and then heated at 90° C. overnight. After the reaction was finished, the mixture was allowed to cool to room temperature. Then 100 ml of MeOH was added while stirring and the precipitated product was filtered off with suction to give 1.56 g (65%) of off-white product, which was recrystallized from EtOH. 1H NMR (500 MHz, CDCl3): δ8.51-8.49 (d, 1H), 8.10-8.08 (d, 1H), 7.93-7.92 (d, 1H), 7.88-7.81 (m, 3H), 7.64-7.61 (d, 1H), 7.56-7.50 (m, 4H), 7.40-7.34 (m, 2H), 7.19-7.17 (d, 1H), ppm.

Synthesis of Intermediate J

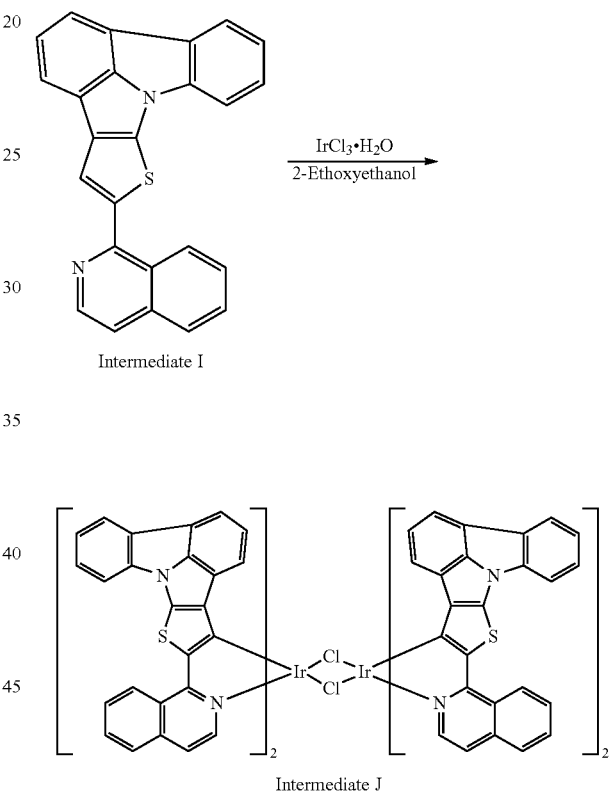

Intermediate J

A mixture of 1.56 g (4.17 mmol) of Intermediate I, 0.55 g (1.75 mmol) of Iridium(III) chloride hydrate, 25 ml of 2-ethoxyethanol and 10 ml of water was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 1.28 g (61%) of red product.

Synthesis of EX2

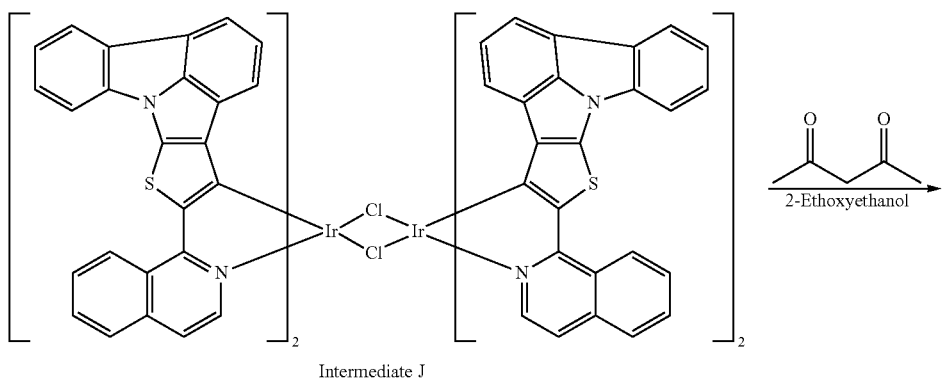

Intermediate J

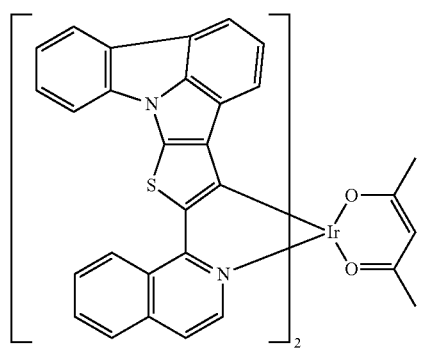

A mixture of 1.28 g (1.06 mmol) of Intermediate J, 1.06 g (10.6 mmol) of acetylacetone, 2.2 g (20.77 mmol) of sodium carbonate, and 20 ml of 2-ethoxyethanol was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.6 g (55%) of brown product. 1H NMR (500 MHz, CDCl3): δ8.35-8.30 (m, 2H), 8.14-8.08 (m, 2H), 7.99-7.94 (m, 2H), 7.84-7.77 (m, 6H), 7.64-7.61 (m, 2H), 7.56-7.49 (m, 8H), 7.42-7.36 (m, 4H), 5.21 (s, 1H), 1.79 (s, 6H), ppm.

Example 3

Synthesis of EX5

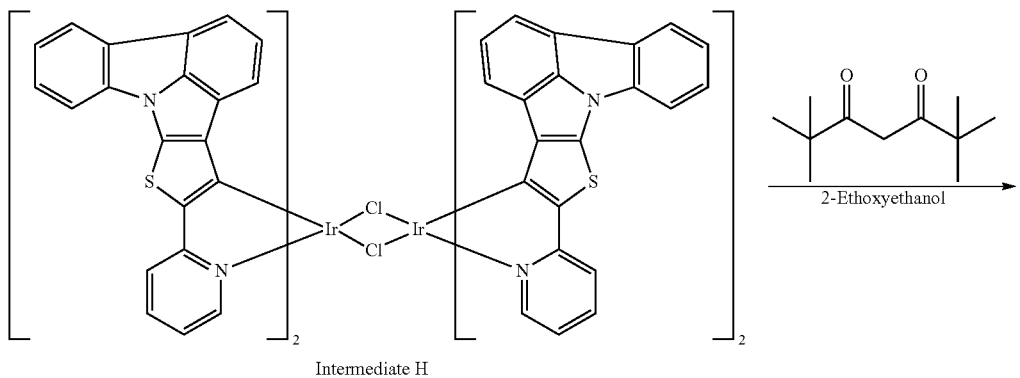

Intermediate H

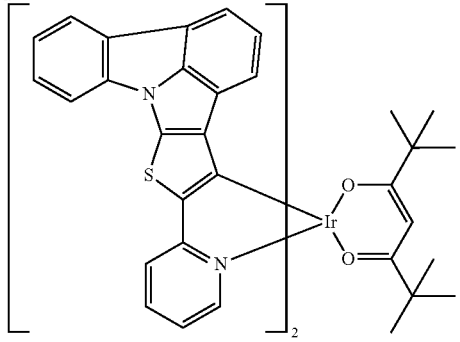

A mixture of 0.9 g (0.82 mmol) of Intermediate H, 1.05 g (5.74 mmol) of 2,2,6,6-tetramethyl-3,5-heptanedione, 0.87 g (8.2 mmol) of sodium carbonate, and 18 ml of 2-ethoxyethanol was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.45 g (54%) of brown product. 1H NMR (500 MHz, CDCl3): δ8.35-8.28 (m, 2H), 8.17-8.07 (m, 2H), 8.05-7.93 (m, 2H), 7.87-7.79 (m, 6H), 7.67-7.61 (m, 2H), 7.54-7.49 (m, 4H), 7.47-7.37 (m, 4H), 5.27 (s, 1H), 1.34 (s, 18H) ppm Example 4

Synthesis of EX6

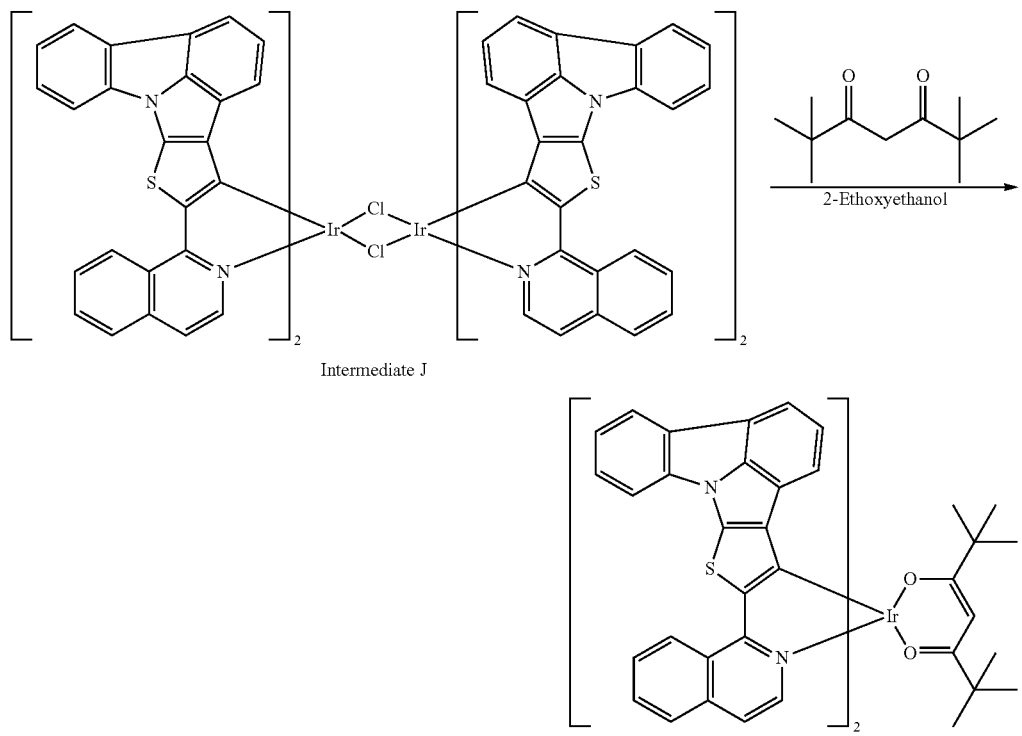

A mixture of 1.28 g (1.06 mmol) of Intermediate J, 1.36 g (7.42 mmol) of 2,2,6,6-tetramethyl-3,5-heptanedione, 1.12 g (10.6 mmol) of sodium carbonate, and 20 ml of 2-ethoxyethanol was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.6 g (51%) of brown product. 1H NMR (500 MHz, CDCl3): δ8.37-8.31 (m, 2H), 8.13-8.07 (m, 2H), 7.99-7.93 (m, 2H), 7.83-7.77 (m, 6H), 7.67-7.61 (m, 2H), 7.57-7.49 (m, 8H), 7.44-7.36 (m, 4H), 5.21 (s, 1H), 1.41 (s, 18H), ppm.

Example 5

Synthesis of EX27

A mixture of 0.9 g (0.82 mmol) of Intermediate H, 1.3 g (6.13 mmol) of 3,7-diethylnonane-4,6-dione, 0.87 g (8.2 mmol) of sodium carbonate, and 18 ml of 2-ethoxyethanol was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.41 g (48%) of brown product. 1H NMR (500 MHz, CDCl3): δ8.37-8.29 (m, 2H), 8.16-8.08 (m, 2H), 8.05-7.91 (m, 2H), 7.88-7.80 (m, 6H), 7.69-7.61 (m, 2H), 7.58-7.52 (m, 4H), 7.50-7.35 (m, 4H), 5.31 (s, 1H), 2.51-2.41 (m, 2H), 2.21-1.81 (m, 8H), 1.22 (s, 12H) ppm

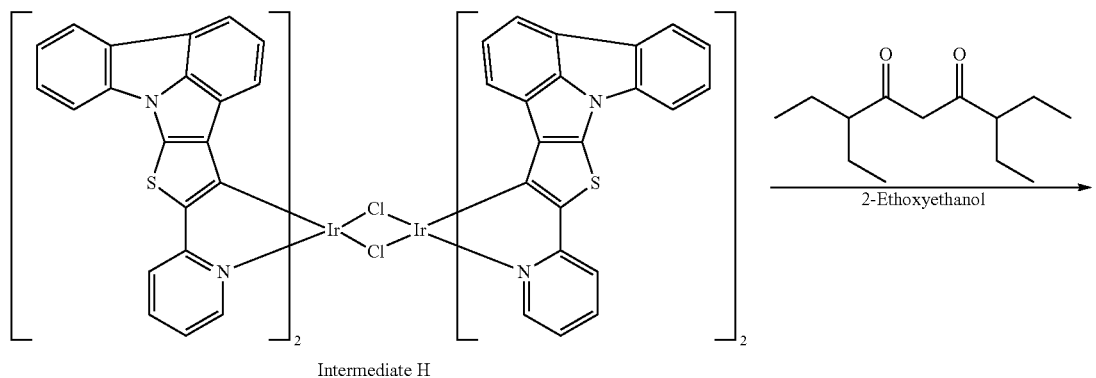

Intermediate H

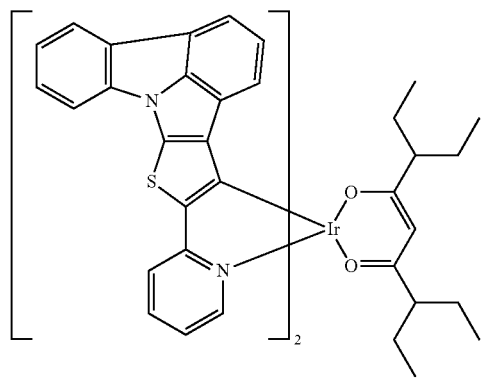

Example 6

Synthesis of EX30

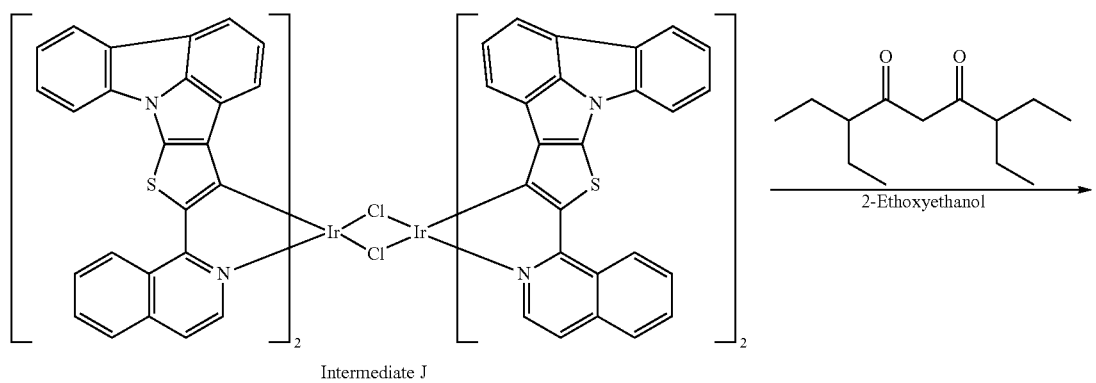

Intermediate J

A mixture of 1.28 g (1.06 mmol) of Intermediate J, 1.68 g (7.92 mmol) of 3,7-diethylnonane-4,6-dione, 1.12 g (10.6 mmol) of sodium carbonate, and 20 ml of 2-ethoxyethanol was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.6 g (49%) of brown product. 1H NMR (500 MHz, CDCl3): δ8.45-8.40 (m, 2H), 8.15-8.11 (m, 2H), 7.99-7.90 (m, 2H), 7.86-7.75 (m, 6H), 7.69-7.60 (m, 2H), 7.58-7.47 (m, 8H), 7.41-7.33 (m, 4H), 5.21 (s, 1H), 2.55-2.43 (m, 2H), 2.23-1.79 (m, 8H), 1.21 (s, 12H) ppm.

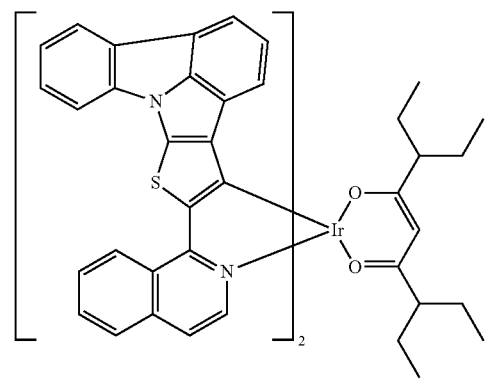

Example 7

Synthesis of EX40

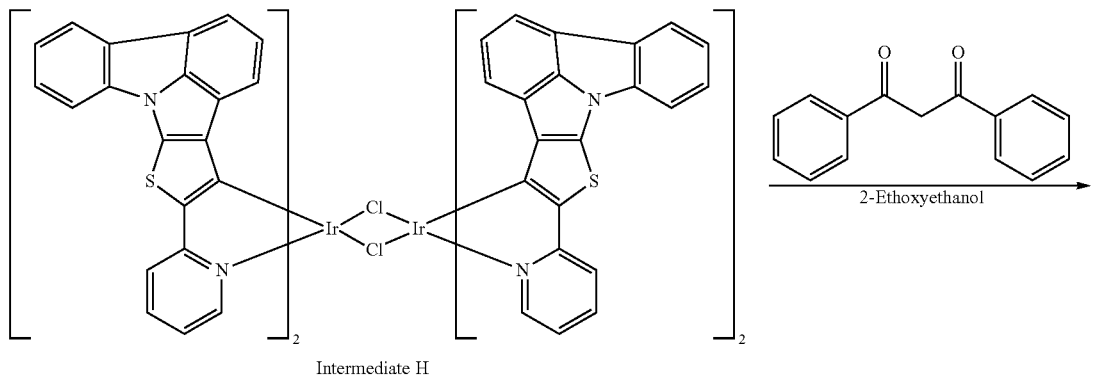

Intermediate H

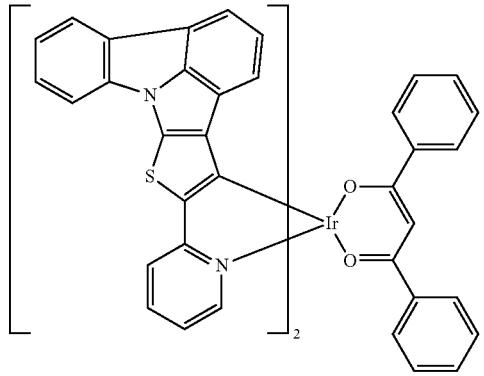

A mixture of 0.9 g (0.82 mmol) of Intermediate H, 1.29 g (5.74 mmol) of dibenzoylmethane, 0.87 g (8.2 mmol) of sodium carbonate, and 18 ml of 2-ethoxyethanol was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.36 g (41%) of brown product. 1H NMR (500 MHz, CDCl3): δ8.37-8.27 (m, 2H), 8.20-8.09 (m, 2H), 8.06-7.92 (m, 2H), 7.86-7.78 (m, 6H), 7.69-7.61 (m, 6H), 7.57-7.51 (m, 8H), 7.49-7.35 (m, 6H), 5.27 (s, 1H) ppm Example 8

Synthesis of EX42

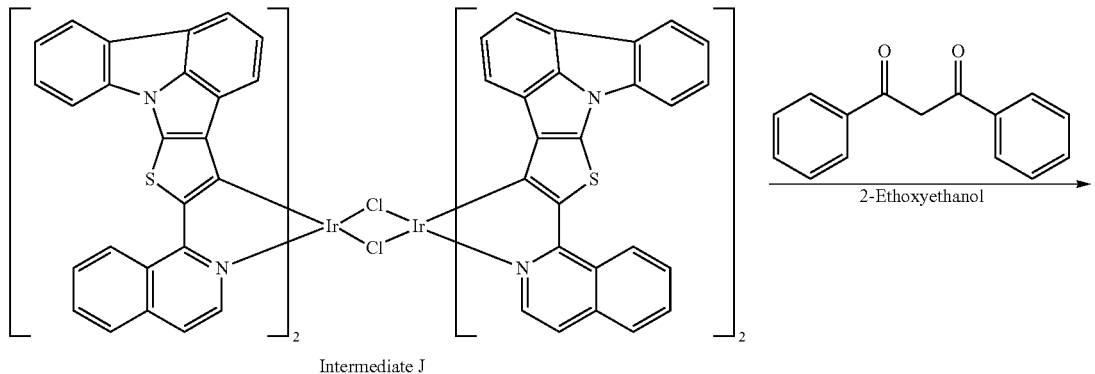

Intermediate J

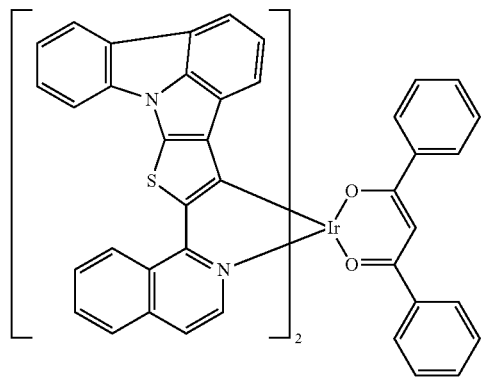

A mixture of 1.28 g (1.06 mmol) of Intermediate J, 1.66 g (7.42 mmol) of dibenzoylmethane, 1.12 g (10.6 mmol) of sodium carbonate, and 20 ml of 2-ethoxyethanol was degassed and placed under nitrogen, and then heated at 120° C. overnight. After the reaction was finished, the mixture was allowed to cool to room temperature. The precipitated product was filtered off with suction and washed with water. Afterwards, 100 ml of water was added and then stirred for 1 hr, and the precipitated product was filtered off with suction. Subsequently, 50 ml of EtOH was added and then stirred for 1 hr, and the precipitated product was filtered off with suction to give 0.57 g (46%) of brown product. 1H NMR (500 MHz, CDCl3): δ8.39-8.33 (m, 2H), 8.14-8.06 (m, 2H), 7.98-7.91 (m, 2H), 7.87-7.79 (m, 6H), 7.69-7.63 (m, 6H), 7.59-7.47 (m, 10H), 7.43-7.34 (m, 6H), 5.23 (s, 1H) ppm.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is successfully achieved by co-vaporization from two or more sources, which means the iridium complex of the present invention is thermally stable.

Dipyrazino[2,3-f:2,3-]quinoxaline-2,3,6,7,10,11-hexacarbonitrile (HAT-CN) is used as hole injection layer in this organic EL device, N,N-Bis(naphthalene-1-yl)-N,N-bis(phenyl)-benzidine (NPB) is used as the hole transporting layer, and N-(biphenyl-4-yl)-9,9-dimethyl-N-(4'-phenyl-biphenyl-4-yl)-9H-fluoren-2-amine (EB2) is used as electron blocking layer, and the chemical structures thereof are shown below:

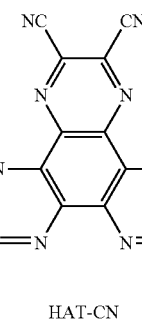

HAT-CN

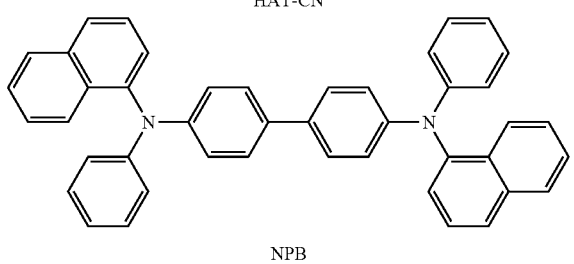

NPB

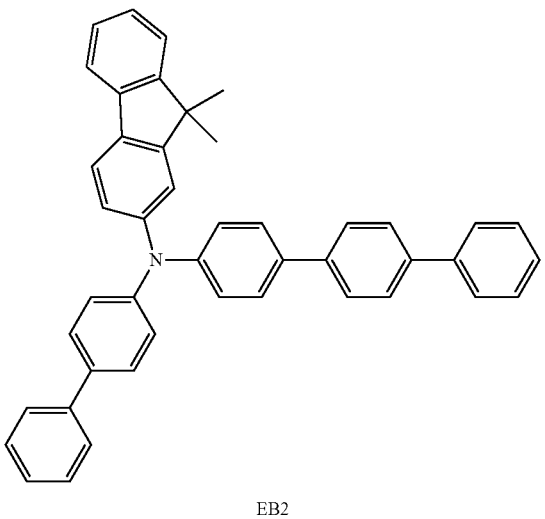

EB2

In the present invention, the host material is selected from the following compounds:

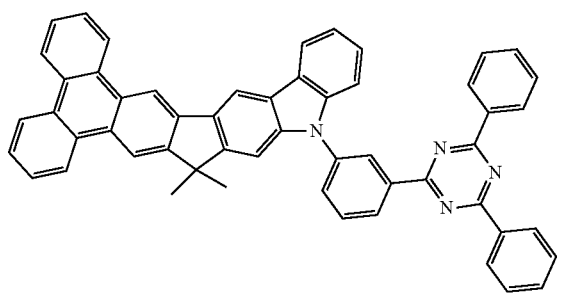

H1

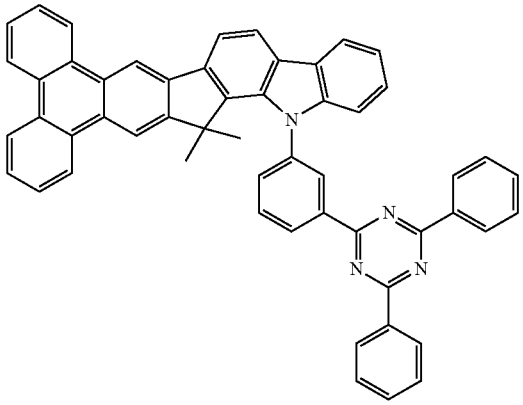

H2

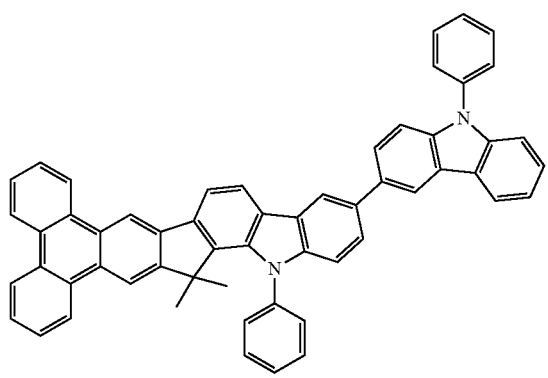
H3

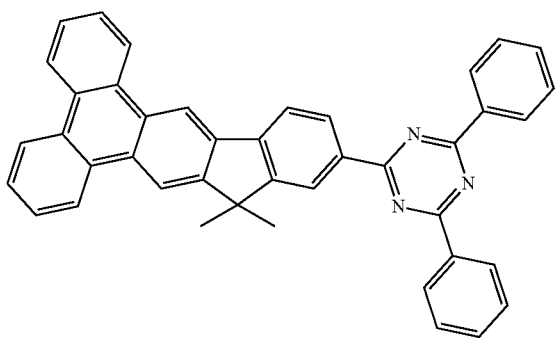
ET2

Organic iridium complexes are widely used as phosphorescent dopant for light emitting layer, and Ir(piq)$_2$(acac) and Ir(2-phq)$_2$(acac) are used as phosphorescent dopant of light emitting layer for comparison in the present invention.

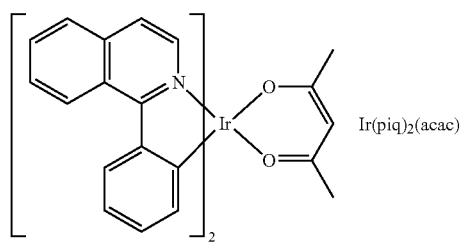
Ir(piq)$_2$(acac)

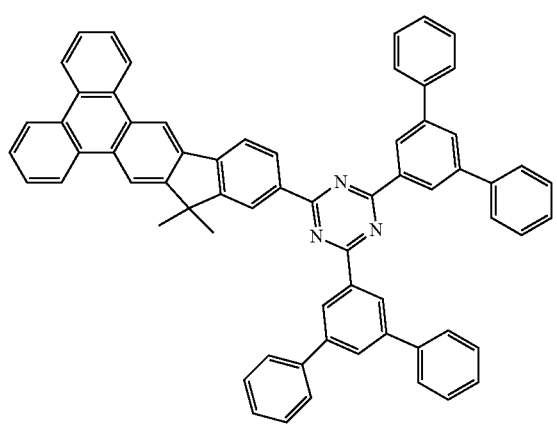
HB3

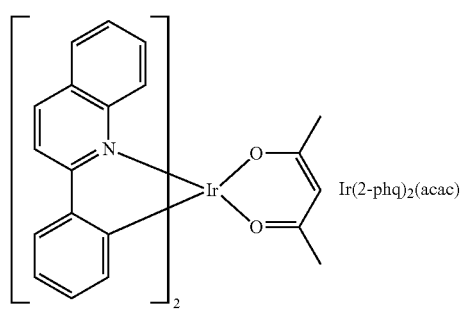
Ir(2-phq)$_2$(acac)

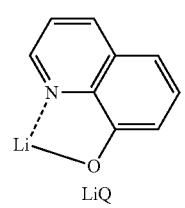
LiQ

HB3 (see the following chemical structure) is used as hole blocking material (HBM), and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The chemical structures of conventional OLED materials and the exemplary iridium complexes of the present invention for producing control and exemplary organic EL devices in this invention are shown as follows:

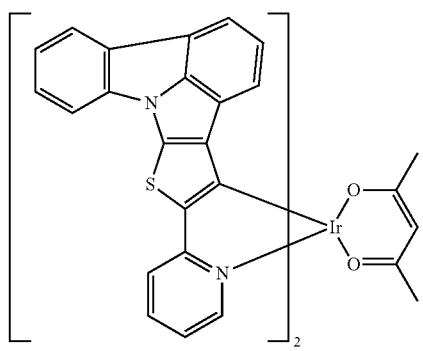
EX1

EX2

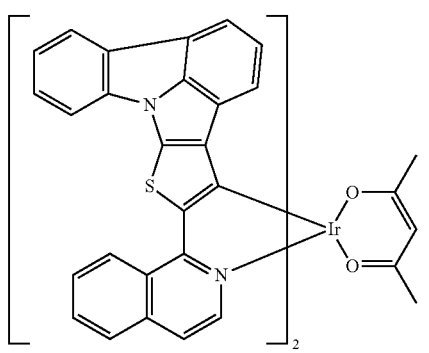

EX5

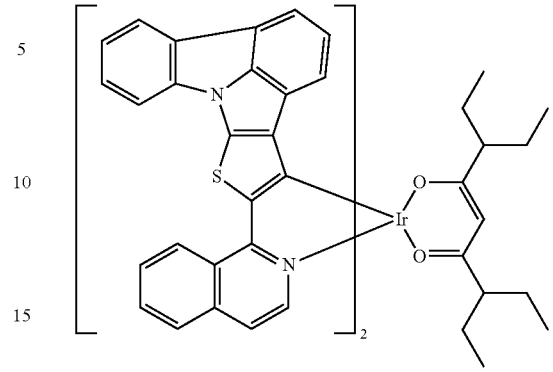

EX6

EX27

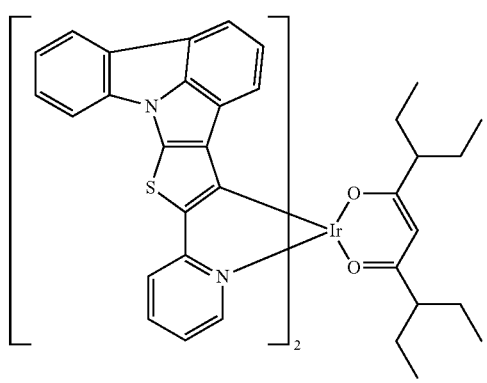

EX30

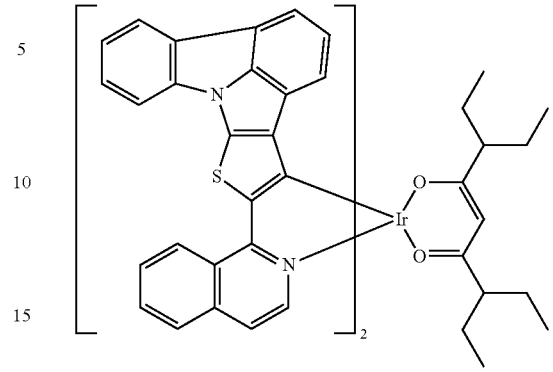

EX40

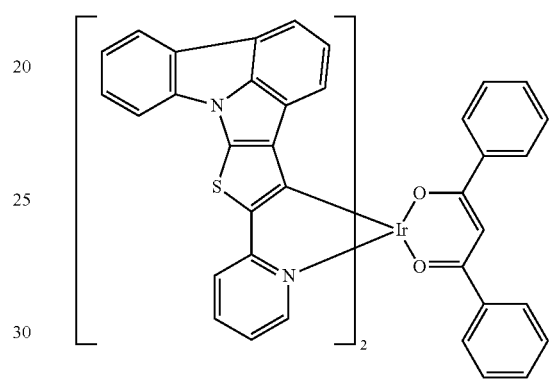

EX42

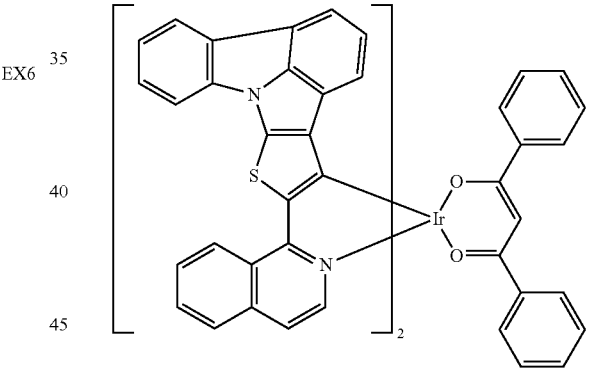

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 9

Using a procedure analogous to the above mentioned general method, phosphorescent emitting organic EL device having the following device structure was produced (See the FIGURE). Device: ITO/HAT-CN(20 nm)/NPB (110 nm)/EB2(5 nm)/H1 to H3 doped with 15% phosphorescent emitting dopant (30 nm)/HB3(10 nm)/ET2 doped with 40% LiQ(35 nm)/LiQ(1 nm)/Al(160 nm). The I-V-B (at 1000 nits) and half-life time testing reports of phosphorescent emitting organic EL devices are shown in Table 1. The half-life time is defined as the time the initial luminance of 1000 cd/m$^2$ has dropped to half.

TABLE 1

| Host | Dopant | Voltage (V) | Efficiency (cd/A) | Color | Half-life time (hour) |
|---|---|---|---|---|---|
| H2 + H3 | EX1 | 3.9 | 22 | Red | 850 |
| H2 + H3 | EX5 | 3.7 | 23 | Red | 950 |
| H2 + H3 | EX27 | 4.2 | 19 | Red | 750 |
| H2 + H3 | Ir(2-phq)$_2$(acac) | 4.5 | 18 | Red | 430 |
| H1 + H3 | EX2 | 4.1 | 17 | Red | 710 |
| H1 + H3 | EX6 | 3.9 | 19 | Red | 800 |
| H1 + H3 | EX30 | 4.0 | 18 | Red | 750 |
| H1 + H3 | EX40 | 4.4 | 16 | Red | 630 |
| H1 + H3 | EX42 | 4.6 | 14 | Red | 600 |
| H1 + H3 | Ir(piq)$_2$(acac) | 4.8 | 15 | Red | 310 |

In the above test report for the preferred embodiments of the phosphorescent organic EL devices (see Table 1), we show that the iridium complex of formula (1) used as the dopant material of light emitting layer for organic EL device in the present invention displays good performance than the prior art organic EL materials. More specifically, the organic EL device of the present invention uses the iridium complex of formula (1) as light emitting dopant material to collocate with emitting host material H1 to H3, showing lower power consumption, longer half-life time and higher luminous efficiency.

To sum up, the present invention discloses an iridium complex, which can be used as the phosphorescent dopant material of light emitting layer in organic EL devices. The mentioned iridium complex is represented by the following formula (1):

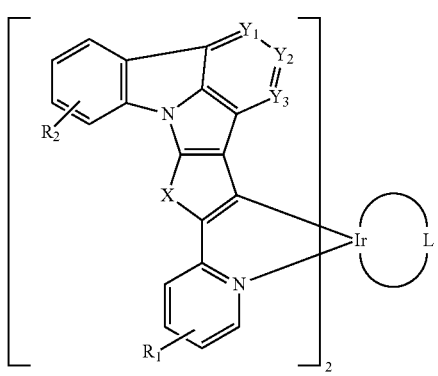

Formula (1)

wherein X is an oxygen atom, a sulfur atom, a selenium atom, NR$_3$, or CR$_4$R$_5$, Y$_1$ to Y$_3$ are each independently a nitrogen atom or CR$_6$, and L represents formula (2):

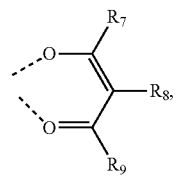

Formula (2)

wherein R$_1$ to R$_9$ are the same or different and each independently selected from the group consisting of a hydrogen atom, a substituted or unsubstituted alkyl group having 1 to 20 carbon atoms, a substituted or unsubstituted carbocyclic ring having 3 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:
1. An iridium complex of formula (1):

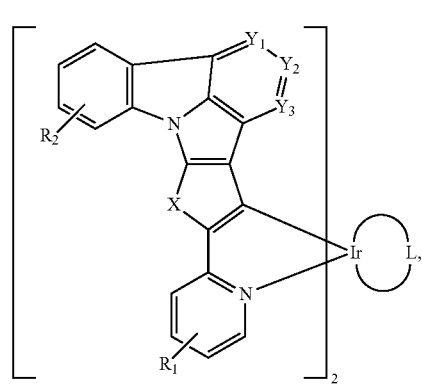

Formula (1)

wherein X is an oxygen atom, a sulfur atom, a selenium atom, NR$_3$, or CR$_4$R$_5$, Y$_1$ to Y$_3$ are each independently a nitrogen atom or CR$_6$, and L represents formula (2):

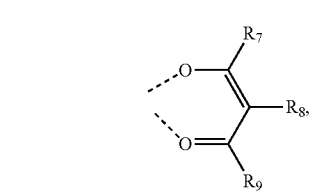

Formula (2)

wherein R$_1$ to R$_9$ are the same or different and each independently selected from the group consisting of a hydrogen atom, a substituted or unsubstituted alkyl group having 1 to 20 carbon atoms, a substituted or unsubstituted carbocyclic ring having 3 to 30 carbon atoms, a substituted or unsubstituted aryl group having 6 to 30 carbon atoms, a substituted or unsubstituted aralkyl group having 7 to 30 carbon atoms, and a substituted or unsubstituted heteroaryl group having 3 to 30 carbon atoms.

2. The iridium complex of claim 1, wherein L is selected from the following groups:

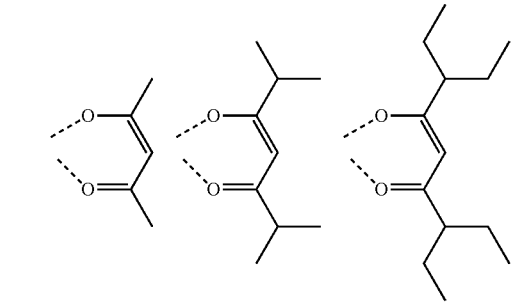

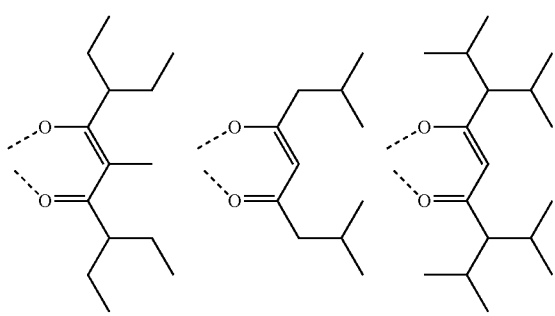

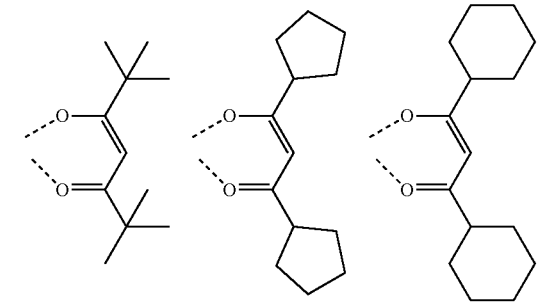

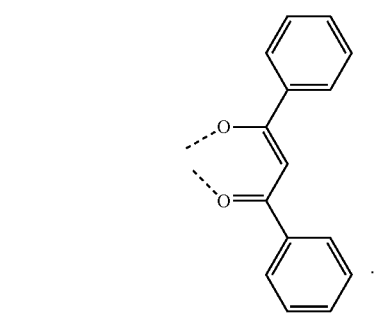

3. An iridium complex represented by any of the following formulae:

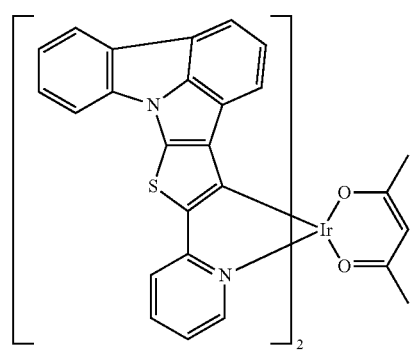
EX1

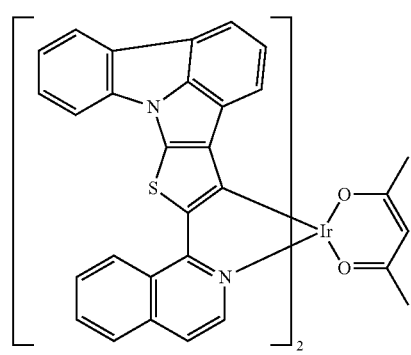
EX2

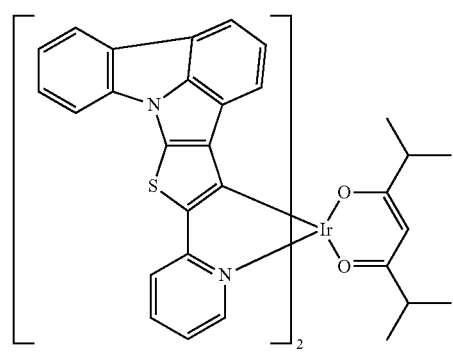
EX3

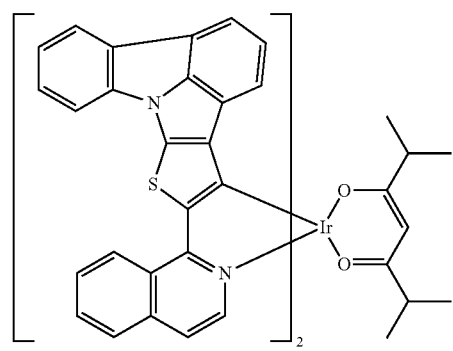
EX4

EX5
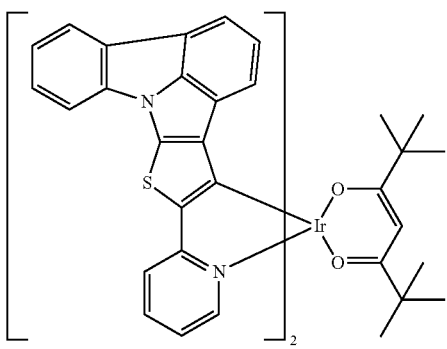
EX6
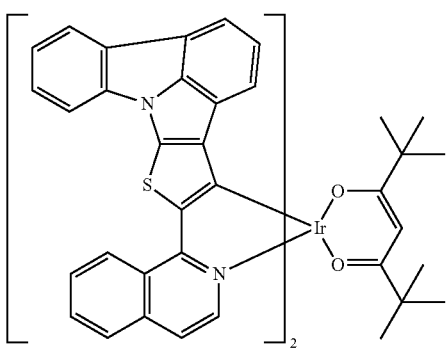
EX7
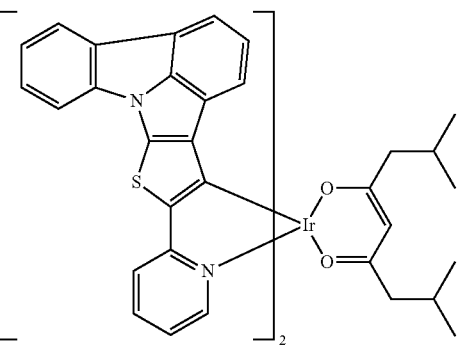
EX8
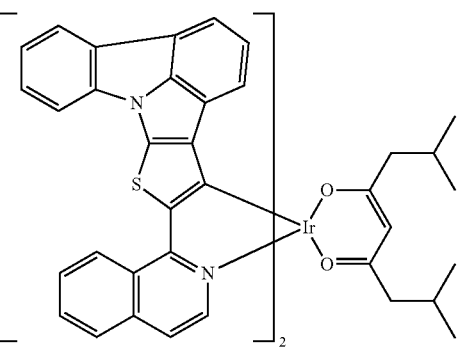
EX9
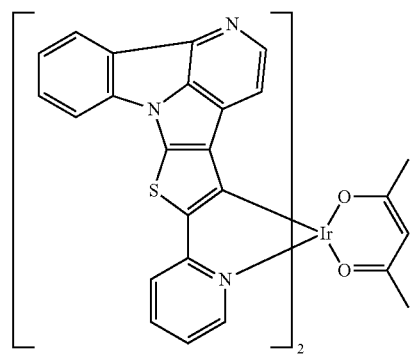
EX10
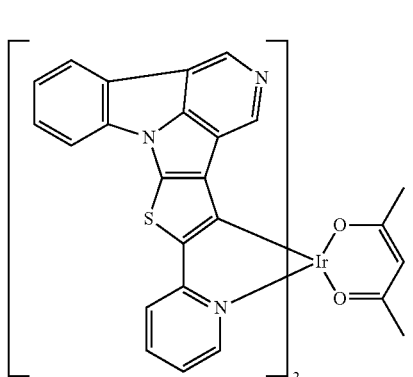
EX11
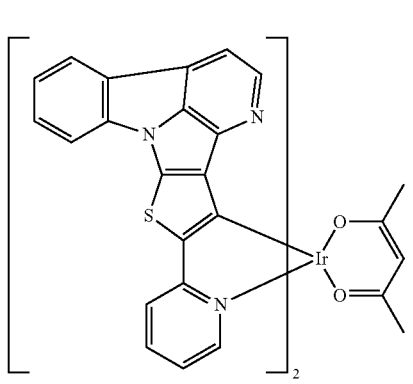
EX12
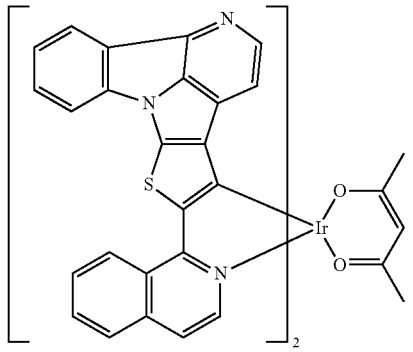

-continued
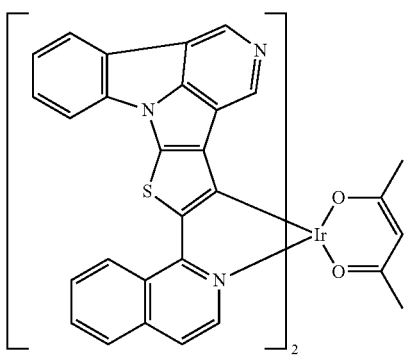
EX13
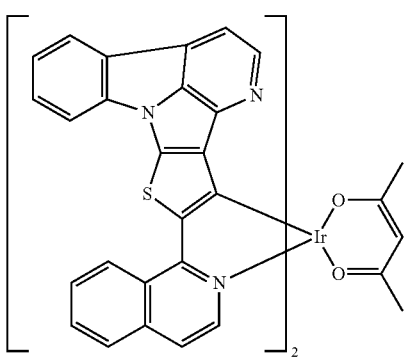
EX14
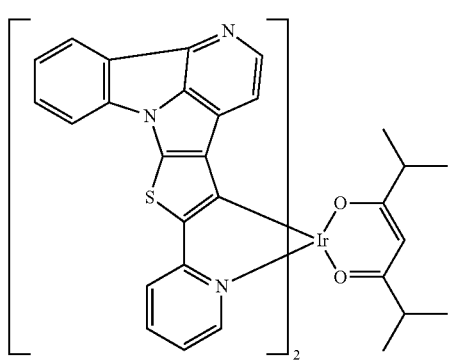
EX15
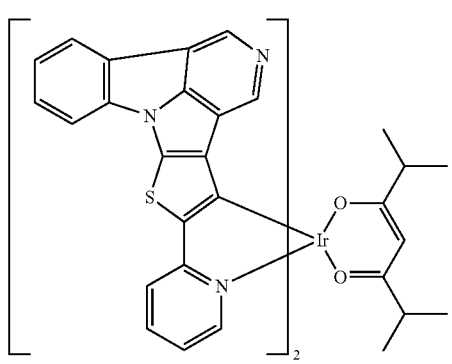
EX16
-continued
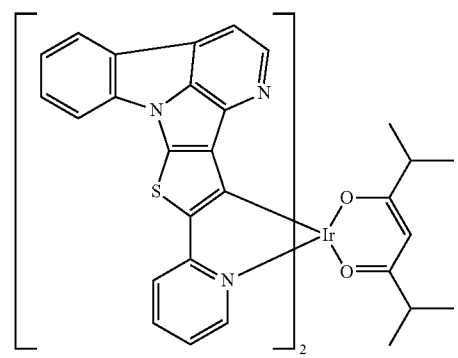
EX17
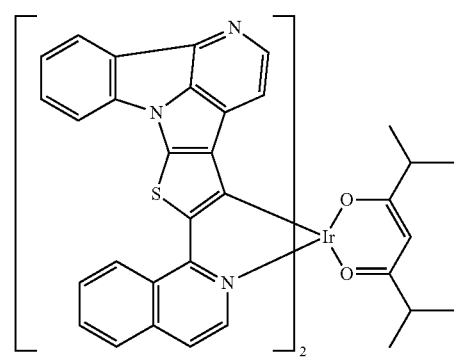
EX18
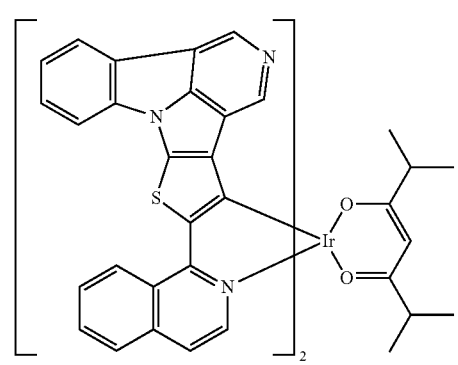
EX19
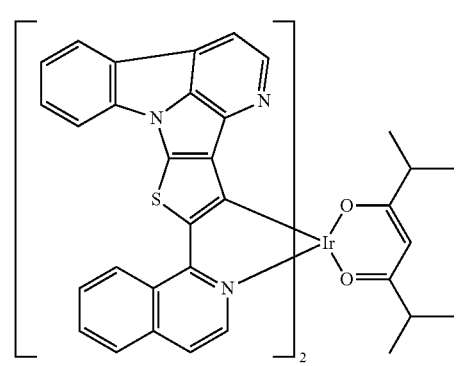
EX20

EX21
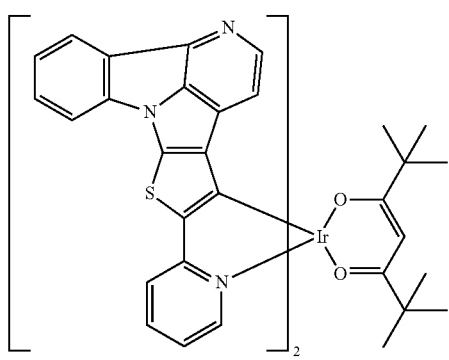
EX22
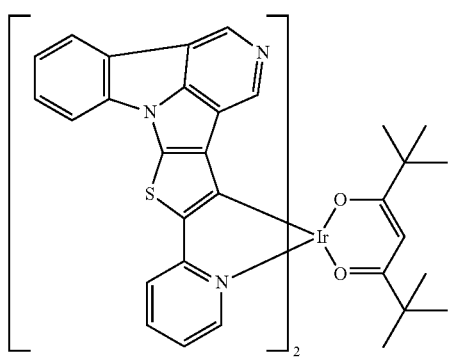
EX23
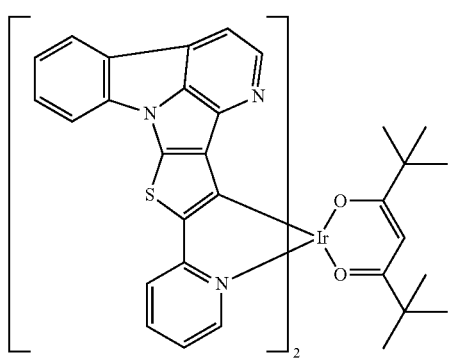
EX24
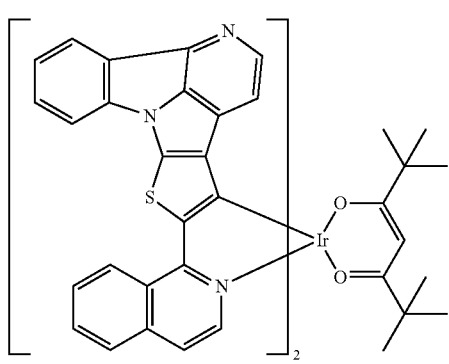
EX25
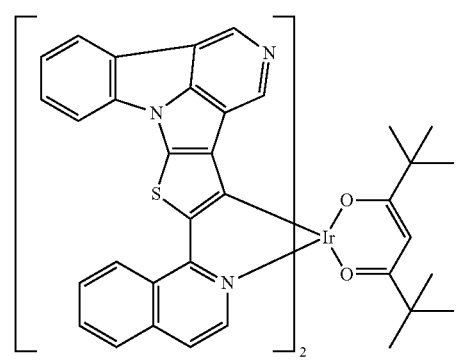
EX26
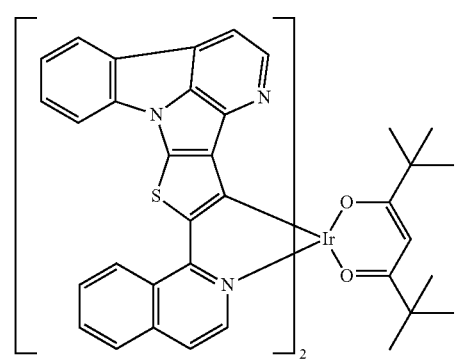
EX27
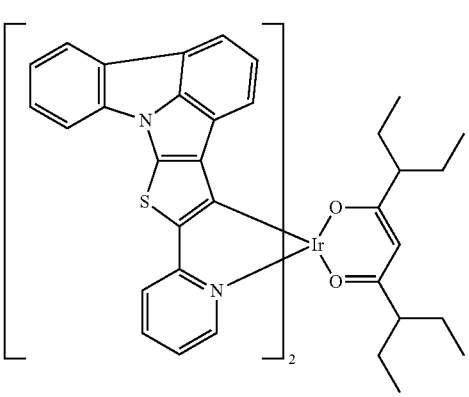
EX28
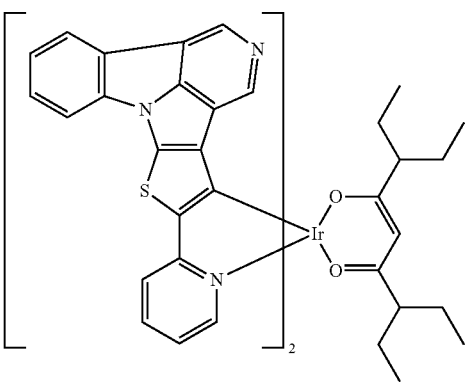

EX29
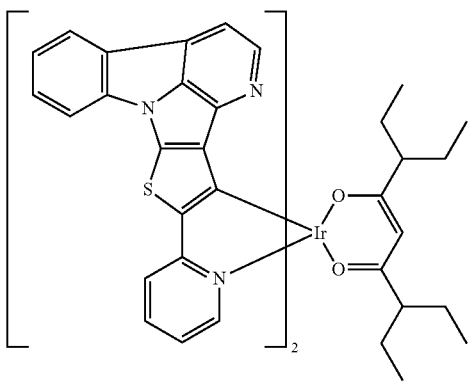
EX30
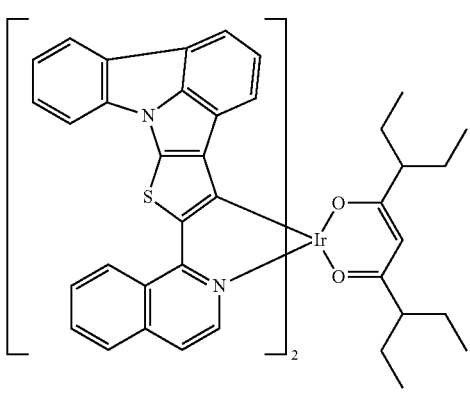
EX31
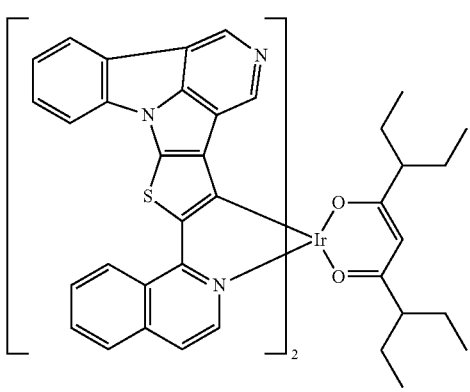
EX32
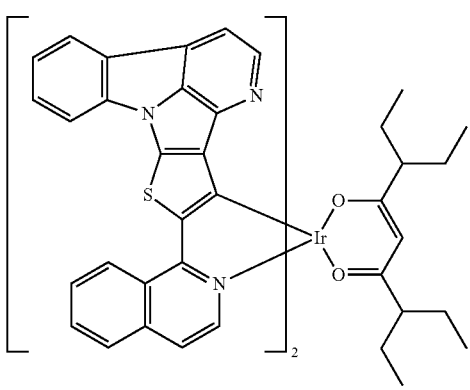
EX33
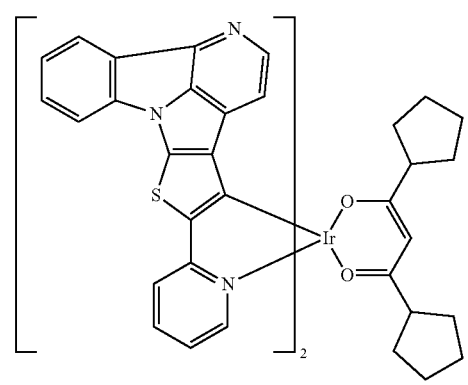
EX34
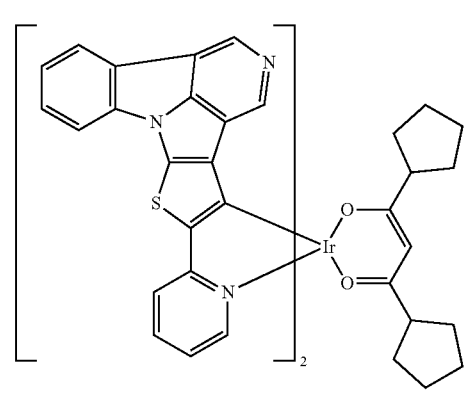
EX35
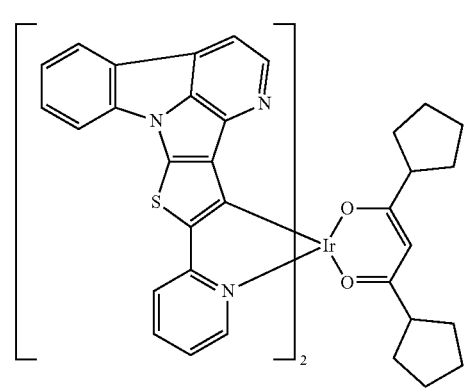
EX36
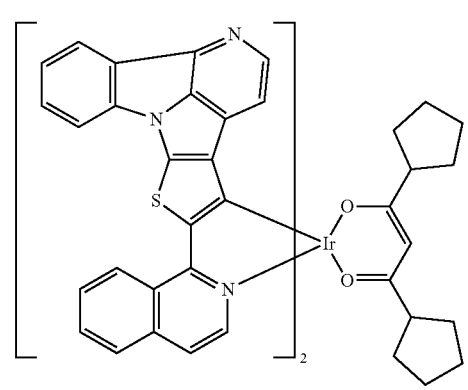

EX37 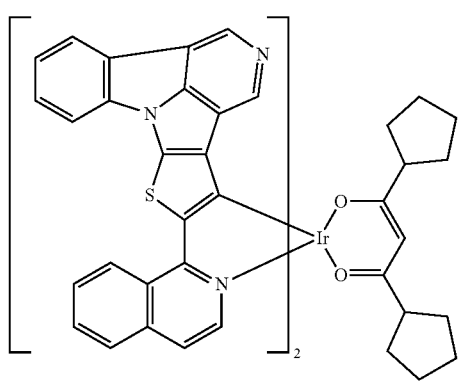
EX41 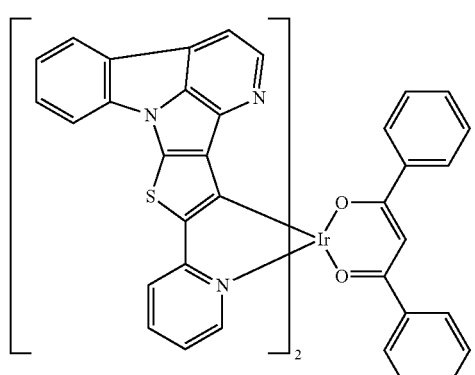
EX38 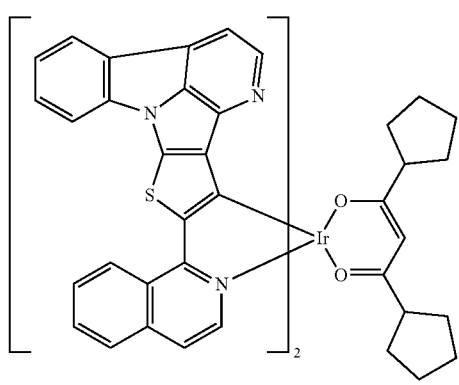
EX42 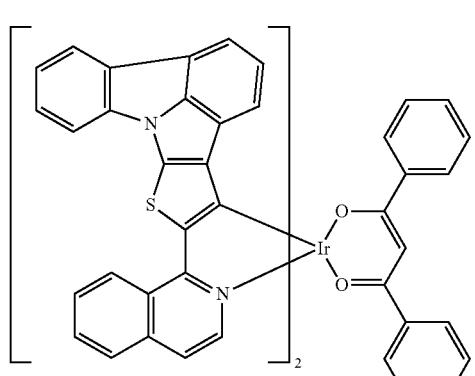
EX39 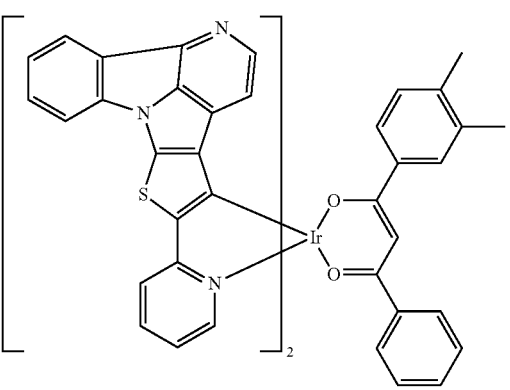
EX43 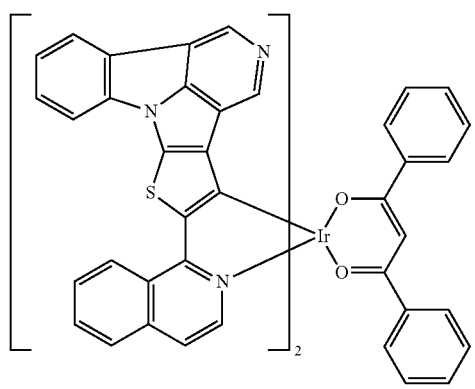
EX40 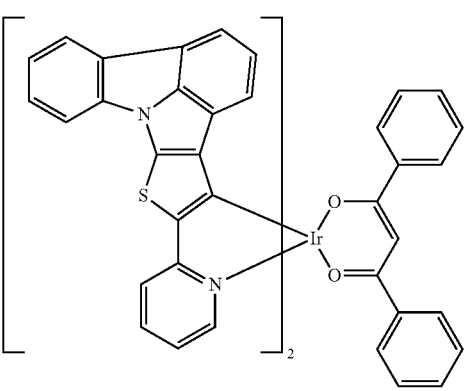
EX44 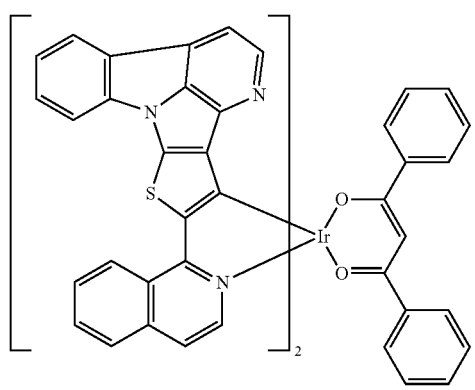

EX45
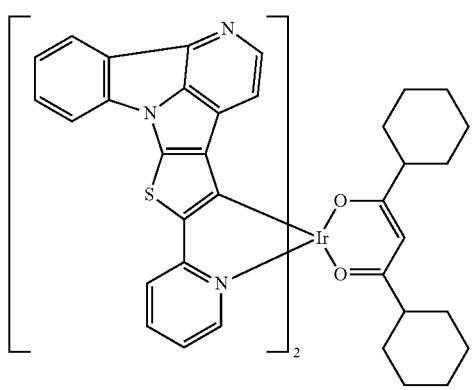
EX46
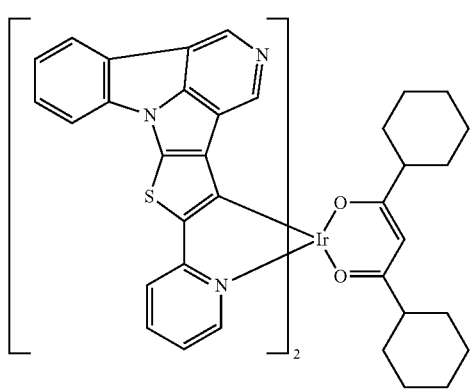
EX47
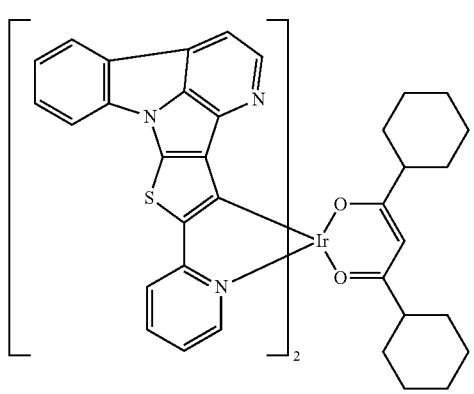
EX48
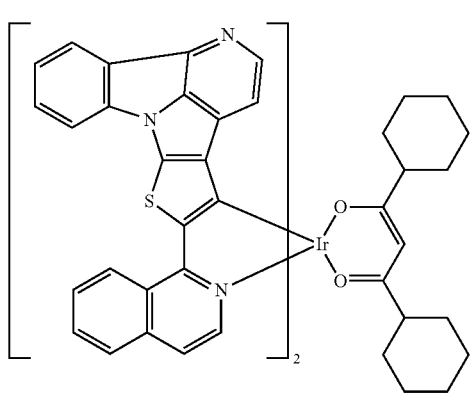
EX49
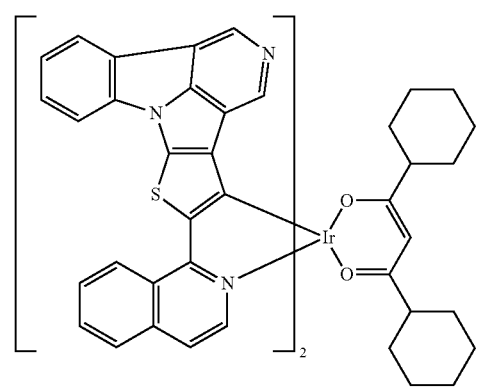
EX50
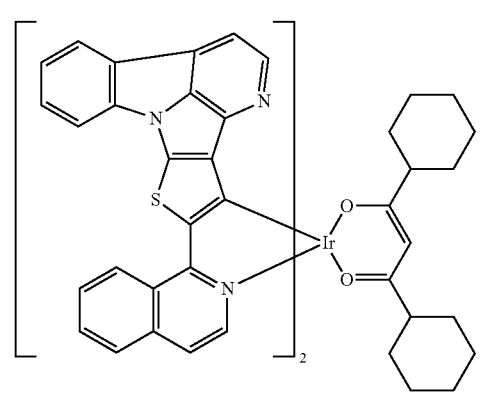
EX51
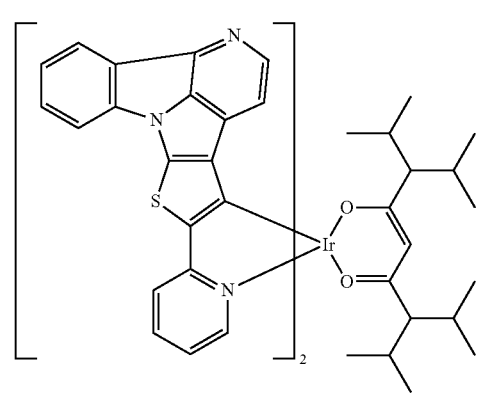
EX52
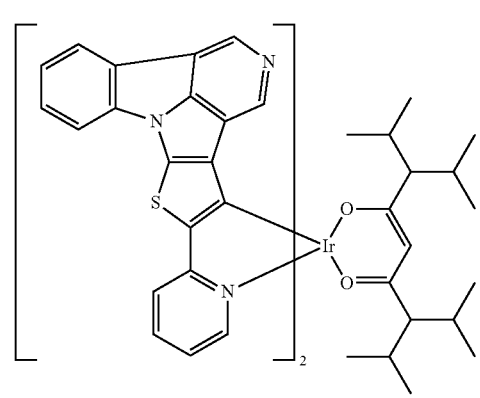

EX53
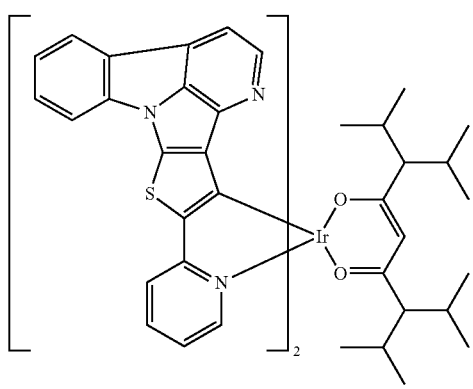
EX54
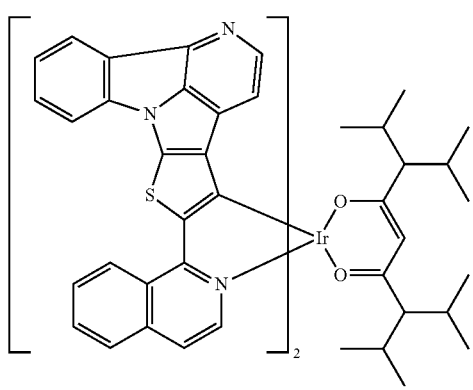
EX55
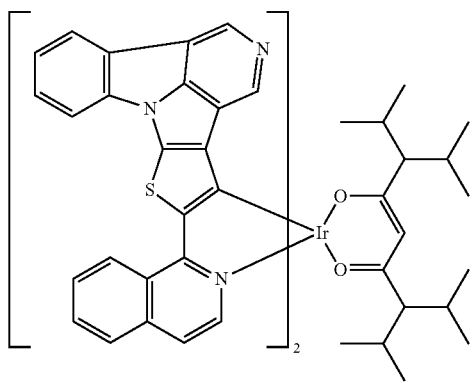
EX56
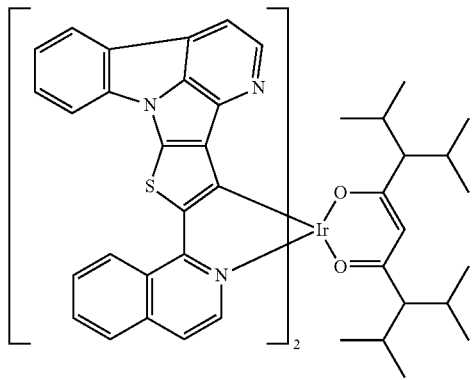
EX57
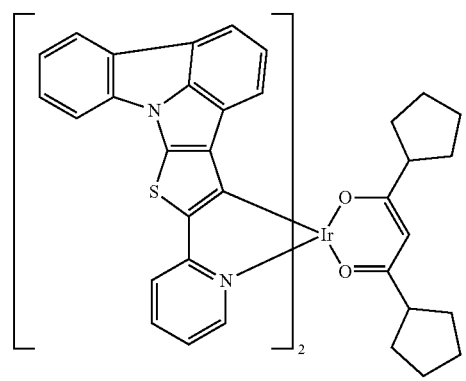
EX58
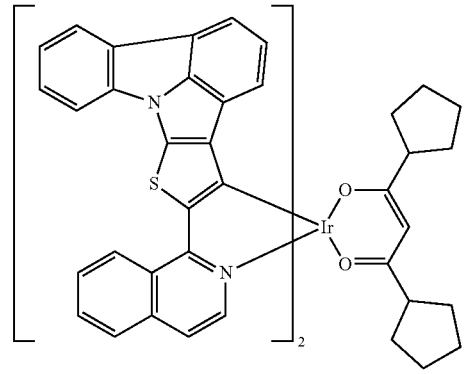
EX59
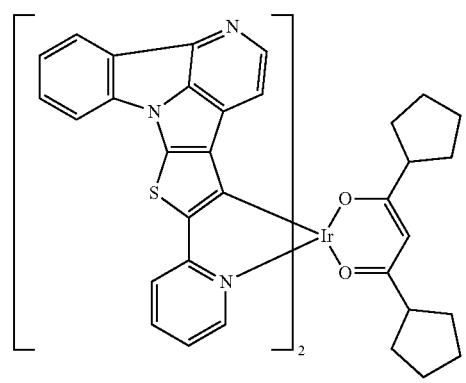
EX60
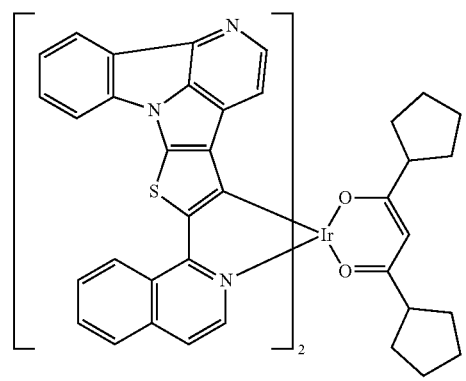

-continued
EX61
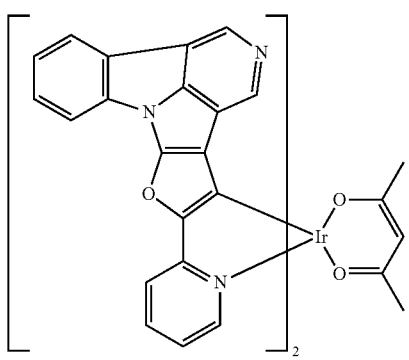
EX62
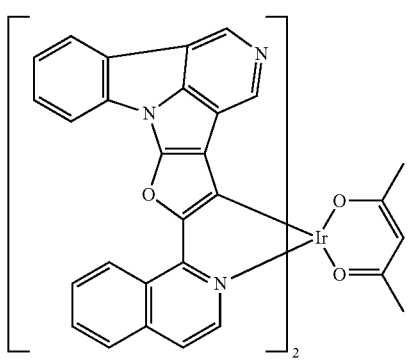
EX63
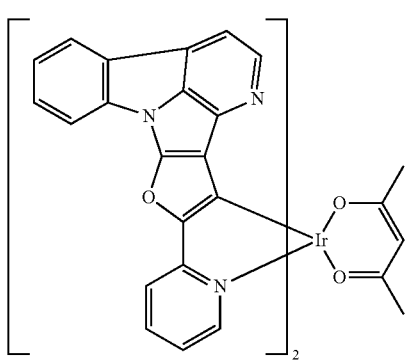
EX64
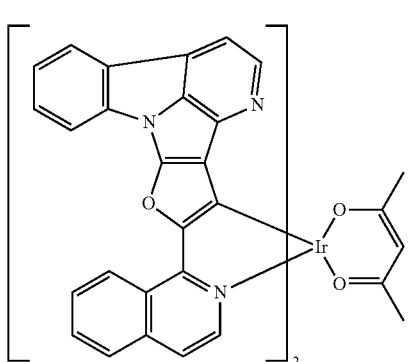
-continued
EX65
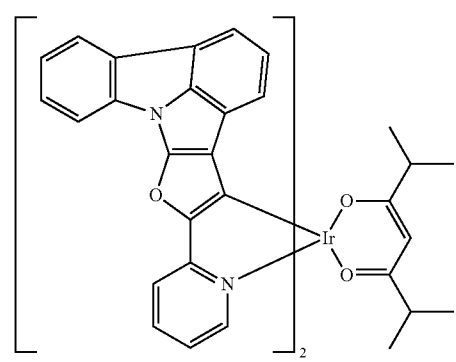
EX66
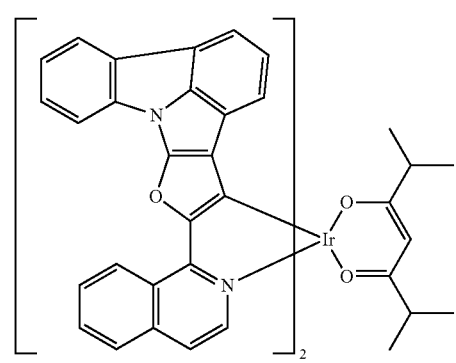
EX67
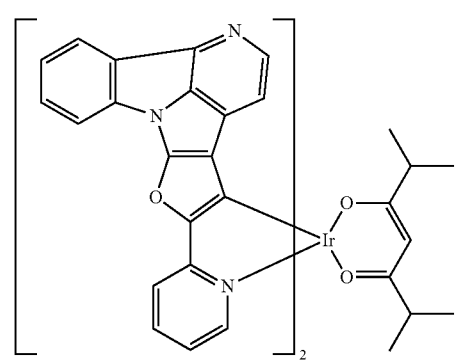
EX68
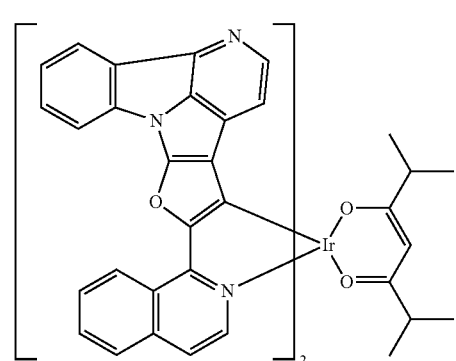

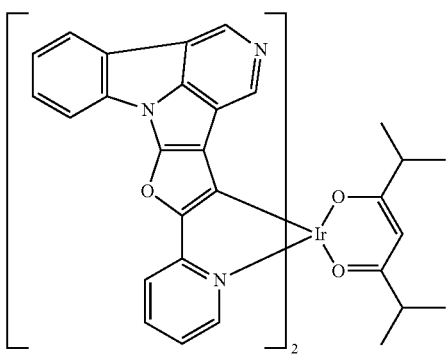 EX69
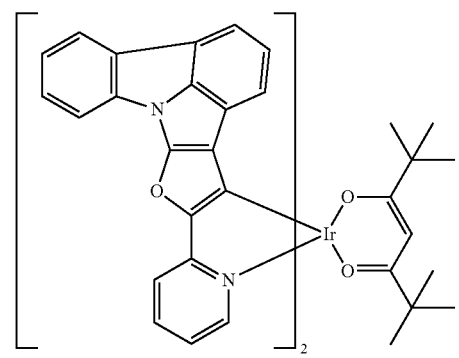 EX73
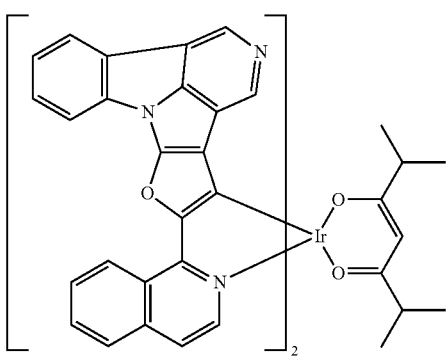 EX70
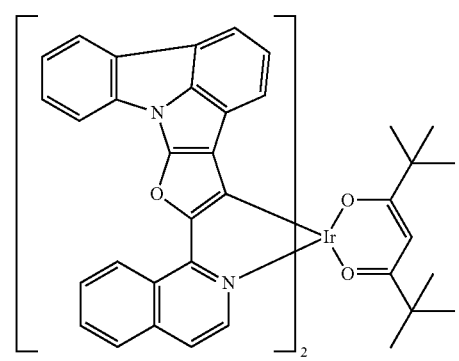 EX74
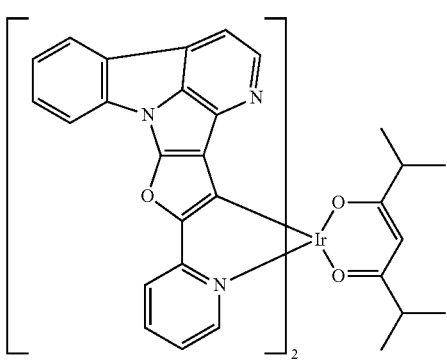 EX71
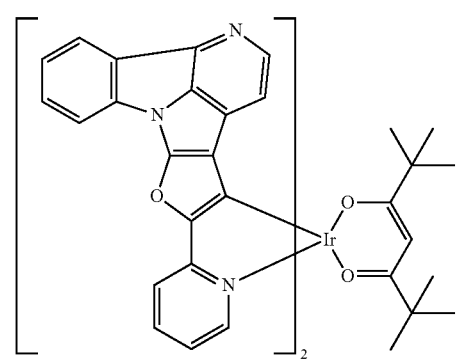 EX75
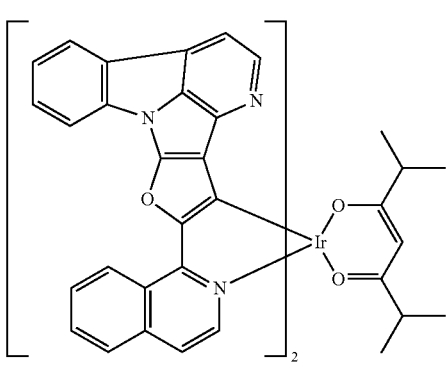 EX72
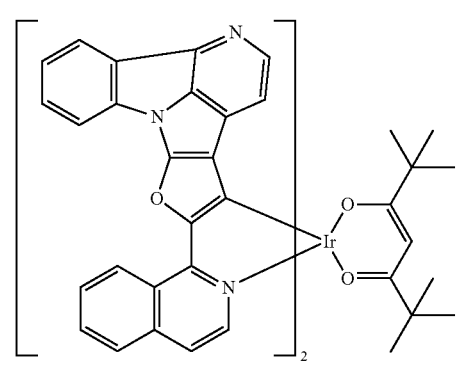 EX76

-continued
EX77
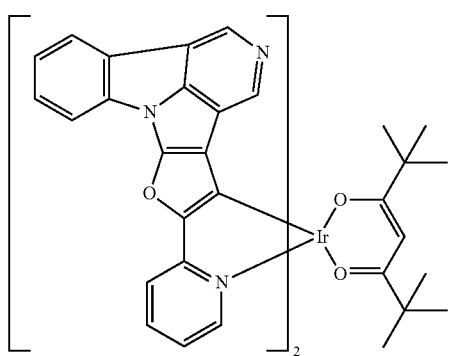
EX78
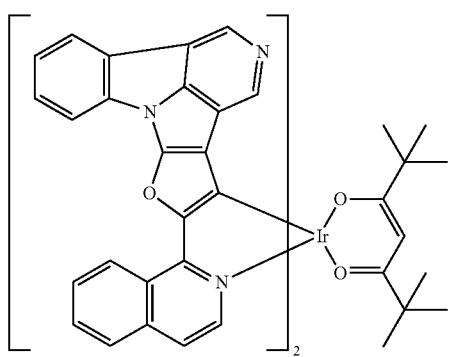
EX79
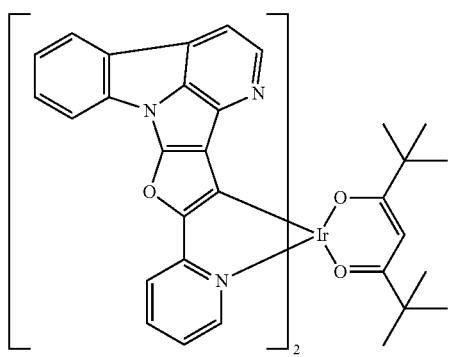
EX80
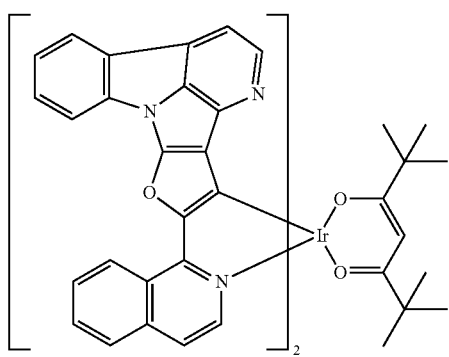
-continued
EX81
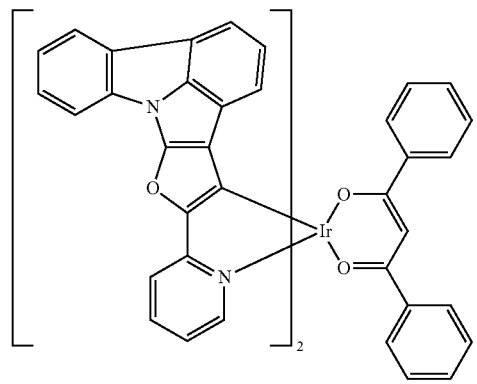
EX82
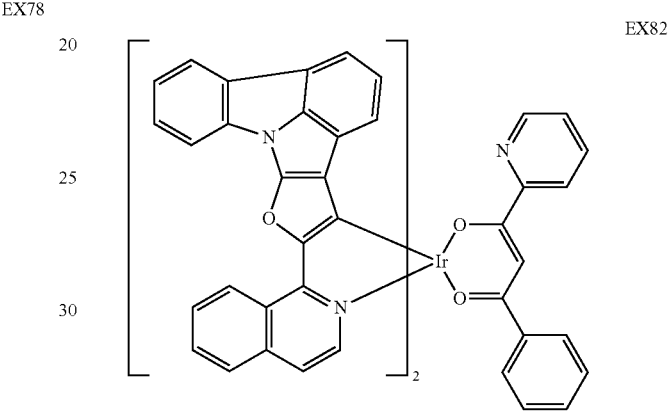
EX83
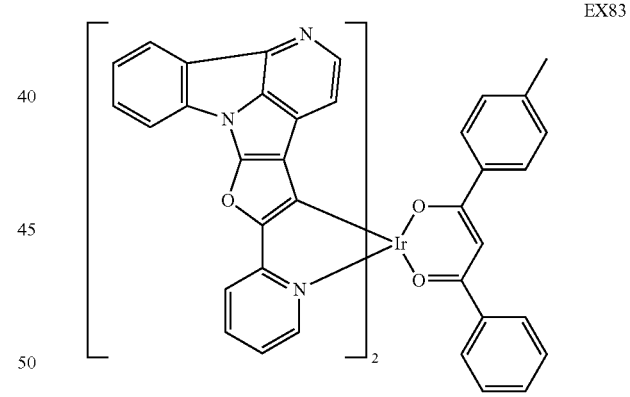
EX84
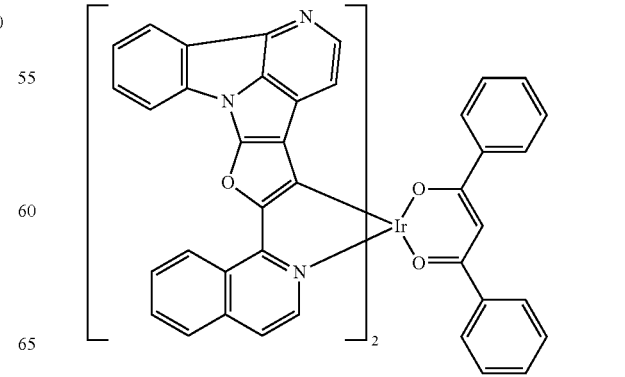

EX85
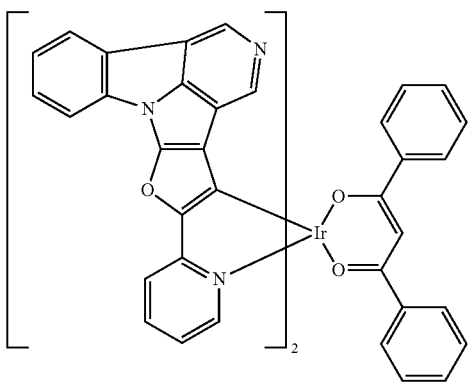
EX86
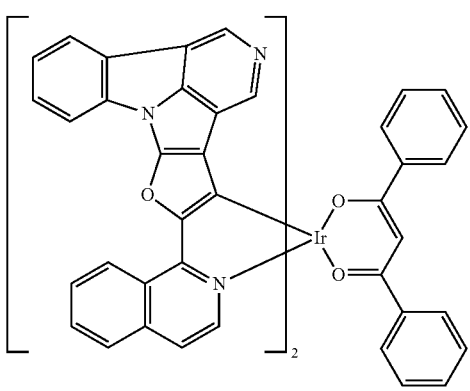
EX87
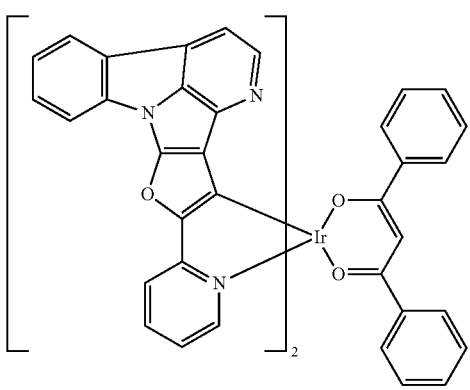
EX88
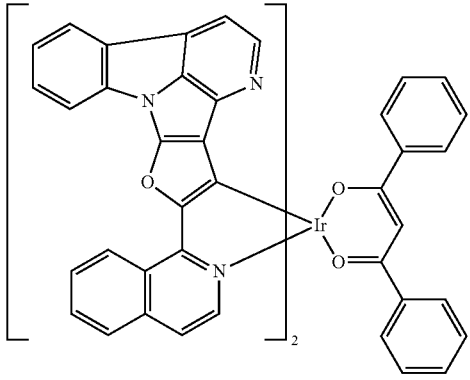
EX89
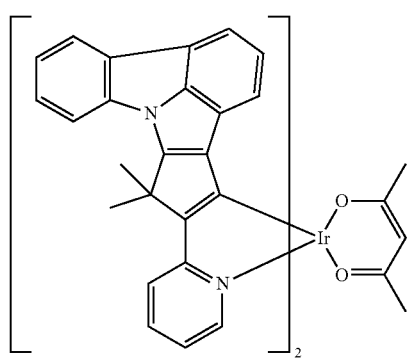
EX90
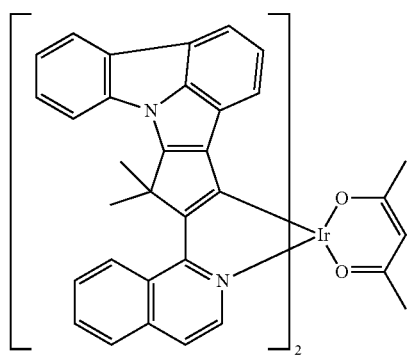
EX91
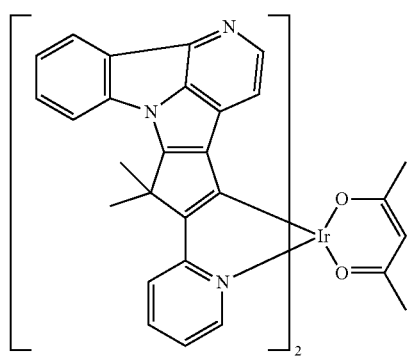
EX92
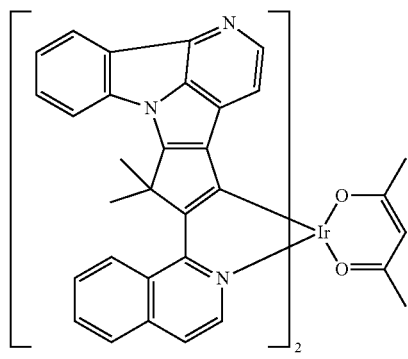

EX93 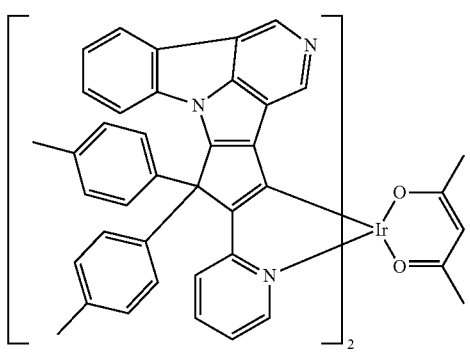
EX97 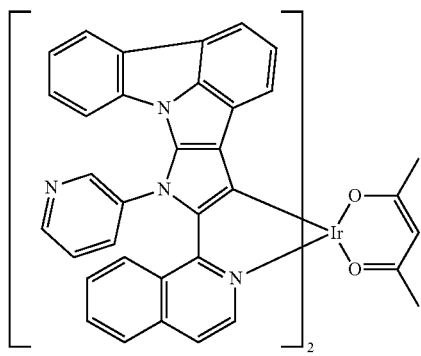
EX94 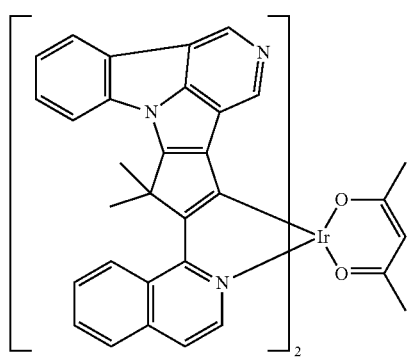
EX98 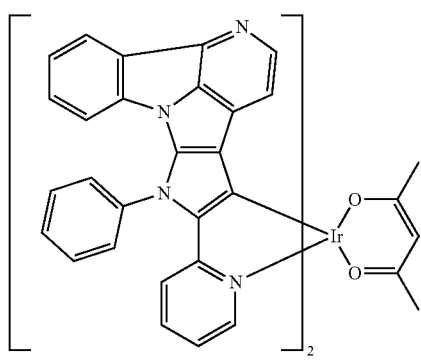
EX95 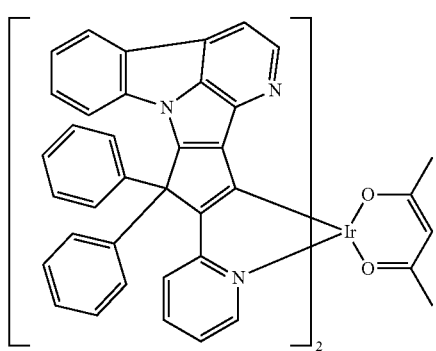
EX99 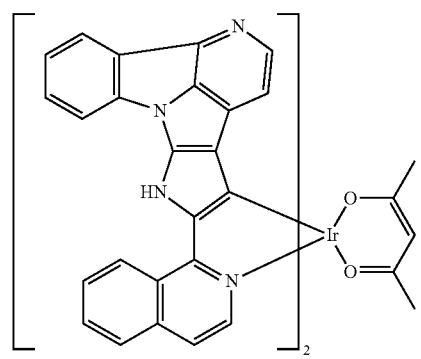
EX96 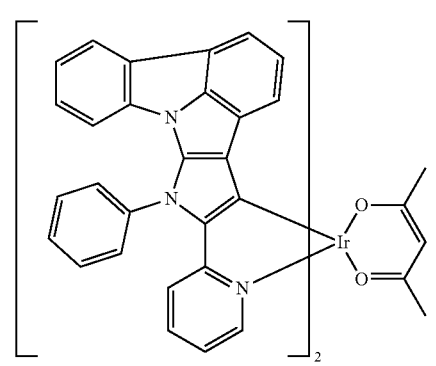
EX100 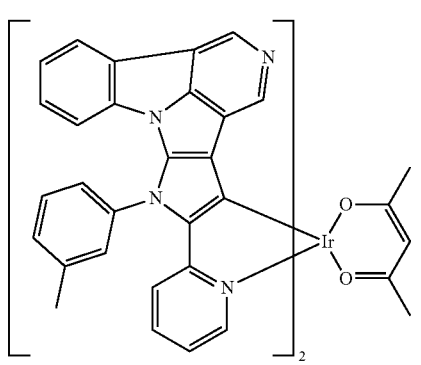

EX101
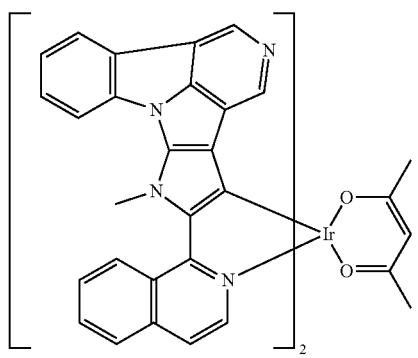
EX102
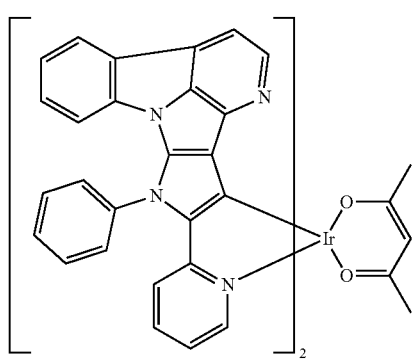
EX103
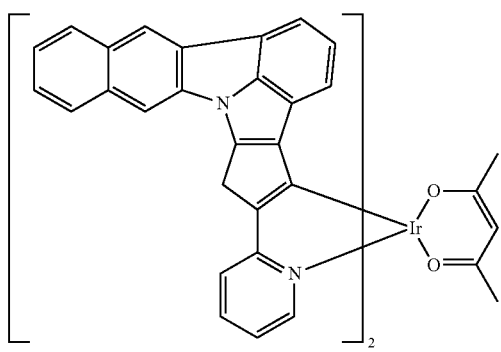
EX104
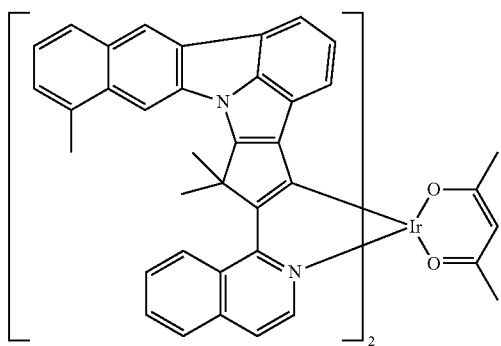
EX105
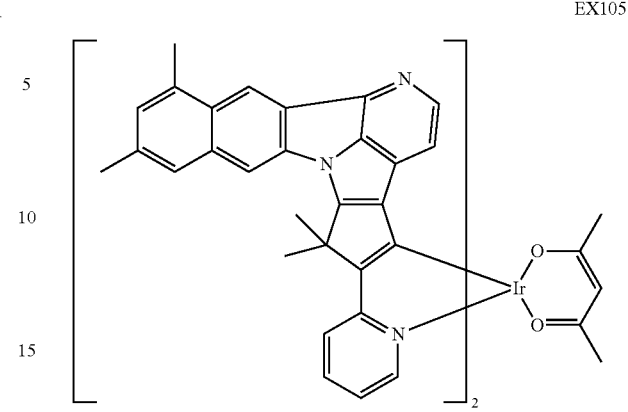
EX106
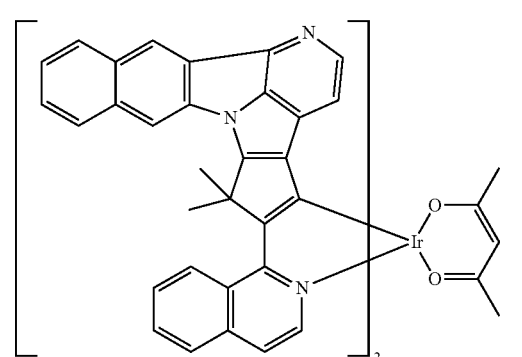
EX107
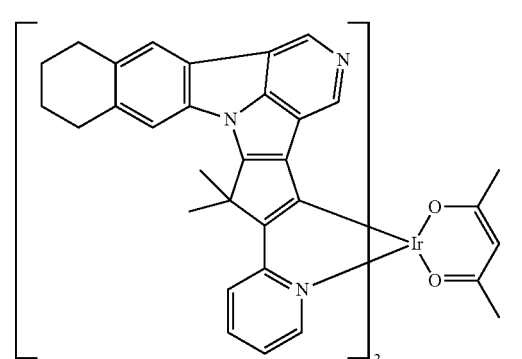
EX108
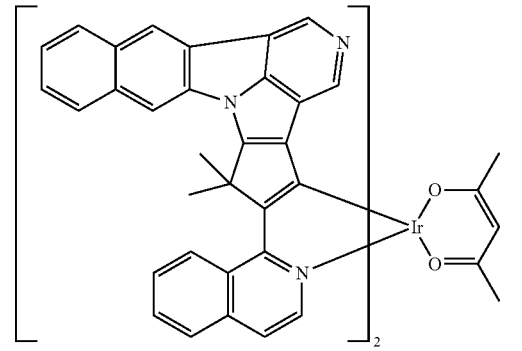

EX109
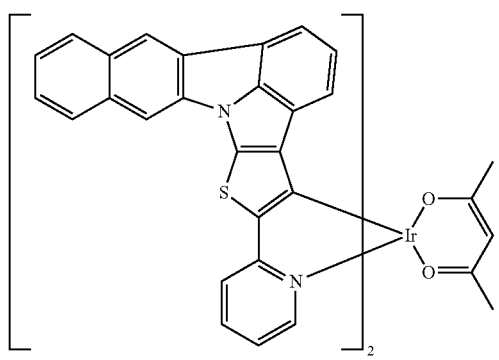
EX113
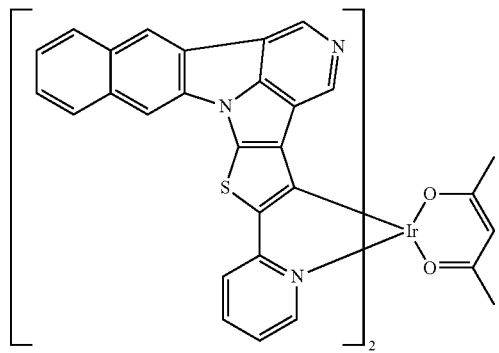
EX110
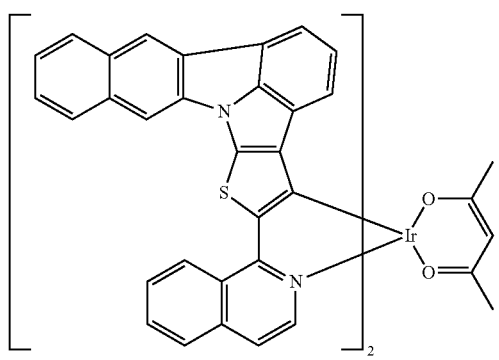
EX114
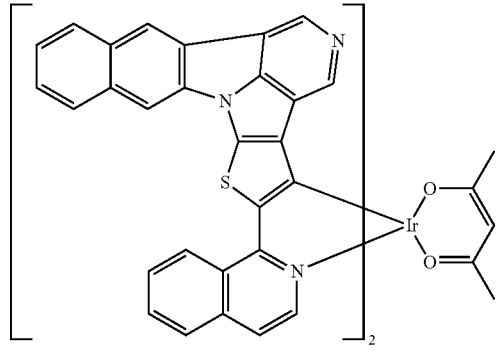
EX111
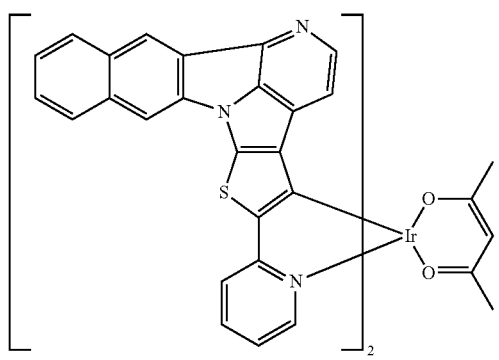
EX115
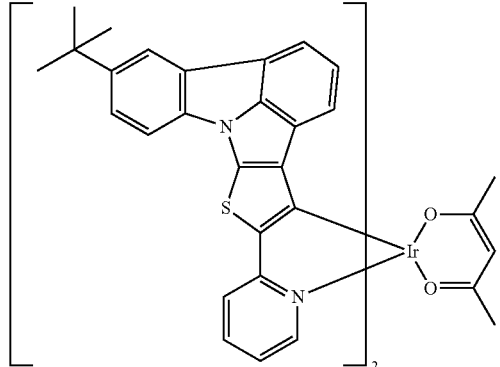
EX112
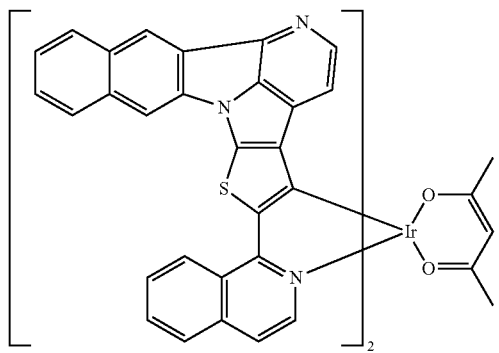
EX116
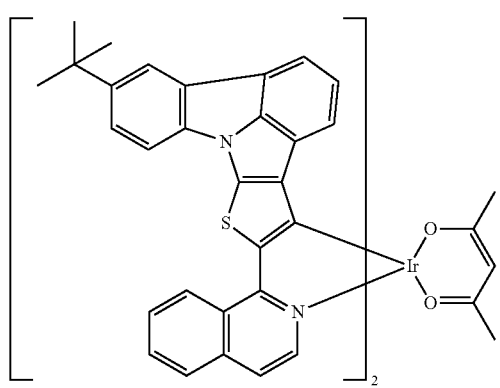

-continued
EX117
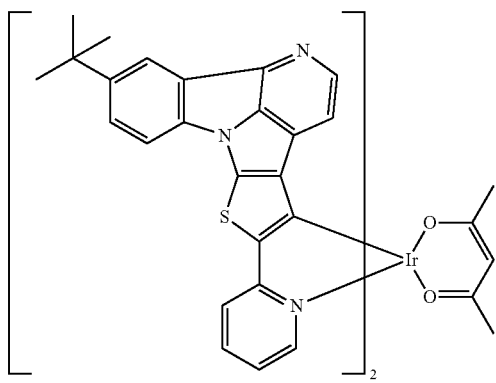
EX118
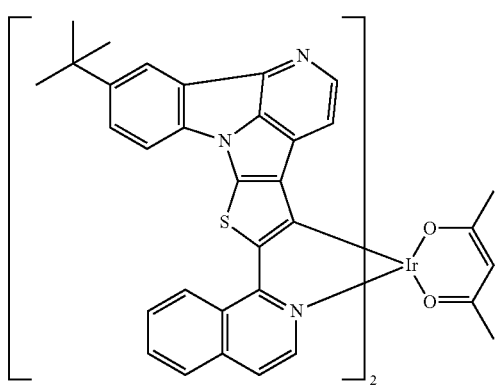
EX119
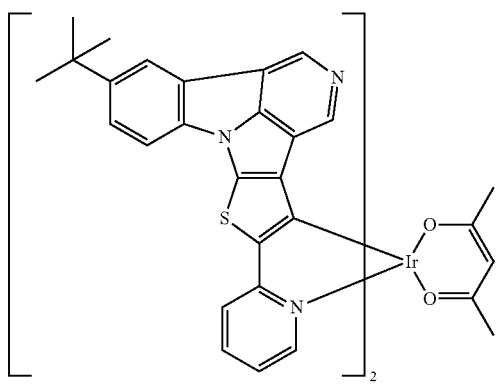
EX120
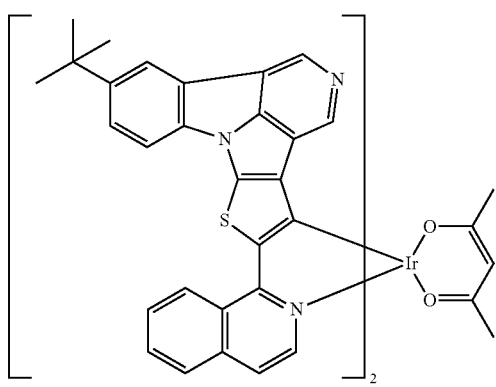
-continued
EX121
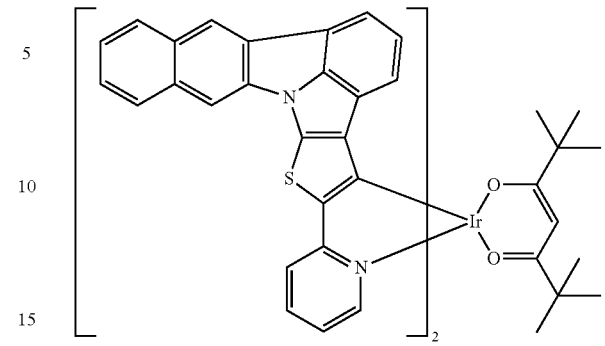
EX122
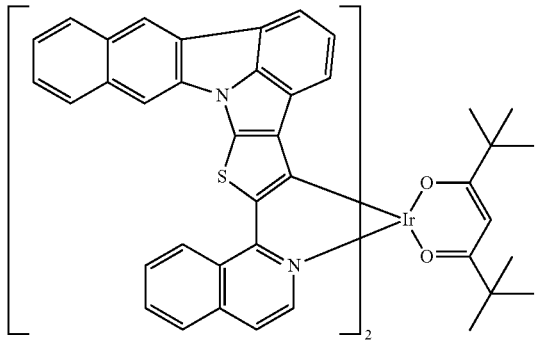
EX123
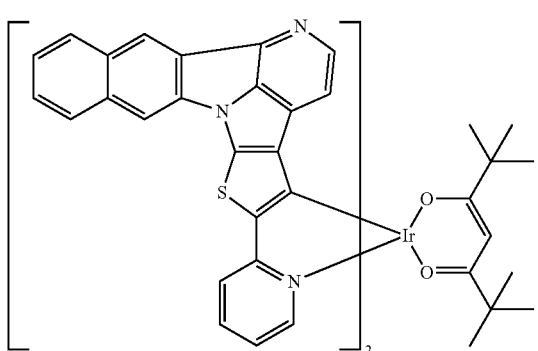
EX124
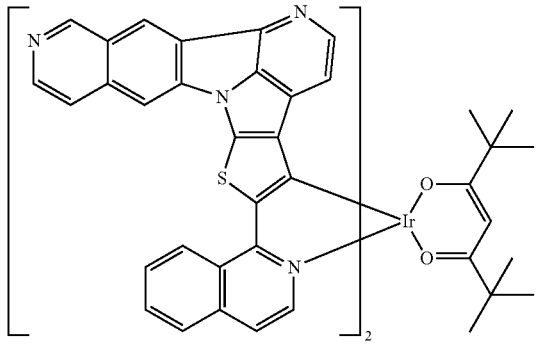

EX125
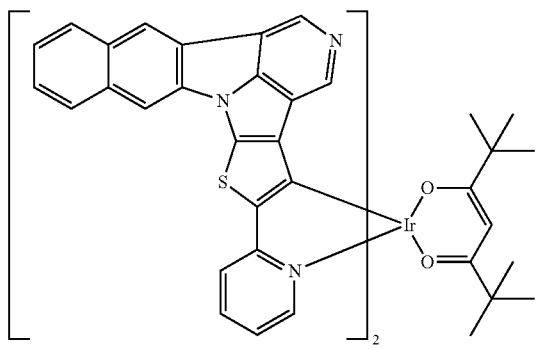
EX126
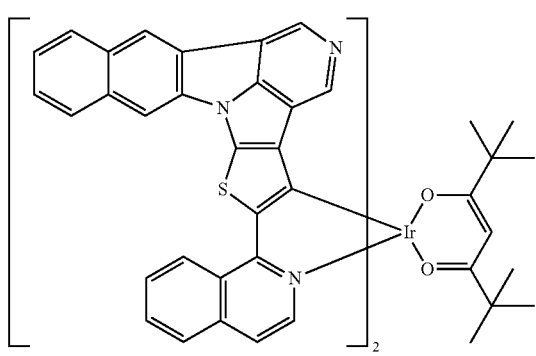
EX127
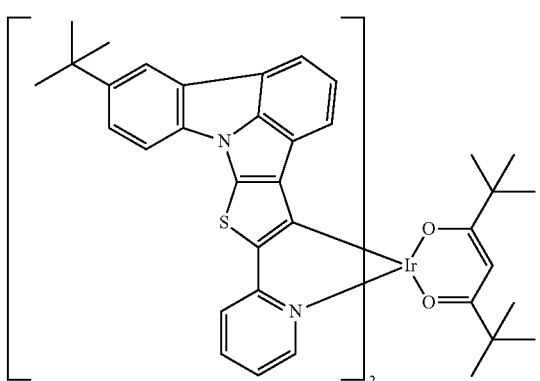
EX128
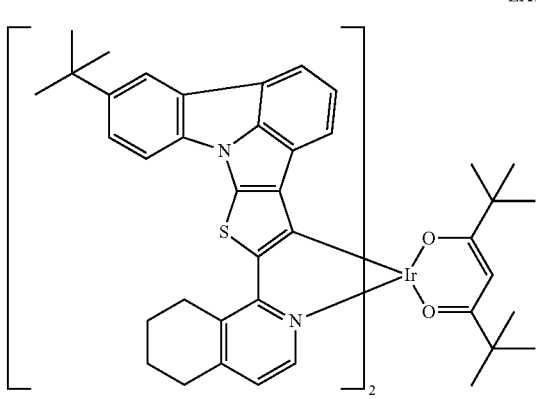
EX129
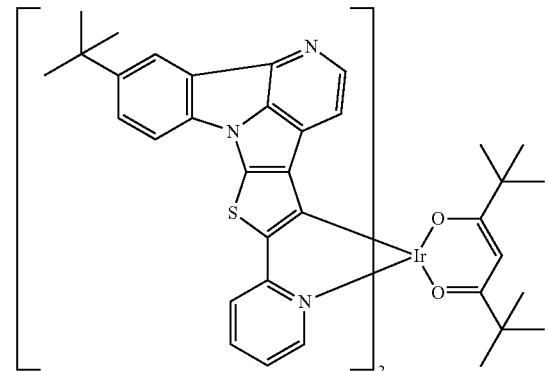
EX130
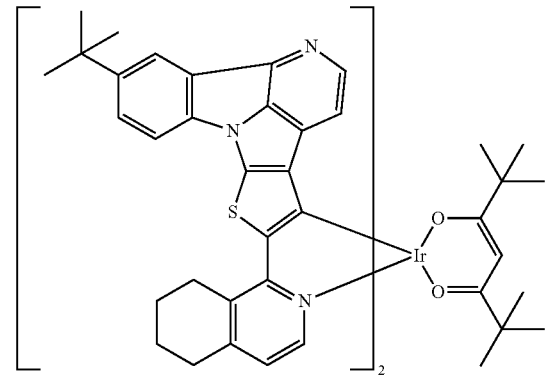
EX131
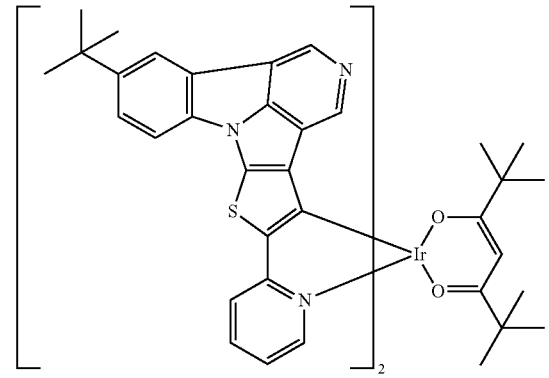
EX132
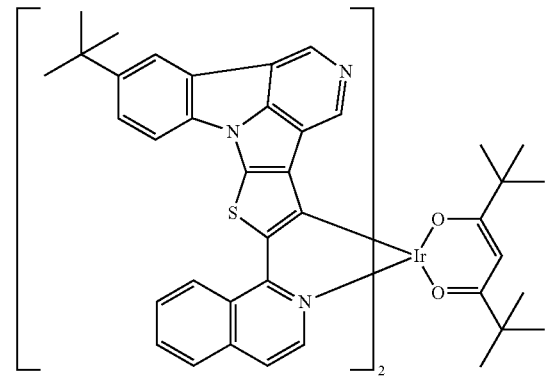

115
-continued
EX133
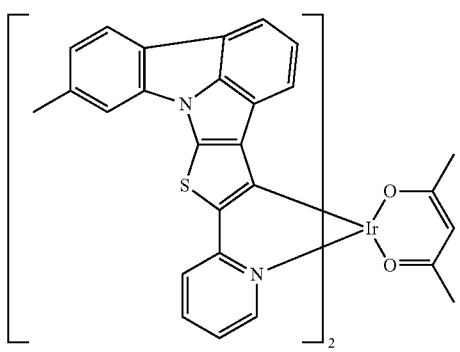
EX134
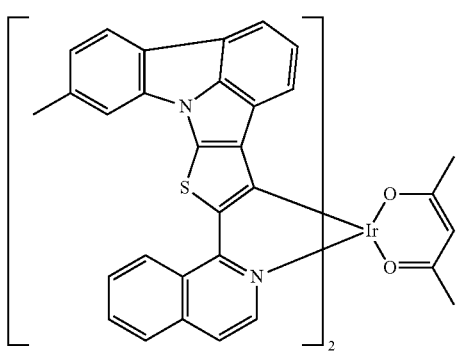
EX135
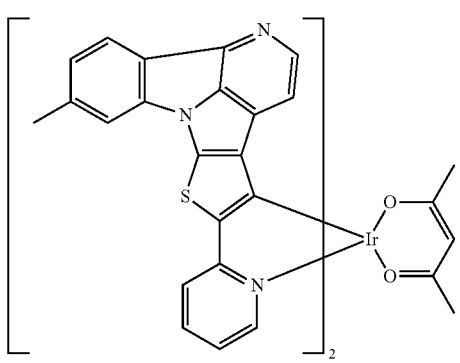
EX136
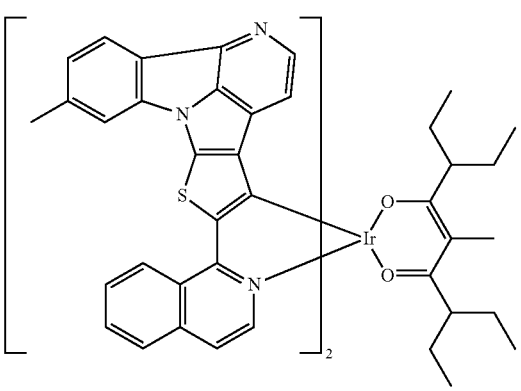
116
-continued
EX137
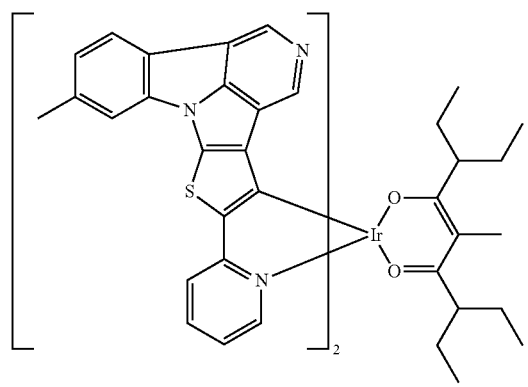
EX138
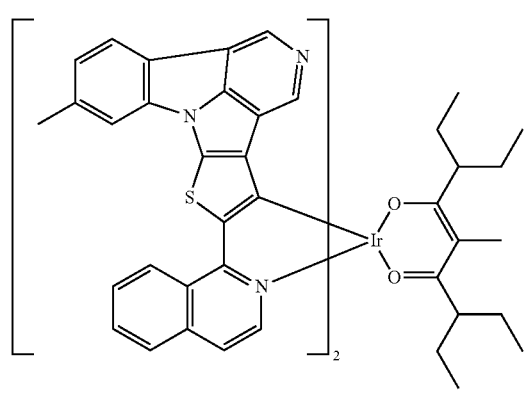
EX139
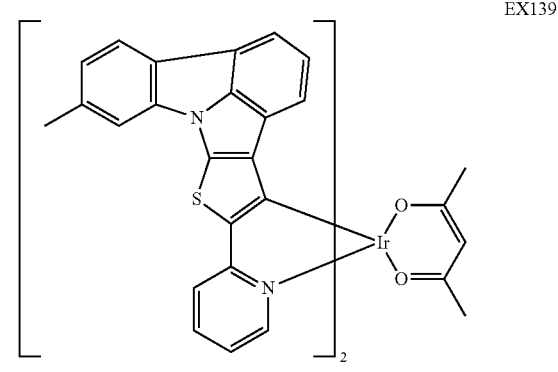
EX140
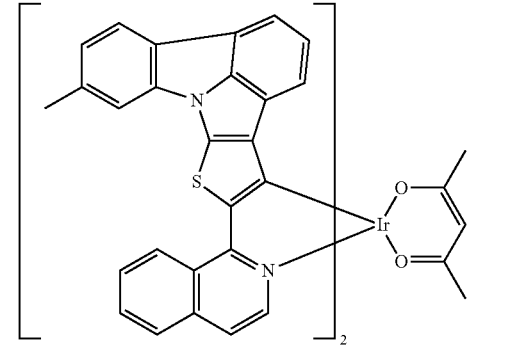

EX141 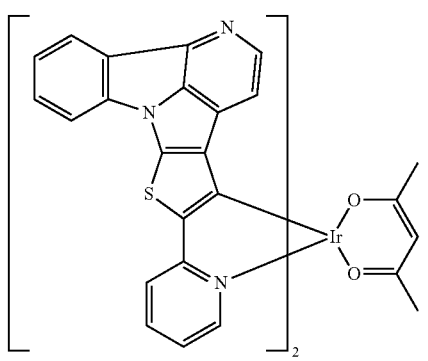
EX145 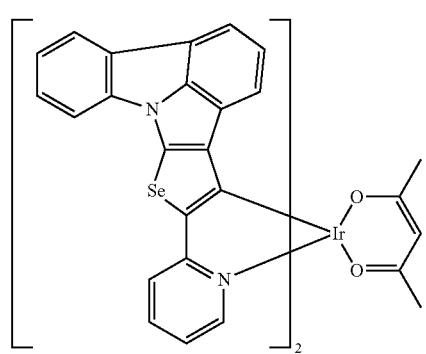
EX142 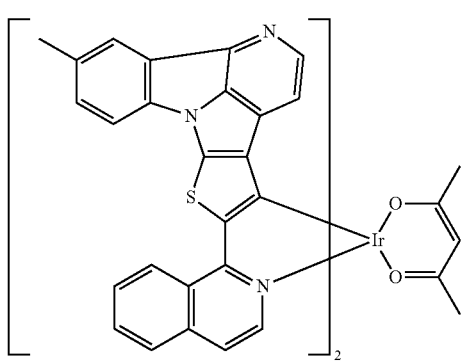
EX146 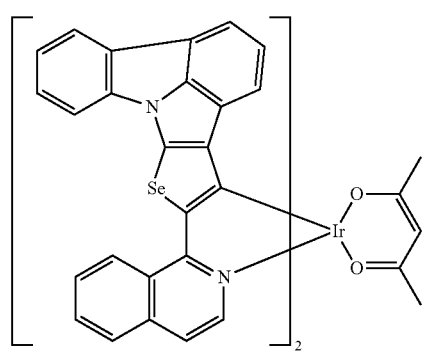
EX143 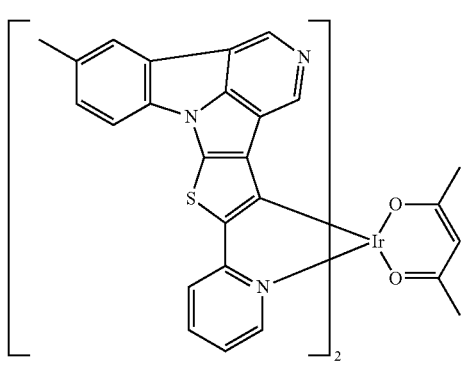
EX147 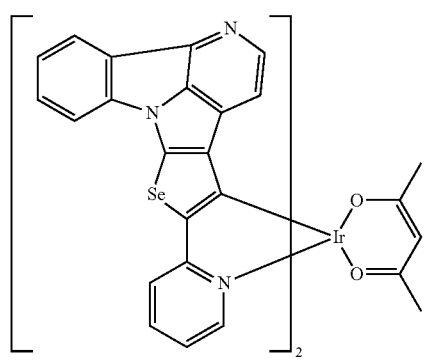
EX144 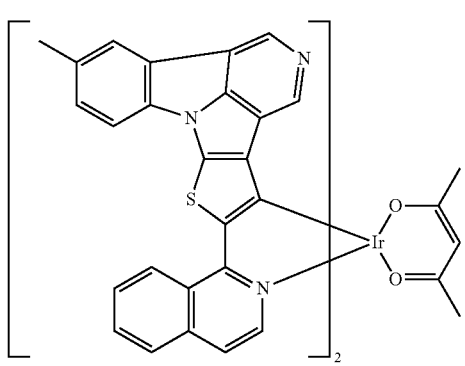
EX148 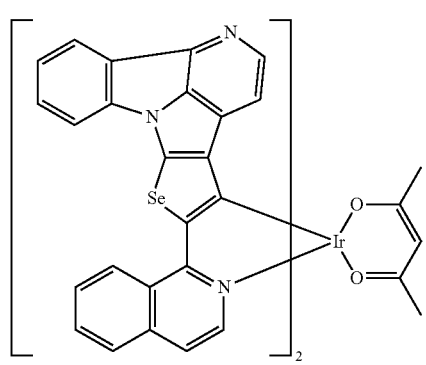

EX149
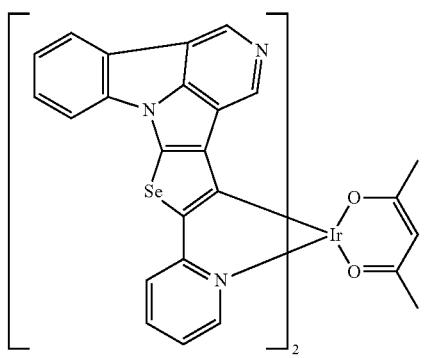
EX153
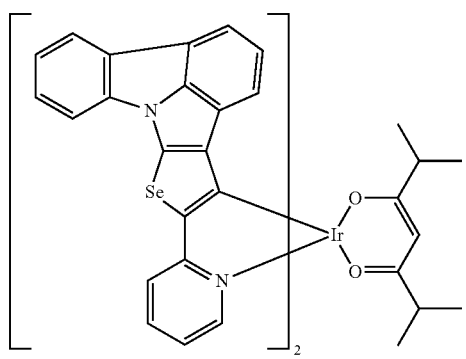
EX150
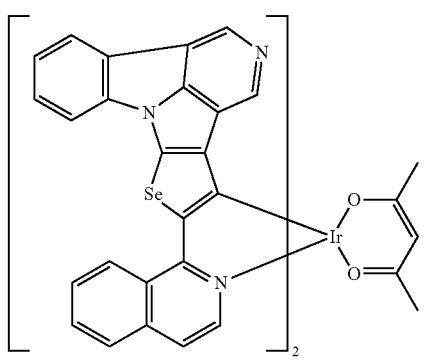
EX154
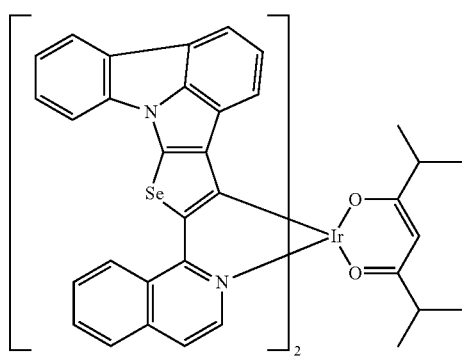
EX151
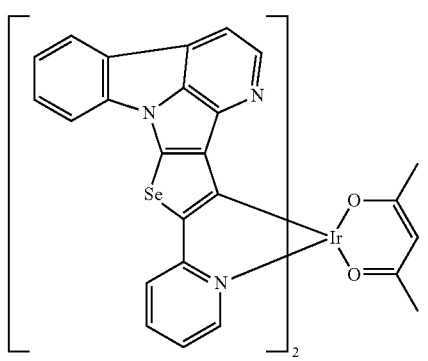
EX155
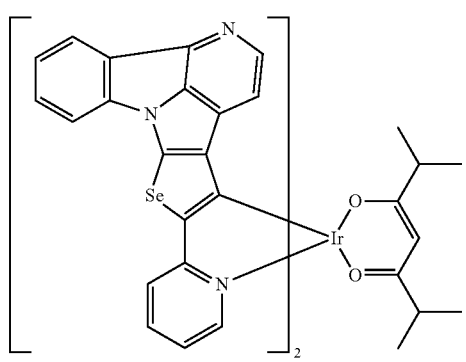
EX152
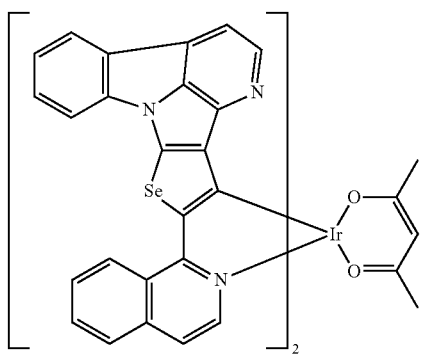
EX156
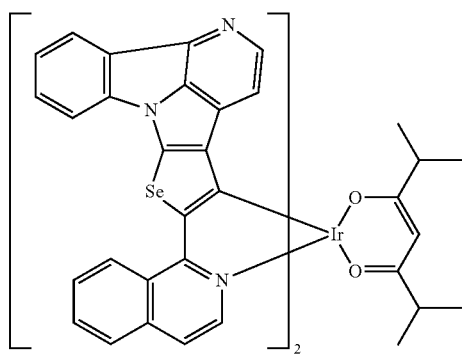

EX157
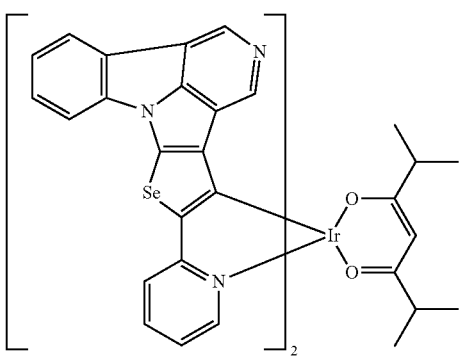
EX158
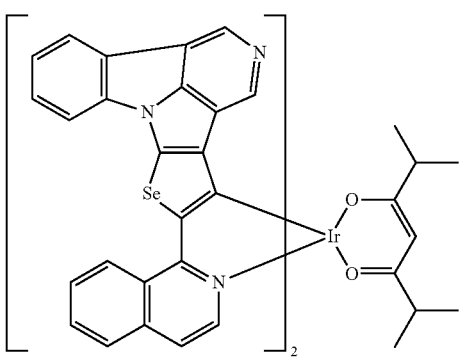
EX159
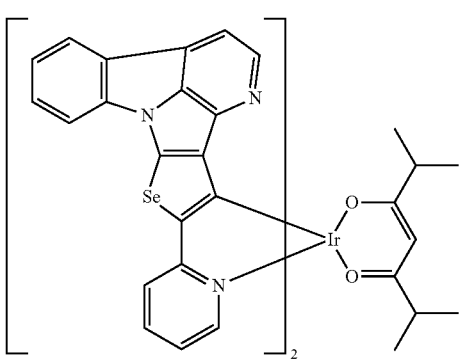
EX160
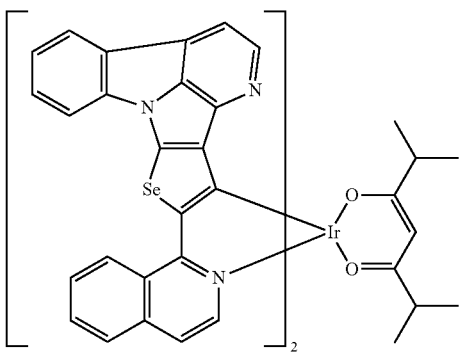
EX161
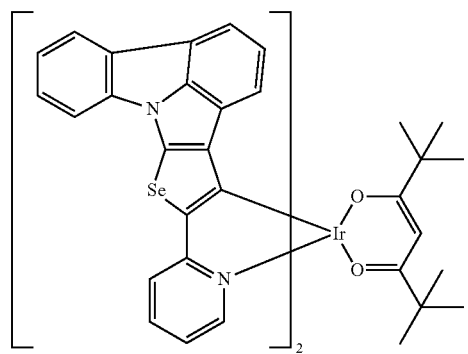
EX162
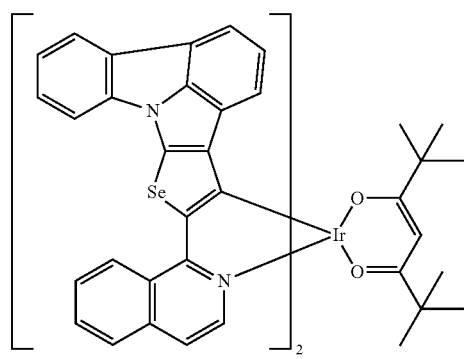
EX163
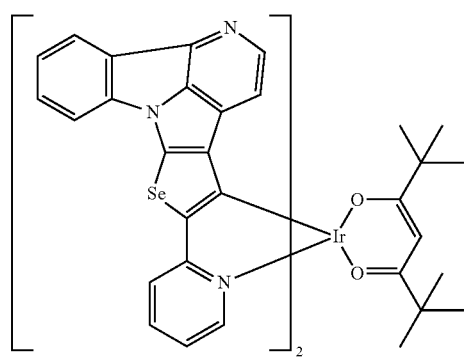
EX164
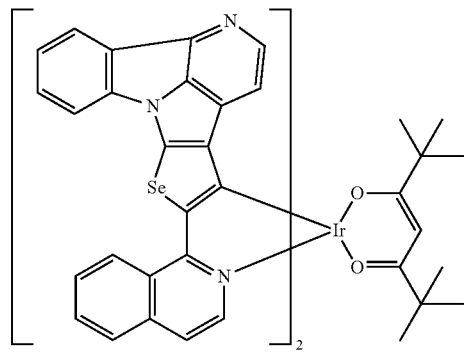

-continued
EX165
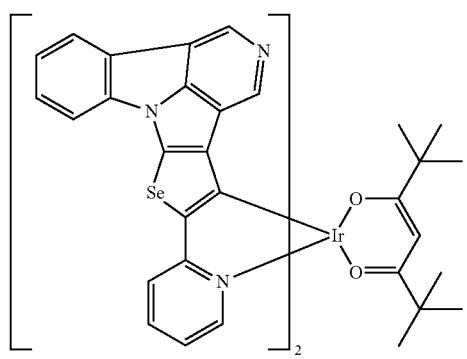
EX166
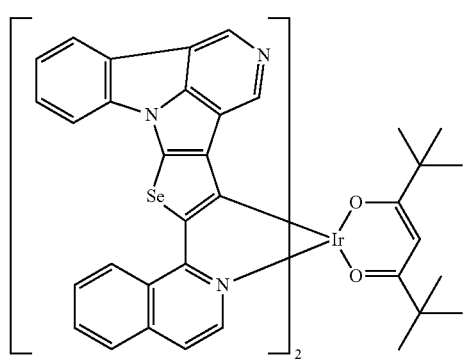
EX167
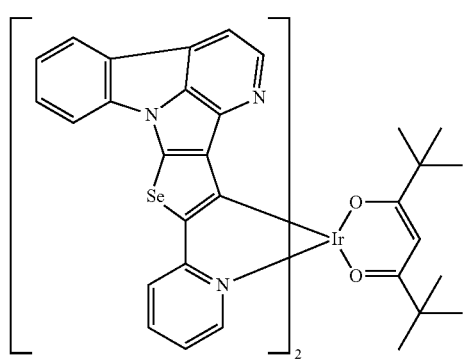
EX168
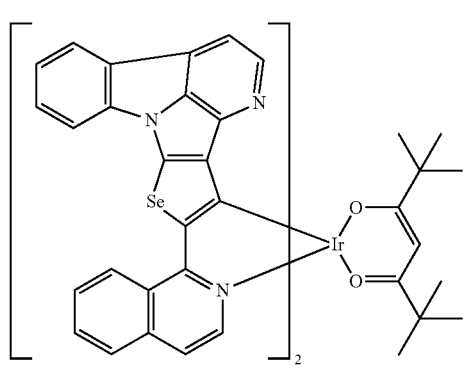
-continued
EX169
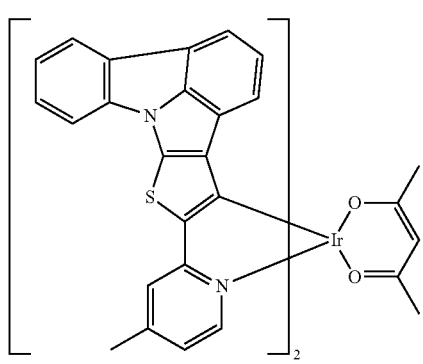
EX170
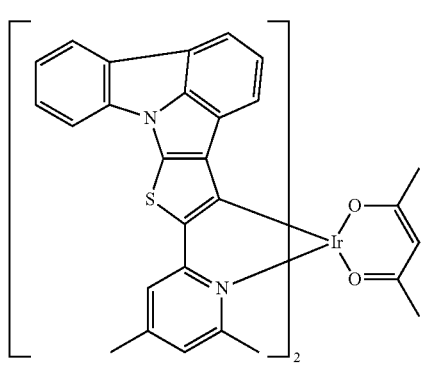
EX171
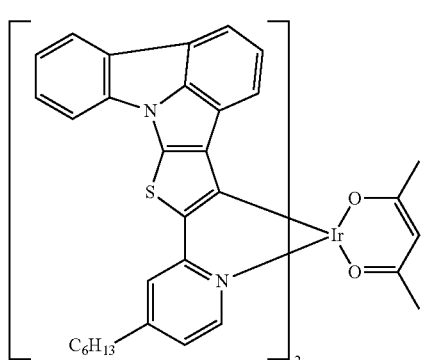
EX172
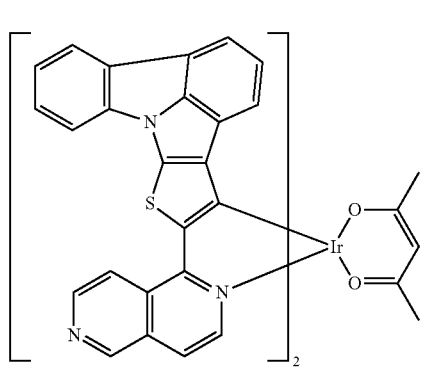

EX173 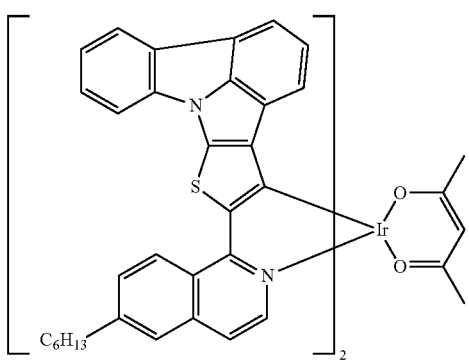
EX177 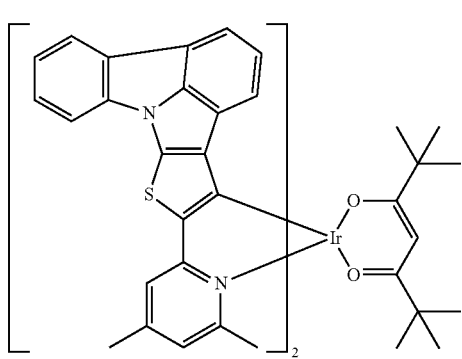
EX174 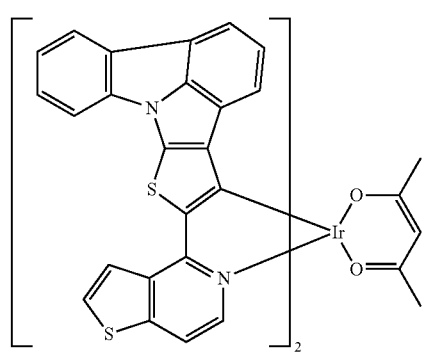
EX178 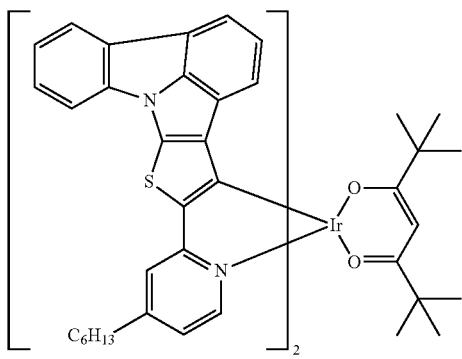
EX175 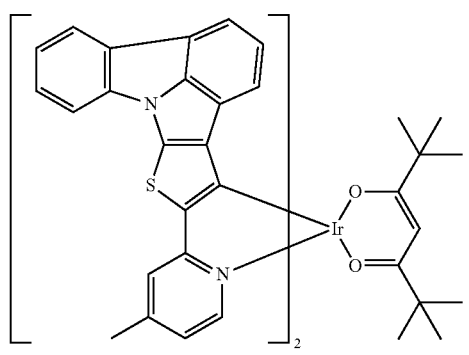
EX179 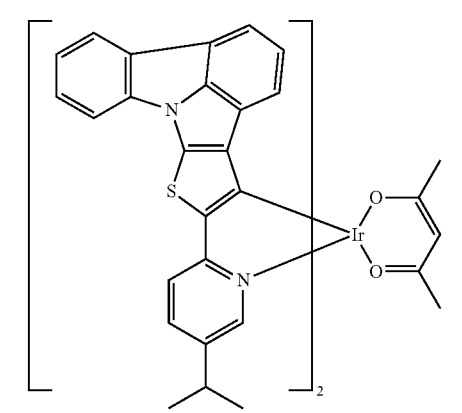
EX176 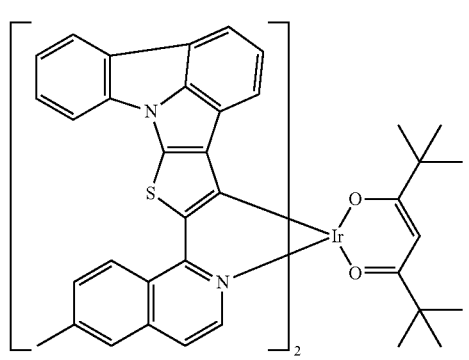
EX180 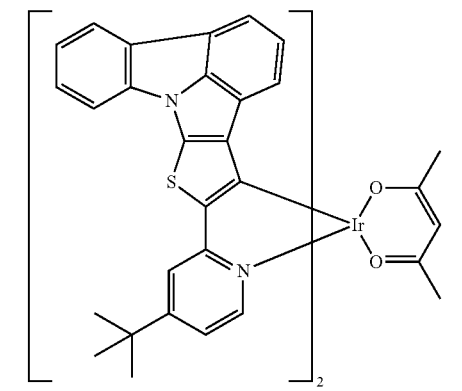

EX181
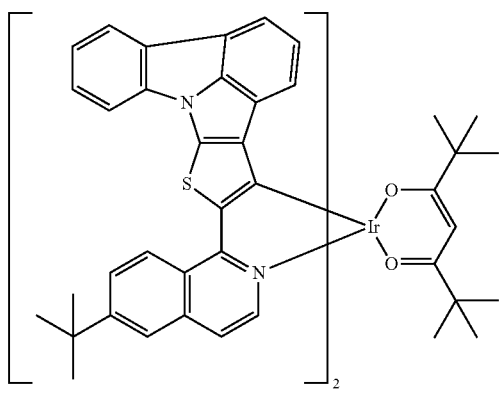
EX182
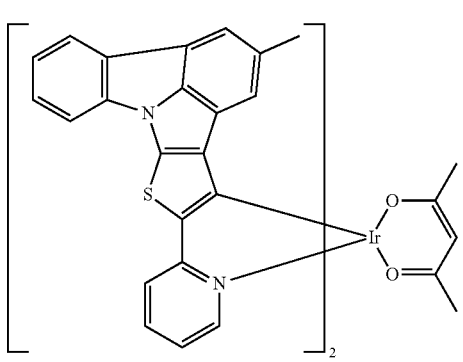
EX183
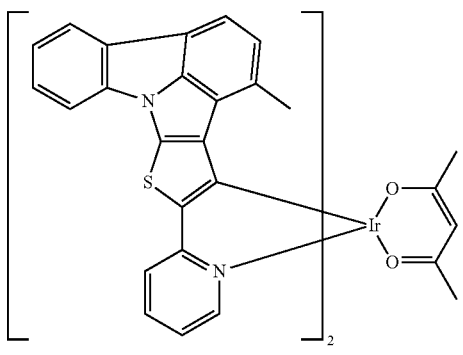
EX184
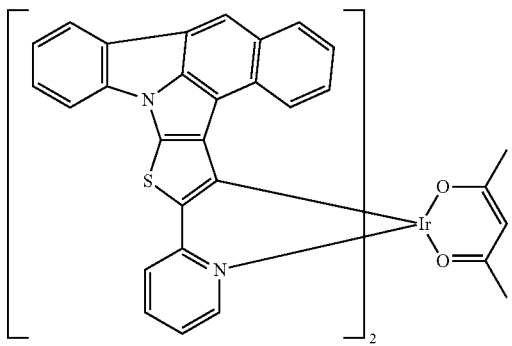
EX185
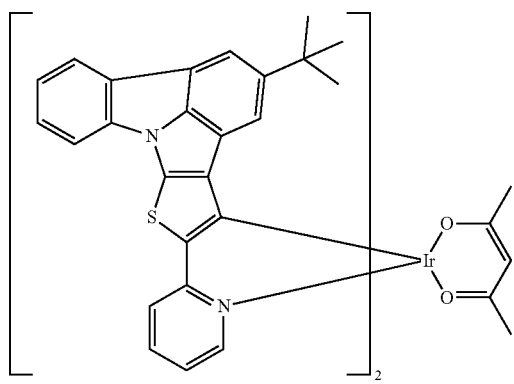
EX186
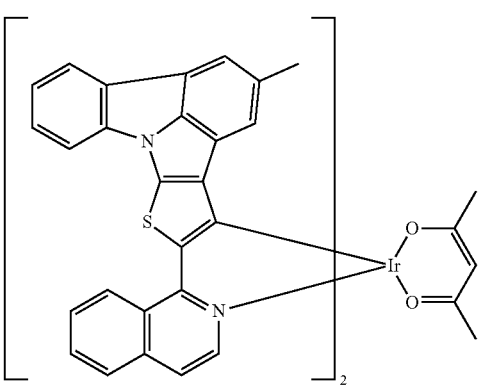
EX187
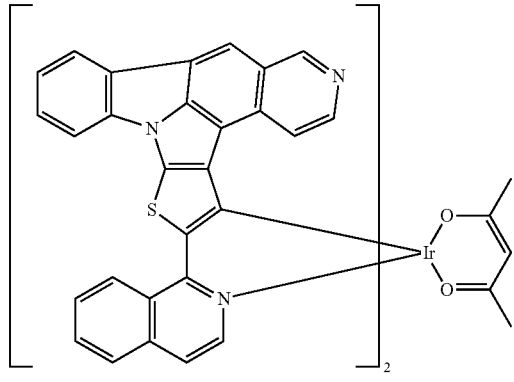
EX188
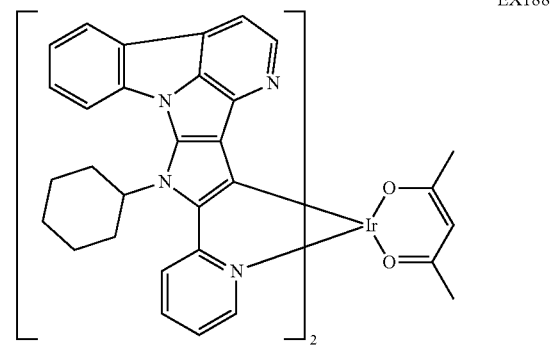

-continued

EX189

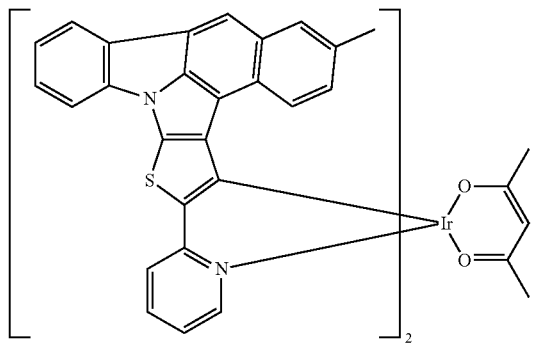

EX190

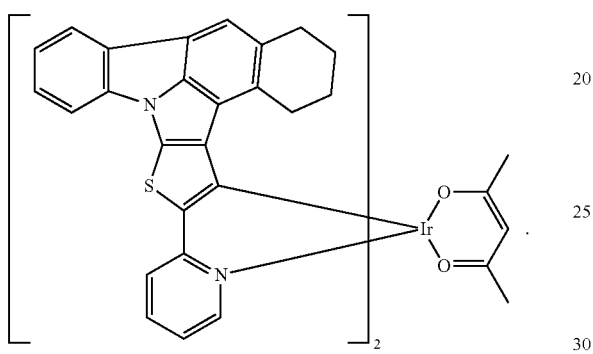

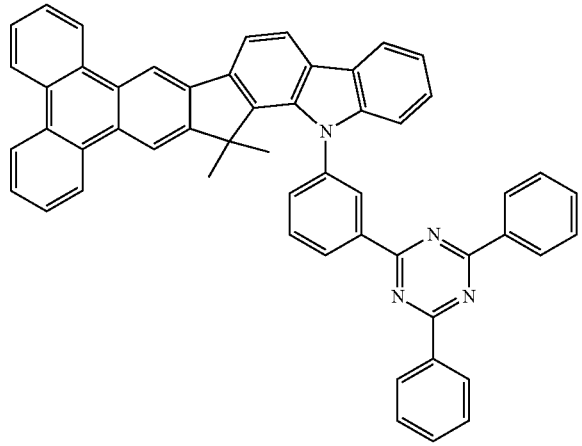

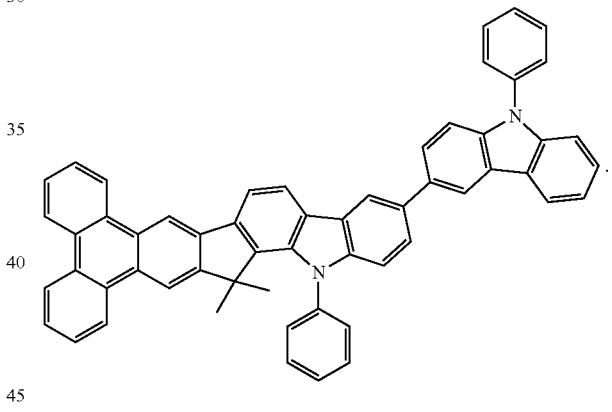

4. An organic electroluminescence device, comprising a pair of electrodes composed of a cathode and an anode, and a light emitting layer between the pair of electrodes, wherein the light emitting layer comprises the iridium complex of claim 1.

5. The organic electroluminescence device of claim 4, wherein the light emitting layer further includes a host material, and the iridium complex of formula (1) is used as a phosphorescent dopant material.

6. The organic electroluminescence device of claim 5, wherein the host material is selected from the following compounds:

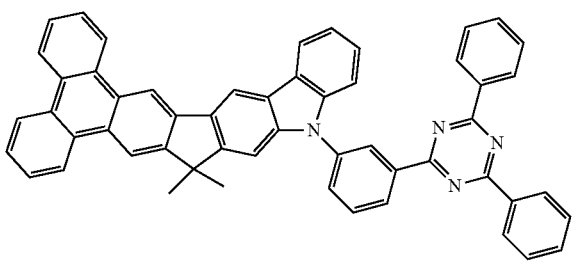

7. The organic electroluminescence device of claim 4, wherein the light emitting layer emits red phosphorescence.

8. The organic electroluminescence device of claim 4, wherein the organic electroluminescence device is a lighting panel.

9. The organic electroluminescence device of claim 4, wherein the organic electroluminescence device is a backlight panel.

* * * * *